(12) United States Patent
Koh et al.

(10) Patent No.: US 9,802,994 B2
(45) Date of Patent: Oct. 31, 2017

(54) COMPOSITION FOR PREVENTING OR TREATING FRACTURE OR OSTEOPOROSIS USING SLIT-ROBO SYSTEM

(71) Applicant: THE ASAN FOUNDATION, Seoul (KR)

(72) Inventors: Jung-Min Koh, Seoul (KR); Ghi Su Kim, Seoul (KR); Seung Hun Lee, Gyeonggi-do (KR); Young-Sun Lee, Gyeonggi-do (KR); Beom-Jun Kim, Seoul (KR)

(73) Assignee: THE ASAN FOUNDATION, Seoul (KR)

( * ) Notice: Subject to any disclaimer, the term of this patent is extended or adjusted under 35 U.S.C. 154(b) by 0 days.

(21) Appl. No.: 14/408,275

(22) PCT Filed: Jun. 14, 2013

(86) PCT No.: PCT/KR2013/005282
§ 371 (c)(1),
(2) Date: Dec. 15, 2014

(87) PCT Pub. No.: WO2013/187730
PCT Pub. Date: Dec. 19, 2013

(65) Prior Publication Data
US 2015/0175673 A1   Jun. 25, 2015

(30) Foreign Application Priority Data
Jun. 15, 2012 (KR) ........................ 10-2012-0064302

(51) Int. Cl.
*A61K 38/17* (2006.01)
*C07K 14/47* (2006.01)
*A61P 19/10* (2006.01)
*G01N 33/68* (2006.01)
*C07K 14/705* (2006.01)
*G01N 33/50* (2006.01)
*A23L 33/195* (2016.01)
*A61K 38/00* (2006.01)

(52) U.S. Cl.
CPC ............ *C07K 14/47* (2013.01); *A23L 33/195* (2016.08); *A61K 38/1709* (2013.01); *C07K 14/4702* (2013.01); *C07K 14/70503* (2013.01); *G01N 33/5023* (2013.01); *G01N 33/6893* (2013.01); *A23V 2002/00* (2013.01); *A61K 38/00* (2013.01); *G01N 2500/10* (2013.01); *G01N 2800/108* (2013.01)

(58) Field of Classification Search
None
See application file for complete search history.

(56) References Cited

U.S. PATENT DOCUMENTS

2009/0028831 A1* 1/2009 Van Zant ............ A61K 31/095
424/93.7

FOREIGN PATENT DOCUMENTS

| CN | 101821283 A | 9/2010 |
|---|---|---|
| EP | 2036921 A1 * | 3/2009 |
| JP | 2010539123 A | 12/2010 |
| WO | 02081745 A2 | 10/2002 |
| WO | 2012042289 A1 | 4/2012 |

OTHER PUBLICATIONS

Dickinson et al., Reproduction, 2010, vol. 139:697-704.*
Jaworski et al. Collaborative and Specialized Functions of Robo1 and Robo2 in Spinal Commissural Axon Guidance,. The Journal of Neuroscience, Jul. 2010, vol. 30 (28):9445-9453.
International Search Report for PCT/KR2013/005282, (dated Sep. 5, 2013).
Sun et al. "Regulation of osteoblast differentiation by slit2 in osteoblastic cells", Cells Tissues Organs, 2009; 190 (2):69-80 (Abstract).

* cited by examiner

*Primary Examiner* — Xiaozhen Xie
(74) *Attorney, Agent, or Firm* — The PL Law Group, PLLC

(57) ABSTRACT

A pharmaceutical composition for preventing or treating a fracture or osteoporosis, includes, as an active ingredient, a gene selected from a group consisting of slit1, slit2, slit3, robo1, robo2 and vilse, or an expressed protein of the gene. A marker composition for predicting the risk of the occurrence of a fracture or osteoporosis includes the protein. A kit for predicting the risk of the occurrence of a fracture or osteoporosis includes an antibody that specifically binds to the protein. An information provision method for predicting the risk of the occurrence of a fracture or osteoporosis includes measuring the level of expression of the slit protein through an antigen-antibody binding reaction using an antibody that specifically binds to the protein. The slit3 may increase bone formation and decrease bone reabsorption in a cellular and animal model, and has a negative correlation with the incidence rate of osteoporosis.

2 Claims, 21 Drawing Sheets

PBS

Slit3

IL-1β

IL-1β + Slit3

PBS
(Left tibia)

Slit3
(Right tibia)

A

Wild type

Knockout

B

Wild type

Knockout

A. Human osteoblasts

B. Human osteoclasts

COMPOSITION FOR PREVENTING OR TREATING FRACTURE OR OSTEOPOROSIS USING SLIT-ROBO SYSTEM

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2013/005282, filed 14 Jun. 2013, which claims priority to Korean Patent Application No. 10-2012-0064302, filed Jun. 15, 2012, entire contents of which are incorporated herein by reference.

BACKGROUND

Technical Field

The present invention relates to a pharmaceutical composition for preventing or treating a fracture or osteoporosis, which contains, as an active ingredient, the slit or robo gene or a protein expressed by the gene, to a kit for predicting the risk of the occurrence of a fracture or osteoporosis using the gene or the protein expressed by the gene, and to a method of providing information for predicting the risk of the occurrence of a fracture or osteoporosis.

Background Art

Osteoporosis refers to a condition in which bone mineral density has been reduced due to an excessive decrease in the quantity of minerals and substrates that form bones. Osteoporosis makes bones susceptible to a fracture. Accordingly, osteoporosis is the most frequently occurring metabolic bone disease (MBD) that exhibits a low bone mineral density (BMD) and an increased risk of a fracture (Peacock, M., et al., Endocr. Rev. 23: 303-326, 2002; Akhter, M. P., et al., Bone. 41(1): 111-6, 2007). Recently, there has been a rapidly increasing number of patients hospitalized due to general osteoporotic fractures of the hip, the spine and the wrist (Fogarty, P., et al., Maturitas. 52 Suppl 1: S3-6, 2005; Palacios, S., et al., Maturitas. 15; 52 Suppl 1: S53-60. Review, 2005). In particular, osteoporosis frequently develops after menopause in women above the age of 40, and senile osteoporosis occurs in men and women above the age of 70.

Currently, osteoporosis is diagnosed by physical methods, such as X-ray scanning, but such methods disadvantageously require large diagnostic devices and are problematic in terms of safety due to the use of X-rays. In addition, such methods have shortcomings in that they cannot predict further reductions in bone mineral density, and it is difficult to accurately predict the risk of osteoporotic fracture based on bone mineral density alone.

Accordingly, it is necessary to establish a rapid, simple and accurate method that can provide early detection and diagnosis of various types of osteoporosis, such as postmenopausal osteoporosis and senile osteoporosis, and that can predict the risk of a fracture, thus making it possible to effectively treat osteoporosis or a fracture.

Therefore, the present inventors have conducted studies in order to develop an agent for treating a fracture or osteoporosis and to develop a marker for predicting the risk of the occurrence of a fracture or osteoporosis, and, as a result, have found that slit3 increases bone formation and reduces bone resorption in cells and animal models, and has a negative correlation with the incidence of osteoporosis, thereby completing the present invention.

SUMMARY

An object of the present invention is to provide a pharmaceutical composition for preventing or treating a fracture or osteoporosis, the composition containing, as an active ingredient, a gene selected from the group consisting of slit1, slit2, slit3, robo1, robo2 and vilse, or a protein expressed by the genes.

Another object of the present invention is to provide a food composition for preventing or alleviating a fracture or osteoporosis, the composition containing, as an active ingredient, a gene selected from the group consisting of slit1, slit2, slit3, robo1, robo2 and vilse, or a protein expressed by the genes.

Still another object of the present invention is to provide a marker composition for predicting the development of a fracture or osteoporosis, the composition containing, as an active ingredient, a gene selected from the group consisting of slit1, slit2, slit3, robo1, robo2 and vilse.

Still another object of the present invention is to provide a kit for predicting the development of a fracture or osteoporosis, the kit including an antibody that binds specifically to a protein selected from the group consisting of slit1, slit2, slit3, robo1, robo2 and vilse, or an immunogenic fragment thereof.

Still another object of the present invention is to provide a kit for predicting the development of a fracture or osteoporosis, the kit including a primer for RT-PCR for detecting the mRNA of a gene selected from the group consisting of slit1, slit2, slit3, robo1, robo2 and vilse.

Still another object of the present invention is to provide a method of detecting a protein, selected from the group consisting of slit1, slit2, slit3, robo1, robo2 and vilse, in a patient's blood sample through an antigen-antibody reaction in order to provide information required for predicting the development of a fracture or osteoporosis.

Still another object of the present invention is to provide a method for screening an agent for treating a fracture or osteoporosis, the method including comparing the expression levels of slit1, slit2, slit3, robo1, robo2 and vilse proteins in a cell treated with a candidate.

Still another object of the present invention is to provide a recombinant peptide derived from the LRR2 domain of slit3 protein, or a pharmaceutical composition for preventing or treating a fracture or osteoporosis, the pharmaceutical composition containing the recombinant peptide.

Still another object of the present invention is to provide a marker composition for predicting the development of a fracture or osteoporosis, the composition containing a single nucleotide polymorphism located in slit2, slit3, robo1, robo2 or robo4.

In order to accomplish the above objects, the present invention provides a pharmaceutical composition for preventing or treating a fracture or osteoporosis, the composition containing, as an active ingredient, a gene selected from the group consisting of slit1, slit2, slit3, robo1, robo2 and vilse, or a protein expressed by the genes.

The present invention also provides a food composition for preventing or alleviating a fracture or osteoporosis, the composition containing, as an active ingredient, a gene selected from the group consisting of slit1, slit2, slit3, robo1, robo2 and vilse, or a protein expressed by the genes.

The present invention also provides a marker composition for predicting the development of a fracture or osteoporosis, the composition containing, as an active ingredient, a gene selected from the group consisting of slit1, slit2, slit3, robo1, robo2 and vilse.

The present invention also provides a kit for predicting the development of a fracture or osteoporosis, the kit including an antibody that binds specifically to a protein selected from the group consisting of slit1, slit2, slit3, robo1, robo2 and vilse, or an immunogenic fragment thereof.

The present invention also provides a kit for predicting the development of a fracture or osteoporosis, the kit including a primer for RT-PCR for detecting the mRNA of a gene selected from the group consisting of slit1, slit2, slit3, robo1, robo2 and vilse.

The present invention also provides a method of detecting a protein, selected from the group consisting of slit1, slit2, slit3, robo1, robo2 and vilse, in a patient's blood sample by an antigen-antibody reaction in order to provide information required for predicting the development of a fracture or osteoporosis.

The present invention also provides a method for screening an agent for treating a fracture or osteoporosis, the method including comparing the expression levels of slit1, slit2, slit3, robo1, robo2 and vilse proteins in a cell treated with a candidate.

The present invention also provides a recombinant peptide derived from the LRR2 domain of slit3 protein, or a pharmaceutical composition for preventing or treating a fracture or osteoporosis, the pharmaceutical composition containing the recombinant peptide.

The present invention also provides a marker composition for predicting the development of a fracture or osteoporosis, the composition containing a single nucleotide polymorphism located in slit2, slit3, robo1, robo2 or robo4.

The slit or robo protein according to the present invention increases bone formation and reduces bone resorption in cells and animal models, and has a negative correlation with the incidence of osteoporosis. Accordingly, it can be effectively used as a composition for preventing or treating a fracture or osteoporosis or a biomarker for predicting the risk of the occurrence of a fracture or osteoporosis.

DETAILED DESCRIPTION

Figure 1A:
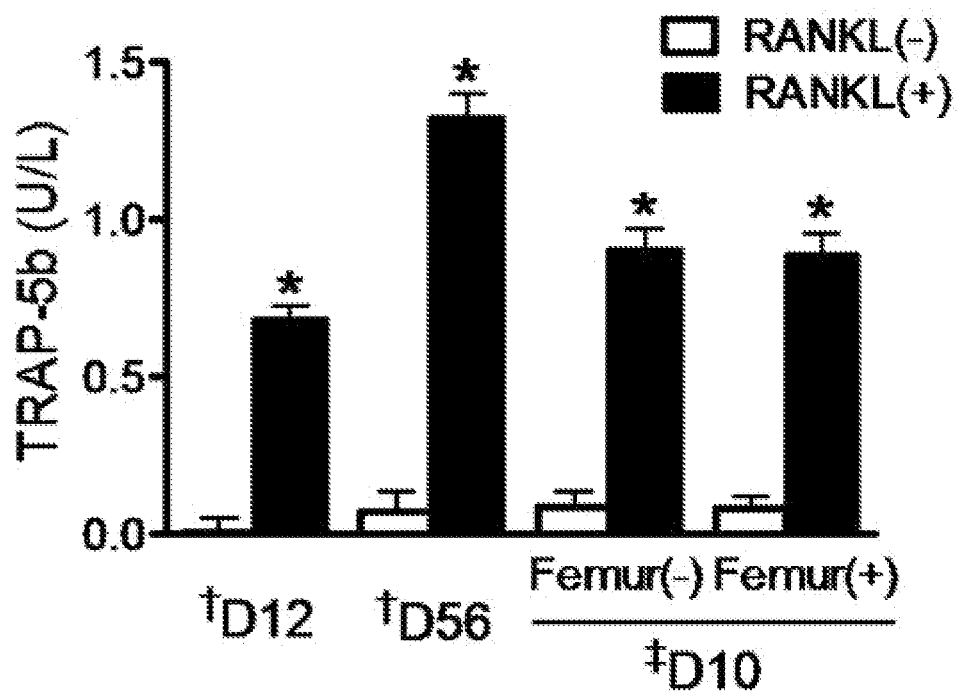
FIGS. 1a and 1b are views illustrating preparing variable culture conditions for osteoclastogenesis and bone resorption in order to establish an in vitro system for investigating a coupling phenomenon.

The present invention will be described in detail below.

The present invention provides a pharmaceutical composition for preventing or treating a fracture or osteoporosis, which contains, as an active ingredient, a gene selected from the following group, or a protein expressed by the gene:

slit1 having a nucleotide sequence encoding an amino acid sequence of SEQ ID NO: 1;

slit2 having a nucleotide sequence encoding an amino acid sequence of SEQ ID NO: 2;

slit3 having a nucleotide sequence encoding an amino acid sequence of SEQ ID NO: 3;

robo1 having a nucleotide sequence encoding an amino acid sequence of SEQ ID NO: 4;

robo2 having a nucleotide sequence encoding an amino acid sequence of SEQ ID NO: 5; and vilse having a nucleotide sequence encoding an amino acid sequence of SEQ ID NO: 6.

In an embodiment of the present invention, the slit1 protein has the amino acid sequence represented by SEQ ID NO: 1; the slit2 protein has the amino acid sequence represented by SEQ ID NO: 2; the slit3 protein has the amino acid sequence represented by SEQ ID NO: 3; the robo1 protein has the amino acid sequence represented by SEQ ID NO: 4; the robo2 protein has the amino acid sequence represented by SEQ ID NO: 5; and the vilse protein has the amino acid sequence represented by SEQ ID NO: 6. The present invention encompasses functional equivalents of the proteins.

The above-described "functional equivalents" refers to proteins that have a sequence homology of at least 70%, preferably at least 80%, more preferably at least 90%, and even more preferably at least 95%, to the amino acid sequences of SEQ ID NOS: 1 to 6 as a result of the addition, substitution or deletion of at least one amino acid, and exhibit substantially the same physiological activity as the proteins represented by SEQ ID NOS: 1 to 6.

The slit1, slit2, slit3, robo1, robo2 or vilse protein of the present invention includes not only a protein having the native amino acid sequence of the protein but also amino acid sequence variants thereof. The "variants of the slit1, slit2, slit3, robo1, robo2 or vilse protein" means proteins having sequences different from that of the native amino acid sequence of the slit1, slit2, slit3, robo1, robo2 or vilse protein as a result of the deletion, insertion, non-conservative or conservative substitution or a combination thereof of one or more amino acid residues. Amino acid exchanges in proteins and peptides which do not generally alter the activity of the proteins or peptides are known in the relevant field of technology (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In some cases, the protein may be modified by phosphorylation, sulfation, acetylation, glycosylation, methylation, farnesylation, or the like.

The slit1, slit2, slit3, robo1, robo2 or vilse protein or its variants may be isolated in nature or synthesized (Merrifield, J. Amer. chem. Soc. 85: 2149-2156, 1963), or may be prepared by a gene recombination method based on DNA sequences (Sambrook et al, Molecular Cloning, Cold Spring Harbour Laboratory Press, New York, USA, 2nd edition, 1989).

In an embodiment of the present invention, the slit1 gene may have a nucleotide sequence of SEQ ID NO: 9.

In an embodiment of the present invention, the slit2 gene may have a nucleotide sequence of SEQ ID NO: 10.

In an embodiment of the present invention, the slit3 gene may have a nucleotide sequence of SEQ ID NO: 11.

In an embodiment of the present invention, the robo1 gene may have a nucleotide sequence of SEQ ID NO: 12.

In an embodiment of the present invention, the robo2 gene may have a nucleotide sequence of SEQ ID NO: 13.

In an embodiment of the present invention, the vilse gene may have a nucleotide sequence of SEQ ID NO: 16.

In a preferred implementation of the present invention, the slit1, slit2, slit3, robo1, robo2 or vilse may be provided not only in the form of a protein but also in the form of a vector that can express the slit1, slit2, slit3, robo1 or robo2 gene in cells, in order for it to be used in gene therapy or vaccines.

The expression vector may be an expression vector known in the relevant field of technology, which can express the slit1, slit2, slit3, robo1, robo2 or vilse gene inserted therein. For example, it may be an expression vector, such as pBK-CMV (Stratagene), pCR3.1 (Invitrogen) or the like.

Moreover, a nucleotide sequence encoding the slit1, slit2, slit3, robo1, robo2 or vilse, that is, a polynucleotide, is administered such that it is expressed in the subject to be treated in the form of a recombinant DNA molecule including the polynucleotide operatively linked to a nucleic acid sequence that controls expression, for example, in the form of an expression vector. Such a vector will thus include appropriate transcriptional control signals including a promoter region capable of expressing the coding sequence, and the promoter is operable in the subject to be treated. Accordingly, for human gene therapy, the promoter, which is a term including not only the sequence necessary to direct RNA polymerase to the transcriptional start site but also, if appropriate, other operating or controlling sequences including enhancers, is preferably a human promoter sequence from a human gene, or from a gene which is typically expressed in humans, such as the promoter from human cytomegalovirus (CMV). Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

The polynucleotide sequence and the transcriptional control sequence may be provided cloned into a replicable plasmid vector, based on commercially available plasmids, such as pBR322, or may be constructed from available plasmids by the routine application of well known, published procedures.

The vector may also include a transcriptional control sequence, located 3' to the gene sequence, and also a polyadenylation sequence, recognizable in the subject to be treated, such as, for example, the corresponding sequences from viruses such as, for human treatment, the SV40 virus. Other transcriptional controlling sequences are well known in the relevant field of technology, and may be used.

The expression vectors may also include selectable markers, such as for antibiotic resistance, which enable the vectors to be propagated.

Expression vectors capable in situ of synthesizing the protein may be introduced into a wound site directly by physical methods. Examples of these methods include topical application of the "naked" nucleic acid vector in an appropriate vehicle, for example, in solution in a pharmaceutically acceptable excipient such as phosphate buffered saline (PBS), or administration of the vector by physical methods such as particle bombardment, also known as "gene gun" technology, according to methods known in the relevant field of technology. In the "gene gun" technology, such as that described in U.S. Pat. No. 5,371,015, inert particles such as gold beads coated with the vector are accelerated at speeds sufficient to enable them to penetrate the surface at the wound site, for example, skin cells, by means of discharge under high pressure from a projecting device.

Other physical methods of administering the DNA directly to the recipient include ultrasound, electrical stimulation, electroporation, and microseeding.

The gene sequence may also be administered to the wound site by means of transformed host cells. Such cells include cells harvested from the subject, into which the nucleic acid sequence is introduced by gene transfer methods known in the relevant field of technology, followed by growth of the transformed cells in culture and grafting to the subject.

Expression constructs, such as those described above, may be used in a variety of ways in the therapy of the present invention. Thus, the expression structures may be directly administered to a site in need of treatment in the subject.

In another embodiment of the present invention, the pharmaceutical composition may contain, as an active ingredient, an activator that increases the expression of slit1, slit2, slit3, robo1, robo2 or vilse.

As used herein, the expression "activator that increases the expression of slit1, slit2, slit3, robo1, robo2 or vilse" means substances that act directly or indirectly on slit1, slit2, slit3, robo1, robo2 or vilse to improve, induce, stimulate or increase the biological activity of slit1, slit2, slit3, robo1, robo2 or vilse. The substances include single compounds such as organic or inorganic compounds, biopolymer compounds such as peptides, proteins, nucleic acids, carbohydrates and lipids, and combinations of a plurality of compounds. The activator that increases the expression of slit3 may be used for the prevention, alleviation or treatment of diseases that are caused by a decrease in the expression, activity or function of slit3. The mechanism by which the activator activates slit1, slit2, slit3, robo1, robo2 or vilse is not specifically limited. For example, the activator can act by a mechanism that increases the expression of gene expression such as transcription or translation or converts an inactive type to an active type. Preferably, the substances that activate slit1, slit2, slit3, robo1, robo2 or vilse are biopolymer compounds such as peptides, proteins, nucleic acids, carbohydrates and lipids. For slit3 whose nucleic acid and protein sequences are known, single compounds such as organic or inorganic compounds, biopolymer compounds such as peptides, proteins, nucleic acids, carbohydrates and lipids, and combinations of a plurality of compounds, which act as inducers or activators, can be prepared or screened by those skilled in the art according to technology known in the relevant field.

Slit3 according to the present invention is secreted from differentiated osteoclasts, functions to increase the migration, viability, proliferation and differentiation of osteoblasts and the production of OPG, increases bone formation, inhibits bone loss, and has an excellent effect of increasing the expression of VEGF contributing to angiogenesis and bone formation. In addition, a decrease in the function and activity of slit3 according to the present invention can lead to a fracture or osteoporosis. Thus, treatment with a gene or protein for stimulating or activating the functions of the gene can be an important clue for the therapeutic approach of a fracture and osteoporosis.

Accordingly, the pharmaceutical composition enables a fracture or osteoporosis to be treated or prevented by administering to a subject an expression vector including the gene or proliferated and activated host cells including the expression vector. The gene or the protein expressed by the gene enables a fracture or osteoporosis to be treated by inhibiting the differentiation of osteoclasts and stimulating the differentiation, proliferation and migration of osteoblasts.

The pharmaceutical composition of the present invention may further contain a suitable carrier, excipient and diluent which are commonly used in the preparation of pharmaceutical compositions. Moreover, it may be formulated in oral dosage forms, including powders, granules, tablets, capsules, suspensions, emulsions, syrup and aerosol, preparations for external application, suppositories, and sterile injectable solutions. Suitable formulations known in the relevant field of technology are disclosed in Remington's Pharmaceutical Science, latest edition, Mack Publishing Company, Easton Pa.). Carriers, excipients and diluents which may be contained in the composition of the present invention include: lactose, dextrose, sucrose, sorbitol, mannitol, xylitol, erythritol, maltitol, starch, *acacia* senegal gum, alginate, gelatin, calcium phosphate, calcium silicate, cellulose, methyl cellulose, microcrystalline cellulose, polyvinyl pyrrolidone, water, methyl hydroxybenzoate, propyl hydroxylbenzoate, talc, magnesium stearate, mineral oil, etc. The composition of the present invention may be formulated with commonly used diluents or excipients, such as fillers, extenders, binders, wetting agents, disintegrants, surfactants, etc. Solid formulations for oral administration include tablets, pills, powders, granules, capsules and the like, and such solid formulations include, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions, and syrup, and may contain various excipients, for example, wetting agents, flavoring agents, aromatics and preservatives, in addition to water and liquid paraffin, which are frequently used simple diluents. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like may be used. As the base of the suppositories, witepsol, Macrogol, Tween 61, cacao butter, laurin fat, glycerogelatin or the like may be used.

As used herein, the term "administering" means providing the composition of the present invention to a subject by any suitable method.

The preferred dose of the pharmaceutical composition of the present invention may vary depending on the patient's condition and weight, the severity of the disease, the dosage form, the route of administration and the time of administration, and can be suitably determined by those skilled in the art. In order to achieve the desired effects, the composition of the present invention may be administered at a daily dose of 0.001 mg/kg to 10000 mg/kg. The composition may be administered in a single dose per day or in multiple doses per day.

The pharmaceutical composition of the present invention may be administered to a subject by various routes. All modes of administration are contemplated, for example, orally, rectally or by intravenous, intramuscular, subcutaneous, intrauterine, intradural or intracerebroventricular injection.

For the prevention or treatment of a fracture or osteoporosis, the composition of the present invention may be used alone or in combination with surgery, radiotherapy, hormone therapy, chemotherapy, and methods that use biological response regulators.

The present invention also provides a food composition for preventing or alleviating a fracture or osteoporosis, which contains, as an active ingredient, a protein selected from the group consisting of slit1, slit2, slit3, robo1, robo2 and vilse.

As used herein, the expression "food composition for preventing or alleviating a fracture or osteoporosis" refers to a food having body modulating functions, including the prevention and alleviation of diseases, host defense, immunity, recuperation and anti-aging, which should be harmless to the human body when it is administered over a long term of period.

The composition of the present invention may be administered to a health functional food for the purpose of preventing or alleviating a fracture or osteoporosis. When the protein according to the present invention or an activator that increases the expression thereof is used as a food additive, it may be added alone or may be used together with other foods or food ingredients, and may be suitably used according to conventional methods. The amount of active ingredient added can be suitably determined depending on the purpose of use (prophylactic, health or therapeutic treatment). When the protein according to the present invention or an activator that increases the expression thereof is used in the preparation of a food or a beverage, it is generally added in an amount of 15 wt % or less, and preferably 10 wt % or less, based on the total weight of the food or beverage. However, when prolonged intake is intended for the purpose of health and hygiene or for health control, the amount of the active ingredient may be smaller than the lower limit of the above-specified range. In addition, even if the active ingredient is used in an amount larger than the upper limit of the above range, it does not cause a problem in terms of safety.

There is no particular limit to the kind of food to which the composition of the present invention may be added. Examples of foods to which the composition of the present invention may be added include meats, sausages, bread, chocolate, candies, snack, confectionery, pizza, noodles, gum, dairy products including ice cream, various soups, beverages, teas, drinks, alcoholic beverages and multi-vitamin preparations.

The health beverage composition of the present invention may additionally contain various sweetening agents or natural carbohydrates as in conventional beverages. The natural carbohydrates include monosaccharides, such as glucose and fructose, disaccharides, such as maltose and sucrose, and natural sweeteners, such as dextrin and cyclodextrin. In addition, synthetic sweeteners, such as saccharin and aspartame, may be used. The content of the natural carbohydrates in the food composition is generally 0.01-10 g, and 0.01-0.1 g, based on 100 g of the composition.

In addition, the composition of the present invention may contain various nutrients, vitamins, electrolytes, flavoring agents, colorants, pectic acid or its salt, alginic acid or its salt, organic acids, protective colloidal thickeners, pH adjusters, stabilizers, preservatives, glycerin, alcohol, carbonating agents used in carbonated drinks, etc. Additionally, the composition of the present invention may contain fruit flesh for the preparation of natural fruit juices, fruit juice beverages and vegetable juices. The content of these additives is not significantly critical, but is generally 0.01-0.1 parts by weight based on 100 parts by weight of the composition.

The present invention also provides a marker composition for predicting the development of a fracture or osteoporosis, which contains a protein selected from the group consisting of slit1, slit2, slit3, robo1, robo2 and vilse.

In an embodiment of the present invention, in order to examine the correlation between the incidence of osteoporosis and the slit3 protein in subjects who can develop osteoporosis, the proteome of the slit3 protein obtained from the blood of the subjects was analyzed. As a result, it was found that the concentration of the slit3 protein in the blood was remarkably high in the group having a high incidence of osteoporosis, and thus slit3 was selected as a protein marker that can be used for the diagnosis or treatment of a fracture or osteoporosis.

The slit3 protein according to the present invention has a negative correlation with the incidence of osteoporosis, and thus can be effectively used as a biomarker for predicting the risk of the occurrence of a fracture or osteoporosis.

As used herein, the term "proteome" refers to the entire complement of proteins that can be expressed by a genome. It has a dynamic concept because the profile of the proteome always changes depending on specific physiological conditions or pathological conditions in a cell or tissue. The term "proteomics" refers to the method and technology that study this proteome, and it means a research field intended to generally understand intracellular modification and network formation in connection with the processes of progression of diseases by studying the properties of proteins with a focus on gene expression, post-translational modification, and binding to other proteins. Because this proteome indicates physiological conditions or pathological conditions in a cell or tissue, it is most suitable as a method for screening diagnostic markers that can be directly used for diagnosis of diseases. In addition, if it is found that the expression of a specific gene is involved in the progression of a disease to promote a fracture or osteoporosis, the protein can be used as a target protein for developing an agent that diagnoses or treat a fracture or osteoporosis by detecting and identifying the presence of the protein. Genomics has advantages of high sensitivity and easy amplification of genes, and thus the development of diagnostic and therapeutic agents based on genomics has been actively pursued, but there is a theoretical problem in that a change in the DNA or mRNA stage cannot lead directly to a change in the protein having activity in cells. Furthermore, in the case of bodily fluids having no genetic material, proteomics is the sole research method. Currently, bodily fluids, such as plasma, serum, urine, cerebrospinal fluid, amniotic fluid or secreting fluid, are being used in diagnosis by a non-invasive approach, and many researchers are introducing proteomics methods in order to screen disease-specific proteins as diagnostic markers.

As used herein, the expression "marker for predicting the development of a fracture or osteoporosis" refers to a protein substance that is used as a standard to distinguish between the blood sample of a group having a high incidence of osteoporosis and the blood sample of a group having a low incidence of osteoporosis. In the present invention, the level of the protein marker is distinctively high or low in the blood of a group having a high incidence of osteoporosis and a group having a low incidence of osteoporosis.

Because the present invention is based on the analysis of the proteomes in the blood of a group having a high incidence of osteoporosis and the blood of a group having a low incidence of osteoporosis, the protein marker may be specific for the development of osteoporosis, and thus can be effectively used for the diagnosis of a fracture or osteoporosis. Furthermore, in view of the fact that the level of the screened protein marker is remarkably high in a group having a high incidence of osteoporosis, the physiological functions of the protein marker may be related directly to the development of osteoporosis, and thus the protein marker can be effectively used as a target protein to investigate the mechanism of development of osteoporosis or develop an agent for treating osteoporosis.

The present invention also provides a kit for predicting the development of a fracture or osteoporosis, which includes an antibody that binds specifically to a protein selected from the group consisting of slit1, slit2, slit3, robo1, robo2 and vilse, or an immunogenic fragment thereof.

As used herein, the term "antibody" refers to a specific protein molecule that is directed against an antigenic site. For the purpose of the present invention, the term "antibody" means an antibody that binds specifically to a marker protein, and is intended to all polyclonal antibodies, monoclonal antibodies and recombinant antibodies.

Because the marker protein for predicting the risk of the occurrence of a fracture or osteoporosis was identified as described above, an antibody against the marker protein can be easily produced using technology widely known in the relevant field of technology.

A polyclonal antibody can be produced according to a method widely known in the relevant field of technology by injecting the marker protein antigen for predicting the risk of the occurrence of a fracture or osteoporosis into an animal, collecting blood from the animal, and isolating serum containing the antibody from the blood. The polyclonal antibody may be produced from any animal species hosts such as goats, rabbits, sheep, monkeys, horses, pigs, cattle, dogs, etc. The monoclonal antibody may be produced by any methods well known in the relevant field of technology such as a hybridoma method (see Kohler and Milstein (1976), European Journal of Immunology 6: 511-519) or a phage antibody library technology (Clackson et al., Nature, 352: 624-628, 1991; Marks et al, J. Mol. Biol., 222:58, 1-597, 1991). The antibody produced by the above method may be isolation and purified using a method such as gel electrophoresis, dialysis, salt precipitation, ion exchange chromatography, affinity chromatography or the like.

The antibody of the present invention includes functional fragments of the antibody molecule, as well as a complete form having two full-length light chains and two full-length heavy chains. "Functional fragments of the antibody molecule" means fragments having at least an antigen-binding function, including Fab, F(ab'), F(ab')2, Fv, etc.

The kit of the present invention includes at least one composition suitable for an analytic method, a solution or a device.

For example, the kit of the present invention may be a kit that includes an element essential for performing an enzyme-linked immunosorbent assay (ELISA). The ELISA kit may include an antibody specific for a marker protein, and an agent that can be used to measure the level of the protein. The ELISA kit may include a reagent that can detect an antibody that formed an antigen-antibody complex, for example, a labeled secondary antibody, chromophores, an enzyme (e.g., an enzyme conjugated to antibody), and a substance of the enzyme. Further, it may include an antibody specific for a quantitative control group protein.

Further, the kit of the present invention may be a kit that includes the essential elements needed to perform polymerase chain reactions (PCR). These elements include a kit that includes genomic DNA derived from a sample to be analyzed, a primer set specific for the marker of the present invention, proper amounts of DNA polymerase (for example, Taq-polymerase), deoxynucleotides (dNTP) mixture, PCR buffer, and water. The PCR buffer may include KCl, Tris-HCl, and $MgCl_2$. In addition, the kit of the present invention may include an element needed to perform the electrophoresis that is used to check the amplification of the PCR product.

Further, the kit of the present invention may be a kit that includes the essential elements needed to perform reverse transcription polymerase chain reaction (RT-PCR). The RT-PCR kit may include marker gene-specific primer pairs and may also include test tubes or other appropriate containers, reaction buffer solution (with varying pH and magnesium concentration), dNTPs, enzymes such as Taq-polymerase and reverse transcriptase, DNase, RNase inhibitor, DEPC-water, and sterile water etc. Further, it may include a primer pair for a gene that serves as a quantitative control group.

Further, the kit of the present invention may be a kit that includes an essential element needed to perform DNA chip analysis. The DNA chip kit may include a substrate to which a gene or cDNA that corresponds to a fragment of the gene is attached as a probe. The substrate may also have a quantitative structural gene or cDNA that corresponds to a fragment of the quantitative structural gene.

Further, the kit of the present invention may be a microarray kit including a substrate having immobilized thereon the marker of the present invention.

The present invention also provides a method of detecting a protein, selected from the group consisting of slit1, slit2, slit3, robo1, robo2 and vilse, in a patient's blood sample by an antigen-antibody reaction in order to provide information required for prediction of a fracture or osteoporosis.

In the present invention, "detecting a protein" may be performed by measuring the expression level of mRNA or protein.

The "measuring the expression level of mRNA" refers to a process that determines the presence or absence and level of an mRNA encoding the protein in a biological sample in order to predict the risk of the occurrence of a fracture or osteoporosis. An analysis method for this measurement may be any method known in the relevant field of technology, and examples thereof include, but are not limited to, PCR, RT-PCR, competitive RT-PCR, Real-time RT-PCR, RNase protection assay (RPA), Northern blotting, and DNA chip technology.

In the present invention, the "measuring the expression level of a protein" refers to a process that determines the presence or absence of the protein and expression level of the protein in a biological sample in order to predict the risk of the occurrence of a fracture or osteoporosis. Preferably, it can be performed by measuring the level of the protein of the gene using an antibody that binds specifically to the protein. An analysis method for this measurement may be any method known in the relevant field of technology, and examples thereof include, but are not limited to, Western blotting, enzyme-linked immunosorbent assay (ELISA), radioimmunoassay (RIA), radioimmunodiffusion, ouchterlony immunodiffusion, rocket electrophoresis, immunohistological staining, immunoprecipitation assay, complement fixation assay, fluorescence activated cell sorter (FACS), and protein chip technology.

According to a preferred embodiment of the present invention, slit3 can be effectively used as a biomarker for predicting the risk of the occurrence of a fracture or osteoporosis, because it has a negative correlation with the incidence of osteoporosis.

The present invention also provides a method for screening an agent for treating a fracture or osteoporosis, the method including the steps of: (a) culturing a cell having introduced therein a gene selected from the group consisting of slit1, slit2, slit3, robo1, robo2 and vilse; (b) bringing a candidate into contact with the cell of step (a); and (c) comparing the expression level of the slit1, slit2, slit3, robo1, robo2 or vilse protein in the cell of step (b) with that of a control group not treated with the candidate.

The present invention also provides a recombinant peptide having an amino acid sequence represented by SEQ ID NO: 17 and derived from the LRR2 domain of slit3 protein, and a pharmaceutical composition for preventing or treating a fracture or osteoporosis, which includes the recombinant peptide.

Figure 13:
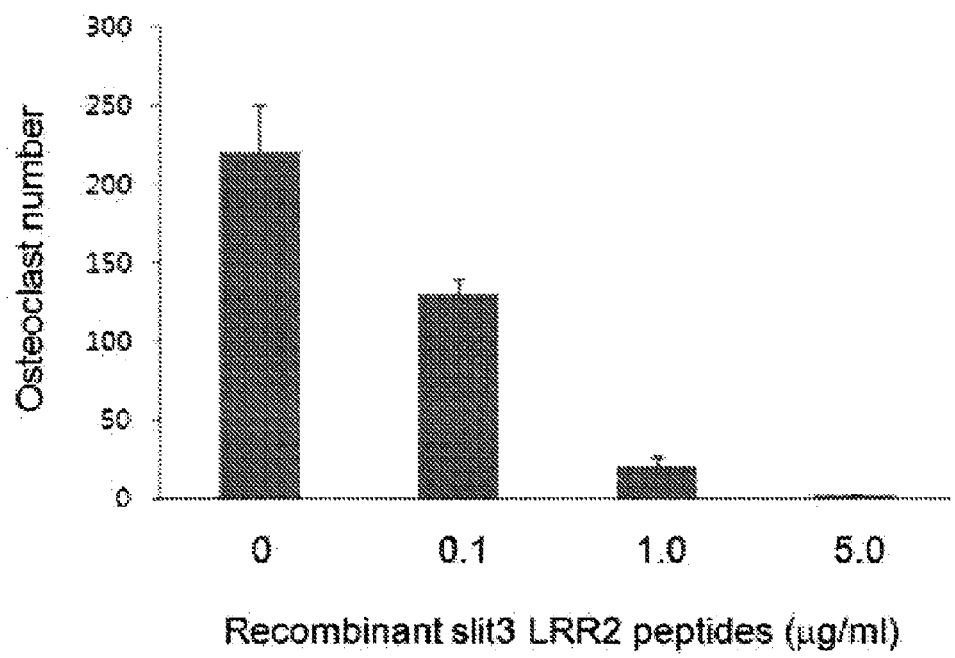
FIG. 13 is a view illustrating that a recombinant peptide derived from the LRR2 domain inhibits the differentiation of osteoclasts.

The LRR2 domain of the slit3 protein is one of four leucine-rich repeat (LRR) domains present in the slit protein, and the second domain LRR2 of the four domains binds to the receptor. The present inventors prepared a small recombinant peptide of slit3 from the LRR2 domain, and then examined the effect of the recombinant peptide on the differentiation of osteoclasts. As a result, it was found that the recombinant peptide significantly inhibited the differentiation of osteoclasts (FIG. 13). Thus, the recombinant peptide can be effectively used for the treatment of osteoporosis.

The present invention also provides a polynucleotide for predicting the development of a fracture or osteoporosis, which includes at least 10 contiguous nucleotides including a nucleotide at an SNP position selected from the following group, or a complementary polynucleotide thereof:

NCBI refSNP ID: rs7655084 for a polynucleotide having a nucleotide sequence of SEQ ID NO: 10;

NCBI refSNP ID: rs1549909 for a polynucleotide having a nucleotide sequence of SEQ ID NO: 11;

NCBI refSNP ID: rs10036727 for a polynucleotide having a nucleotide sequence of SEQ ID NO: 11;
NCBI refSNP ID: rs3821735 for a polynucleotide having a nucleotide sequence of SEQ ID NO: 13;
NCBI refSNP ID: rs78817248 for a polynucleotide having a nucleotide sequence of SEQ ID NO: 13; and
NCBI refSNP ID: rs12418548 for a polynucleotide having a nucleotide sequence of SEQ ID NO: 15.

The NCBI refSNP ID for the SNP indicates the sequence and position of the SNP. Any person skilled in the art can easily find the position and sequence of the SNP. The reference sequences used in the analysis were compiled and issued by the Genome Reference Consortium on February 2009, and are currently available in GRCh37(hg19) of the NCBI assembly database (genome.ucsc.edu/cgi-bin/hgGateway). It will be obvious to those skilled in the art that specific sequences corresponding to the SNP refSNP ID registered in the NCBI can be slightly changed based on future research results, and this changed sequence also falls within the scope of the present invention.

According to an embodiment of the present invention, RefSNP ID: rs7655084 contains a T-to-G substitution at chromosome 4 (position 20255306) of SLIT2 gene, and the genotype at the position shows low bone mineral density. RefSNP ID: rs1549909 has a C-to-G substitution at chromosome 5 (position 168180670) of SLIT3 gene, and the genotype at the position shows low bone mineral density. RefSNP ID: rs10036727 contains a C-to-T substitution at chromosome 5 (position 168180081) of SLIT3 gene, and the genotype at the position shows low bone mineral density. RefSNP ID: rs3821735 contains a C-to-A substitution at chromosome 3 (position 77684222) of ROBO2 gene, and the genotype at the position shows low bone mineral density. RefSNP ID: rs78817248 contains a C-to-G substitution at chromosome (position 77626788) of ROBO2 gene, and the genotype at the position shows low bone mineral density. RefSNP ID: rs12418548 contains an A-to-G substitution at chromosome 11 (position 124757560) of ROBO4 gene, and the genotype at the position shows low bone mineral density.

As can be seen from the Examples below, polymorphism in the genes was investigated in a group having a bone mineral density (BMD) higher than the normal value (supernormal BMD group) and a BMD group having a severely low bone mineral density (severe-low BMD group), and as a result, it was found that an allele at the SNP of the genes had a significant correlation with the risk of severely low BMD (see Table 6). Specifically, it was found that the SNP genotypes showing the risk of low BMD were GT and GG in refSNP ID: rs7655084; a TT genotype in refSNP ID: rs1549909; a TT genotype in refSNP ID: rs10036727; CC and CT genotypes in refSNP ID: rs3821735; ref SNP ID: CG and GG genotypes in rs78817248; and GG and GA genotypes in ref SNP ID: rs12418548.

Thus, the SNPs according to the present invention can be effectively used to predict the development of a fracture or osteoporosis resulting from a severely low bone density.

In the present invention, the polynucleotide including the SNP, or a complementary polynucleotide thereof, may be a DNA fragment including at least 10 contiguous nucleotides. The length of the DNA fragment may be any size including the nucleotides of the SNP, as long as it is not the full length of the gene. However, the length of the DNA fragment is preferably 10 to several hundred nucleotides, and more preferably 100-500 nucleotides. When the DNA fragment has a length of 100-500 nucleotides, it can be used as a probe or primer for detecting the SNP, and when it has a length of more than 500 nucleotides, it can be used for PCR-RFLP and the like.

The present invention also provides a marker composition or kit for predicting the development of a fracture or osteoporosis, which includes the polynucleotide including the SNP, or a complementary polynucleotide thereof.

In the present invention, the kit including the SNP can be prepared by a SNP kit preparation method known in the relevant field of technology. For example, if the kit is provided as a microarray, an SNP can be easily detected by immobilizing the polynucleotide including the SNP or a complementary polynucleotide thereof on a substrate, hybridizing nucleic acids on the microarray, and detecting the result of the hybridization.

The polynucleotide including the SNP or a complementary polynucleotide thereof can be easily immobilized on a substrate according to any method known in the relevant field of technology. In addition, nucleic acid hybridization on the microarray and detection of the hybridization result can also be carried out according to any method known in the relevant field of technology. For example, the hybridization result can be detected by labeling a nucleic acid sample with a label (e.g., fluorescent substance) that generates a detectable signal, and detecting a signal generated from the label.

Hereinafter, the present invention will be described in further detail with reference to examples. It will be obvious skilled in the art that these examples are for illustrative purposes and are not intended to limit the scope of the present invention.

EXAMPLES

Materials and Reagents

An antibody against NFATc1 was purchased from Santa Cruz Biotechnology (Santa Cruz, Calif., USA). An antibody against slit3, and recombinant slit1/2/3, were purchased from Abcam (Cambridge, Mass., USA) and R&D System Inc. (Minneapolis, Minn., USA), respectively. Robo1 and Robo2 fc chimeras were purchased from R&D system Inc.

Example 1

Cell Culture, Organ Culture, and Collection of Conditioned Media

Primary bone marrow cells (BMCs) were obtained by flushing the femur and tibia of 5-6-week-old C57BL/6 mice, and then cultured in a minimal essential medium ($\alpha$-MEM; Wel Gene, Daegu, Korea) containing 10% FBS (Gibco, Grand Island, N.Y., USA), 100 U/mL penicillin and 100 μg/mL streptomycin at 37° C. under a condition of 5% $CO_2$. After 24 hours of culture, non-adherent cells were collected, and cultured in a 48-well plate at a density of $1.0 \times 10^5$ cells/well. The BMCs cultured with 30 ng/mL M-CSF (R&D System Inc.) for 3 days or more were used as bone marrow macrophages (BMMs). The cells of this stage were regarded as osteoclast precursors. The BMCs were cultured with 30 ng/mL M-CSF and 50 ng/mL soluble RANKL (R&D System Inc.) while the medium was replaced at intervals of 2-3 days, thereby inducing the differentiation of the BMCs into osteoclasts. Meanwhile, murine macrophage Raw 264.7 cells (ATCC, Manassas, Va., USA) were also cultured with the same amount of RANKL to prepare osteoclast-like cells.

For a co-immunoprecipitation experiment on human osteoclasts, peripheral blood was obtained from normal healthy volunteers. The blood was diluted with the same amount of α-MEM, and then peripheral blood mononuclear cells (PBMCs) were separated by density gradient centrifugation in Lymphoprep™ (Axis-Shield, Oslo, Norway). The cells were suspended in autoMacs buffer, and CD14-positive mononuclear cells were separated using autoMacs magnetic cell separator; Miltenyi Biotech (Auburn, Calif., USA). The PBMCs ($3.0-4.0 \times 10^6$/well) were cultured in a 6-well plate in the presence of M-CSF (25 ng/mL) for 3 days, and then additionally cultured with M-CSF (25 ng/mL) and RANKL (30 ng/ml). The complete differentiation of the cells into osteoclasts required a time of 7-9 days.

Primary mouse osteoclasts were isolated by sequential collagenase digestion of calvaria obtained from neonatal C57BL/6 mice, and were maintained in 10% FBS-containing α-MEM. The mouse MC3T3-E1 preosteoblast cell line (ATCC) was cultured in α-MEM (containing 10% FBS, 100 U/mL penicillin, and 100 µg/mL streptomycin) at 37° C. under a condition of 5% $CO_2$. The medium was replaced twice a week. After reaching a confluence of 80%, the cells were subcultured with trypsin-EDTA (Gibco). For a co-immunoprecipitation experiment on human osteoblasts, primary bone marrow stromal cells (BMSCs) were isolated from ribs. Ribs are discarded upon thoracotomy of patients having no metabolic bone disease. The ribs were excised in an aseptic state, and the tissue was made clean, and then opened longitudinally. The exposed bone marrow was flushed out by washing it several times with serum-free α-MEM, followed by centrifugation at 1,400 rpm for 10 minutes. The cell pellets were re-suspended in medium, and a human BMSC fraction was isolated by Lymphoprep™ (Axis-Shield, Oslo, Norway). The cells were seeded into a 75-cm$^2$ plastic culture flask at a density of $3 \times 10^7$ cells/75-cm$^2$, and cultured in α-MEM containing 10% FBS, 100 U/mL penicillin and 100 µg/mL streptomycin. The medium was replaced twice a week after 2 weeks. When the cells reached to a confluence of 80-90%, the cells were subcultured with 0.01% trypsin and 0.05% EDTA. The cells at passage 2 were used in the experiment.

The organ culture of the femur obtained from 6-week old C57BL/6 mice was performed. The bone marrow was strongly flushed, and cells were further removed by shake culture with $H_2O$ for 24 hours. Then, the bone was extensively washed with α-MEM, and co-cultured with BMMs.

During osteoclastogenesis or bone resorption, conditioned medium (CM) was collected at the indicated date for 24 hours. The collected CM was filtered through a 0.45-µm membrane filter, and stored at −70° C. until use.

Example 2

Measurement of Osteoclastogenesis and Resorption Activity in CM

The degree of osteoclastogenesis in the CM collected at various stages of osteoclastogenesis was assessed by measuring TRAP-5b (tartrate-resistant acid phosphatase-5b) using an ELISA kit (Immunodiagnostic Systems, Boldon, UK) having a minimal detection threshold of 0.2 U/L according to the manufacturer's instruction. Resorption activity in the CM was assessed by measuring CTX (C-telopeptide) using an ELISA kit (RatLaps; Immunodiagnostic Systems) having a minimal detection threshold of 2.0 ng/mL.

Example 3

Analysis of Chemotaxis and Wound Healing

The analysis of chemotaxis was performed in a Boyden chamber system using a transwell with a polycarbonate membrane including 8-µm pores (Costar, Corning, N.Y., USA). Cells were seeded into the inner chamber at a density of $1.0 \times 10^5$ cells per 100 µL of 0.1% FBS-containing α-MEM 100 µL, and then treated with CM or slit3 in the outer chamber for 24 hours. Cells on the upper membrane were completely removed with a cotton swab. The cells that penetrated the lower membrane were fixed, and stained with hematoxylin. The cells were counted using a computer video-imaging system (Olympus, Tokyo, Japan).

For the analysis of wound healing, confluent cells were wounded with a plastic tip. After cell migration occurred in 0.10 FBS-containing α-MEM, the wound was marked, and measured with an inverted microscope at 0 hour and 24 hours. Quantification was performed by measuring each wound closure area using Quantity One (BioRad, Hercules, Calif., USA). Data were expressed as the percent of wound closure.

Example 4

Measurement of Cell Viability and Differentiation

Cell viability was measures using a cell counting kit (CCK-8; Dojindo, Kumamoto, Japan) according to the manufacturer's instruction. Briefly, 10 µL of WST-8 dye (2-[2-methoxy-4-nitrophenyl]-3-[4-nitrophenyl]-5-[2,4-disulfophenyl]-2H-tetrazolium, monosodium salt) was added to each well of a 96-well plate and allowed to react for 2 hours, and then the absorbance at 450 nm was measured with a reference wavelength of 650 nm using a microplate reader (SPECTRAmax 340PC; Molecular Devices, Palo Alto, Calif., USA).

Cell differentiation was measured using Brd-U (5-bromo-2'-deoxyuridine). Osteoblasts were seeded into a 96-well plate and incubated for 24 hours, followed by subculture in α-MEM for 24 hours. Then, the cells were reacted with Brd-U for 24 hours, after which the cell differentiation was measured with a Brd-U labeling and detection kit (Roche, Mannheim, Germany).

Example 5

Proteomics Protocol

Sample Preparation

Raw 264.7 cells were seeded in 10% FBS-containing α-MEM at a density of $4.0 \times 10^5$ cells per 100-mm dish, and then treated in the presence or absence of 50 ng/mL soluble RANKL to allow them to differentiate into osteoclasts. On the next day, the cells were washed with a serum-free and phenol red-free medium, after which the medium was replaced with 6 mL of a serum-free and phenol red-free medium with or without RANKL, and the cells were cultured for one day. The CM was filtered through a 0.45-µm membrane e filter and stored at −70° C. Protein in the CM was precipitated by freeze drying.

Fractionation by C18 Reverse-Phase HPLC and Trypsin Digestion

A protein complex was separated into 96 fractions using a capillary HPLC system (equipped with a C18-HPLC column (214TP5125, 2.1×150 mm; Vydac Grace, Hesperia, Calif., USA), an auto-sampler and a UV detector (215 nm wavelength; Peptide Library Support Facility, Pohang, Korea) with 0-60% gradient CAN (acetonitrile) and 0.1% TFA (trifluoroacetic acid) at a flow rate of 0.3 mL/min for 120 minutes.

For trypsin digestion, each protein fraction was dissolved in 50 mM ABC (ammonium bicarbonate), and then the sample was reduced by adding 10 mM DTT (dithiothreitol) thereto. For cysteine alkylation, 100 mM iodoacetamide was added thereto. Finally, 500 ng of trypsin was added thereto and allowed to react at 37° C. for 6 hours.

LC-MS/MS Analysis

Each digested sample was analyzed using a LTQ (linear-trap quadrupole) mass spectrometer equipped with a nano-flow HPLC system (Thermo Fisher Scientific, San Jose, Calif., USA). Peptides were separated using a reverse-phase analysis column (10 cm×75 μm i.d.) packed with C18 (3 μm). The gradient was started at 5% ACN for 5 minutes at a flow rate of 250 nL/minute, and then increased to 40% ACN for 60 minutes, and finally 80% ACN for 10 minutes. The eluent was injected into the LTQ mass spectrometer using a nano-ion source at an electrospray voltage of 1.8 kV. The analysis process consisted of full mass spectrometry (MS) scanning in the range of 400-1500 m/z, and data-dependent mass spectrometry for five most intense ions was analyzed in the full MS scan.

MASCOT Database Search

Data acquired from a TQ mass spectrometer were analyzed using the international protein index (IPI) mouse FASTA database (version 3.54) and the MASCOT search engine. Incomplete cleavages following trypsin digestion, variable modification of the oxidation of methionine, and carbamidomethylation of cysteine as a fixed modification were considered during the search process. The present inventors validated the individual ions with a confidence range of 95% probability (P<0.05).

Functional Annotation and Secretory Protein Selection

For functional annotation, identified proteins were classified according to their biological process and molecular function using the DAVID (database for Annotation, Visualization, and Integrated Discovery) database that is the web-based program (david.abcc.ncifcrf.gov). Also, the properties of the identified proteins were assessed using SignalP 3.0 hidden Markov matrix scoring.

Example 6

Western Blotting

A cell lysate was prepared with lysis buffer (20 mM Tris [pH 7.5], 150 mM NaCl, 1 mM EDTA, 1% Triton X-100, 2.5 mM sodium pyrophosphate, 1 mM-glycerophosphate, 1 mM Na3VO4, 1 mM NaF, and a protease-inhibitor mixture) at 4° C. for 20 minutes. The protein concentration of the lysate was measured using a BCA protein assay kit (Pierce Chemical Co., Rockford, Ill., USA). A sample containing 10-20 μg of protein was separated by 10% gel SDS-PAGE, and then transferred to a nitrocellulose membrane (Amersham Biosciences, Buckinghamshire, UK). The membrane was blocked with 5% skim milk in TBST (500 mM Tris-HCL [pH 7.4], 1.5 M NaCl, 0.1% Tween-20) at room temperature for 1 hour, and then reacted with primary antibody, followed by reaction with secondary antibody. Immunoreactive proteins were detected using an enhanced chemiluminescence kit (PerkinElmer, Waltham, Mass., USA).

Examples 7

Co-Immunoprecipitation

The human cDNAs of GFP-tagged Robo1 and Myc-tagged Vilse were purchased from Origene (Rockville, Md., USA). The cDNAs of Robo1-GFP and Vilse-Myc were transfected into human BMSCs or human PBMCs for 6 hours by lipofectamine 2000 (Gibco, Grand Island, N.Y., USA), and then the cells were treated with Slit3. The cells were lysed with a THE buffer (25 mM Tris-HCl, pH 7.4, 150 mM NaCl, 1% Triton X-100, 1 mM EDTA) containing a protease inhibitor cocktail (Sigma-Aldrich, St. Louis, Mo., USA) and phosphatase inhibitors (1 mM Na3VO4, 1 mM NaF). The lysate was immunoprecipitated with GFP antibody (Anaspec, Fremont, Calif., USA) and protein-G-Sepharose beads (Amersham Biosciences, Buckinghamshire, UK) at 4° C. for 18 hours. The immuneprecipitate and the cell lysate were provided for immunoblot analysis with anti-GFP or anti-Myc antibody (Novus biological, Littleton, Co, USA).

Example 8

RT-PCR and Quantitative Real-Time PCR

Total RNA was isolated using TRIzol reagent (Invitrogen, Rockville, Md., USA) according to the manufacturer's instruction, and cDNA was synthesized from 1 μg of the total RNA using a Superscript III First-Strand Synthesis System (Invitrogen). All PCR amplifications were performed using a Biometra thermocycler (GmbH, Goettingen, Germany). The mRNA expression level of each target gene was normalized with the housekeeping gene GAPDH (glyceraldehydes-3-phosphate dehydrogenase) using Quantity One program. Specific primer pairs are as follows: 5'-AGG GAA GCC TAC GCA GAT G-3' (SEQ ID NO: 18) (sense) and 5'-TGG ACA GTG GGC GAT TTT AT-3' (SEQ ID NO: 19) (antisense) for Robo1; 5'-AGC CCC ACA CAA ACA AGG-3' (SEQ ID NO: 20) (sense) and 5'-AAG CTG GGC TTG CTG TAG G-3' (SEQ ID NO: 21) (antisense) for Robo2; 5'-GCA GCG CTC AAC CCT AGT-3' (SEQ ID NO: 22) (sense) and 5'-CTT CTG GCC CAA CTC TTG AC-3' (SEQ ID NO: 23) (antisense) for Robo3; 5'-CGC ATG TCT CTG ACC CCT AC-3' (SEQ ID NO: 24) (sense) and 5'-GAG CTG TTA GCT TGG TGC AA-3' (SEQ ID NO: 25) (antisense) for Robo4; and 5'-ACT TTG TCA AGC TCA TTT CC-3' (SEQ ID NO: 26) (sense) and 5'-TGC AGC GAA CTT TAT TGA TG-3' (SEQ ID NO: 27) (antisense) for GAPDH. The amplification protocol consisted of 30 cycles, each consisting of denaturation at 95° C. for 30 sec, annealing at 60° C. for 30 sec and extension at 72° C. for 30 sec. The PCR products were separated on 1% agarose gel, stained with EtBr, and visualized under UV.

Quantitative PCR was performed using Light Cycler 480 (Roche). The gene expression levels of OPG (osteoprotegerin), RANKL, ALP (alkaline phosphatase), OCN (osteocalcin), TRAP, CatK (cathepsin K), MMP-9 (matrix metallopeptidase-9) and CTR (calcitonin receptor) were measured using Light Cycler 480 SYBR Green I Master Mix (Roche). PCR amplification was performed in duplicate, and water as a negative control was used in place of cDNA in each run. Specific primer sequence pairs are as follows: 5'-CAC GGC CAT CCT ATA TGG TAA-3' (SEQ ID NO: 28) (sense) and 5'-GAG ACA TTT TCC CGT TCA CC-3 (SEQ ID NO: 29) for ALP; 5'-GCT ACC TTG GAG CCT CAG TC-3' (SEQ ID NO: 30) (sense) and 5'-CTC GTC ACA AGC AGG GTT AAG-3' (SEQ ID NO: 31) (antisense) for OCN; 5'-GCA TTA TGA CCC AGA AAC TGG T-3' (SEQ ID NO: 32) (sense) and 5'-TAG GTG CCA GGA GCA CAT TT-3' (SEQ ID NO: 33) (antisense) for OPG; 5'-AGC GCA GAT GGA TCC TAA CA-3' (SEQ ID NO: 34) (sense) and 5'-GAG TCC TGC AAA TCT GCG TT-3' (SEQ ID NO: 35) (antisense) for RANKL; 5'-CGA CCA TTG TTA GCC ACA TAC G-3' (SEQ ID NO: 36) (sense) and 5'-TCG TCC TGA AGA TAC TGC AGG TT-3' (SEQ ID NO: 37) (antisense) for TRAP; 5'-ATA TGT GGG CCA GGA TGA AAG TT-3' (SEQ ID NO: 38) (sense) and 5'-TCG TTC CCC ACA GGA ATC TCT-3' (SEQ ID NO: 39) (antisense) for CatK; 5'-TGT CTG GAG ATT CGA CTT GAA GTC-3' (SEQ ID NO: 40) (sense) and 5'-TGA GTT CCA GGG CAC ACC A-3' (SEQ ID NO: 41) (antisense) for MMP-9; 5'-AGT TGC CCT CTT ATG AAG GAG AAG-3' (SEQ ID NO: 42) (sense) and 5'-GGA GTG TCG TCC CAG CAC AT-3' (SEQ ID NO: 43) (antisense) for CTR; and 5'-CTC CAC TCA CGG CAA ATT CA-3' (SEQ ID NO: 44) (sense) and 5'-GCC TCA CCC CAT TTG ATG TT-3' (SEQ ID NO: 45) (antisense) for GAPDH. In order to activate FastStart DNA polymerase, the reaction protocol included predenaturation at 95° C. for 10 min, and 45 cycles, each consisting of 95° C. for 10 min, 55° C. for 15 sec and 72° C. for 20 sec. The results were normalized with GAPDH.

Example 9

Transfection with siRNA siRNA and nonsense siRNA (Stealth RNAi™ siRNA negative control; Invitrogen) for each of NFATc1 (MmNFATc1_6; Qiagen), Robo1 (MSS208673; Invitrogen) and Robo2 (MSS241005; Invitrogen) were transfected by lipofectamine reagent (Invitrogen) according to the manufacturer's instruction. Briefly, cells were cultured in 10% FBS-containing α-MEM, and then a siRNA-reagent mixture in OPTI-MEM (Invitrogen) was added to the cells, which were further cultured for additional 6 hours. Next, the medium was replaced with fresh complete α-MEM, and then the cells were further cultured for 2 days.

Example 10

Examination of Lamellipodia

MC3T3-E1 cells were seeded in a 24-well plate for 24 hours, and then starved in the presence or absence of slit3. The cells were fixed and washed twice with PBS (phosphate-buffered serum). The cells were incubated with 100 ng/mL of phalloidin (Molecular Probes, Leiden, Netherlands) at 37° C. for 30 minutes. Immunofluorescence images were captured with a fluorescence microscope (Olympus).

Example 11

Formation of Calcified Nodules

Primary mouse BMCs were seeded in a 12-well plate at a density of $6\times10^6$ cells/well, and cultured in an incubator with α-MEM (supplemented with 10% FBS (v/v), 100 U/mL penicillin and 100 mg/L streptomycin) at 37° C. for 7 days under the condition of 5% $CO_2$ and 95% air. After 7 days, non-adherent cells were removed, and then adherent cells showing BMSCs (bone marrow stromal cells) were allowed to grow up to day 14 in a differentiation medium (α-MEM containing 10% FBS [v/v] supplemented with 8 mM β-glycerophosphate and 50 μg/mL ascorbic acid) for inducing the differentiation of BMSCs into osteoblasts. The medium was replaced at intervals of 2 or 3 days. On day 14, the culture was fixed with 70% ethanol for 1 hour, and then stained with 40 mM Alizarin red S (Sigma-Aldrich, St. Louis, Mo., USA).

Example 12

TRAP Staining and Resorption Analysis

Primary mouse BMCs were cultured with 30 ng/mL of M-CSF and 50 ng/mL of soluble RANKL for 4 days. Adherent cells were fixed, and stained with the enzymatic marker TRAP using a leukocyte acid phosphatase kit (Sigma-Aldrich) according to the manufacturer's instruction. TRAP-positive multinucleated cells containing at least 3 nuclei were regarded as osteoclasts, and counted under an optical microscope (Olympus).

For measurement of a resorption area, BMCs ($5\times10^4$ cells/well) were placed on dentine discs together with 30 ng/mL of M-CSF and 50 ng/mL of soluble RANKL. After 10 days, the slide was washed with a 5% aqueous solution of sodium hypochlorite to remove cells, and then the resorption pits were stained with hematoxylin. For measurement of a resorbed area per number of BMCs, TRAP staining was performed before hematoxylin staining on dentine discs. The area of the resorption pits was analyzed using Quantity One Software (VersaDoc Model 3000 Imaging system, Bio-Rad, Berkeley, Calif., USA).

Example 13

In Vivo Calvarial Bone Formation Model

PBS or 300 μg/kg of slit3 was injected subcutaneously into the calvaria of 4-week-old C57BL/6 mice once a day, five times a week for 3 weeks. The injection was performed into the left side of the calvarial sagittal between the lambdoidal suture and the coronal suture, and the right side was used as a control. The animals were sacrificed, and the calvaria were fixed in 4% PFA (paraformaldehyde). Each calvarium was decalcified in 14% EDTA, and was embedded in an OCT (optical cutting temperature) compound for frozen sectioning. The samples were cut into 7 μm sections, and then stained with hematoxylin and eosin. The width of the calvarial bone was measured with an optical microscope.

Example 14

In Vivo Calvarial Bone Loss Model 6-week-old C57BL/6 mice were divided into the following four groups: a control group (0.1% BSA+PBS); a slit3-treated group (0.1% BSA+300 μg/kg slit3); an IL-1-induced calvarial bone loss group (2 μg IL-1+PBS); and an IL-1 calvarial bone loss and slit3-treated group (2 μg IL-1+ 300 μg/kg slit3). The solution-treated collagen sponge (Cellmatrix Type I-A; Nitta Gelatin Inc., Osaka, Japan) was transplanted into the calvariaum in the center of the sagittal suture. After 7 days, the mice were sacrificed, and the calvaria were fixed in 4% PFA. Each calvarium was decalcified in 14% EDTA, and embedded in an OCT compound for frozen sectioning. The samples were cut into 7 μm sections, and then stained with hematoxylin and eosin. The width of the calvarial bone was measured with an optical microscope.

Example 15

Transplantation into Bone Marrow Cavity

The present inventors used 11-week-old C57BL/6 mice. The tibias were carefully perforated with a 23-gauge needle. GFP-labeled MC3T3-E1 cells were injected into the tibias with PBS (left tibia) or 300 μg/kg of slit3 (right tibia) by a 31-gauge needle. Each mouse was sacrificed after 2 or 3 days, and the tibias were fixed in 4% PFA. Each tibia was decalcified in 14% EDTA, and embedded in an OCT compound for frozen sectioning. To count GFP-positive cells, the samples were placed on a slide and observed under a fluorescence microscope (Olympus).

Example 16

Von Kossa Staining and VEGF Immunohistochemical Staining of Slit3 Knockout Mouse Embryos slit3 mutant embryos were prepared by breeding the male and female slit3+/−C57BL/6J mice purchased from Mutant Mouse Regional Resource Centers (stock number 030759-MU; Columbia, Mo., USA). The embryonic tissue was collected, and fixed in 10% formalin overnight at room temperature. For histochemical analysis, 17.5-day-old (E17.5) embryos of wild-type mice and slit3 mutant mice were fixed in 4% PFA and embedded in an OCT compound. 7 μm sections were stained with Von Kossa and nuclear fast red. For IHC staining, peroxidase chromogens (Invitrogen) were used. The sections were quenched in a solution of 3% $H_2O_2$ in methanol for 10 minutes, and then washed with PBS, and allowed to react with anti-VEGF antibody (Abcam) (diluted in PBS at 1:200 or 1:500) at room temperature for 1 hour. Signals for antibody binding were visualized with a DAB (diaminobenzidine) substrate. All the samples were observed under an optical microscope.

Example 17

Measurement of Bone Mineral Density

Systemic bone mineral density (BMD) was measured using a Lunar PIXImus densitometer (software version 1.4, GE-Lunar Co., Madison, Wis., USA) by dual-energy X-ray absorptiometry. The precision of the instrument, expressed by the coefficient of variation (CV), was 1.27%. The mice were anesthetized by intramuscular injection with a mixture of 40 mg/kg of Zoletil 50 (Virbac, France) and 5.6 mg/kg of Rompun (Bayer Korea, Seoul, Korea), and placed in a scanner in a prone position.

Example 18

Sequencing

The present inventors focused on slit2 gene (NM_004787) on chromosome 4, slit3 gene (NM_003062) on chromosome, robo1 gene (NM_001145845) on chromosome 3, robo2 gene (NM_NM_002942) on chromosome 3, and robo4 gene (NM_019055) on chromosome 11. Target regions for these genes were all coding exons, exon-intron boundaries, and regulatory regions. Bait libraries were designed and assessed for coverage across the target genomic regions using the Agilent eArray website functionality (earray.chem.agilent.com/earray/). If a bait mapped to more than one location with greater than 90% sequence identity using BLAST (~12 mismatches across the bait), this bait was removed from the design. Finally, a 6,507 bp target region was confirmed by an Agilent SureSelect Sequence Enrichment Kit. Then, sequencing using the Illumina HiSeq2000 analyzer (Illumina, San Diego, Calif.) was performed on 982 postmenopausal women (super-normal BMD group=501, and severe-low BMD group=481). The present inventors randomly sheared 3 μg of genomic DNA using the Covaris System to generate 150-bp inserts. The fragmented DNA was end-repaired using T4 DNA polymerase and Klenow polymerase, and Illumina paired-end adaptor oligonucleotides were ligated to the sticky ends. The ligation mixture was analyzed by agarose gel electrophoresis to purify 200-250 bp fragments. The purified DNA library was hybridized with SureSelect Target Enrichment probes set (Agilent, Santa Clara, Calif.) to capture the targeted region according to the manufacturer's instruction. The captured library was used to prepare the HiSeq2000 paired-end flowcell according to the manufacturer's protocol. Next, clusters of PCR colonies were then sequenced on the HiSeq2000 platform.

Experimental Result 1: Osteoclasts in the Early Differentiation Stage Secrete Potential Coupling Factors that Attract Osteoblast Precursors In order to establish an in vitro system for investigating the coupling phenomenon, variable culture conditions for osteoclastogenesis and bone resorption were prepared. The present inventors treated BMMs with 100 ng/mL RANKL for 2 days and 6 days in the presence of 30 ng/mL M-CSF to induce early- and late-osteoclast differentiation. The BMMs were cultured with 100 ng/mL RANKL and mouse femur in the presence of 30 ng/mL M-CSF for 10 days to induce the resorption stage. Osteoclast differentiation and bone resorption were assessed by measuring TRAP-5b activity and CTX concentration in each medium.

Figure 1B:
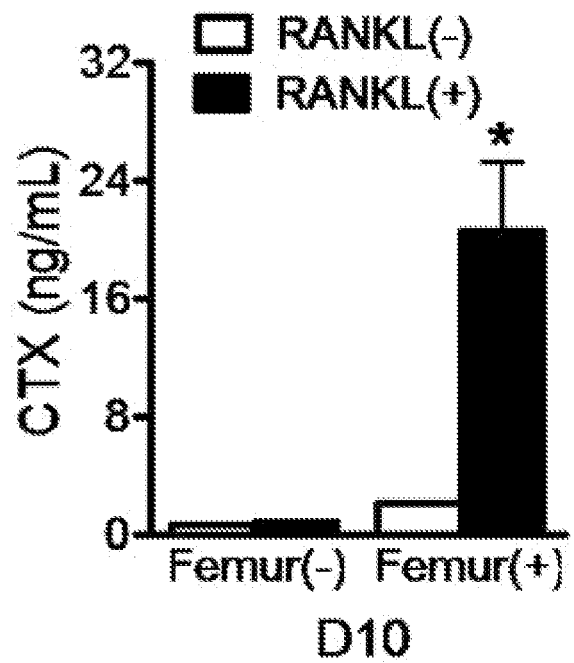

As can be seen in FIG. 1a, CM obtained from RANKL-treated cells showed a significant increase in TRAP-5b activity compared to a non-treated group in every stage. In addition, as can be seen in FIG. 1b, the CTX concentration increased only in the absence of both femur and RANKL.

Figure 2A:
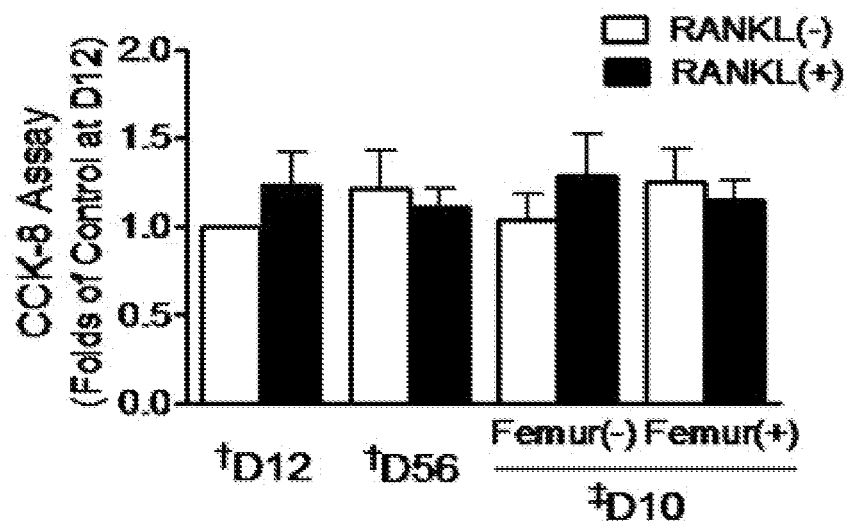
FIGS. 2a through 2i are views illustrating that the stimulation of preosteoblastic recruitment by factors derived from an early osteoclastogenesis is the key mechanism of the coupling phenomenon in a bone remodeling site.
Figure 2B:
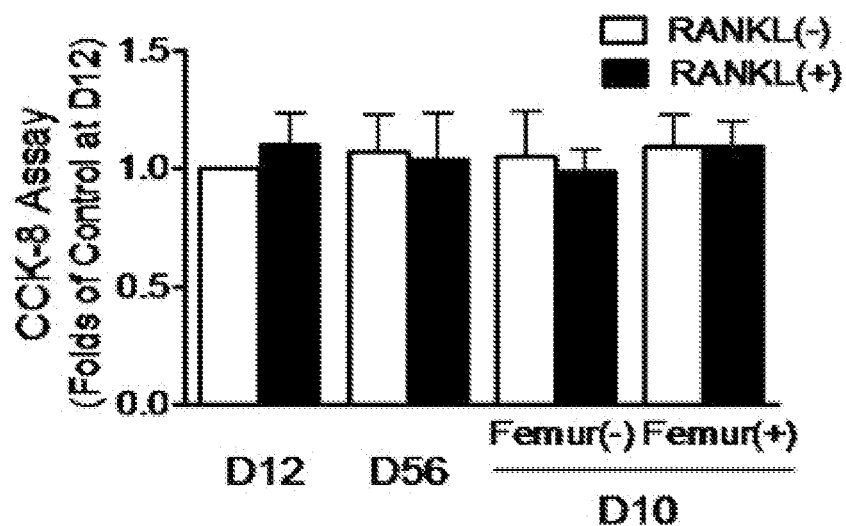
Figure 2C:
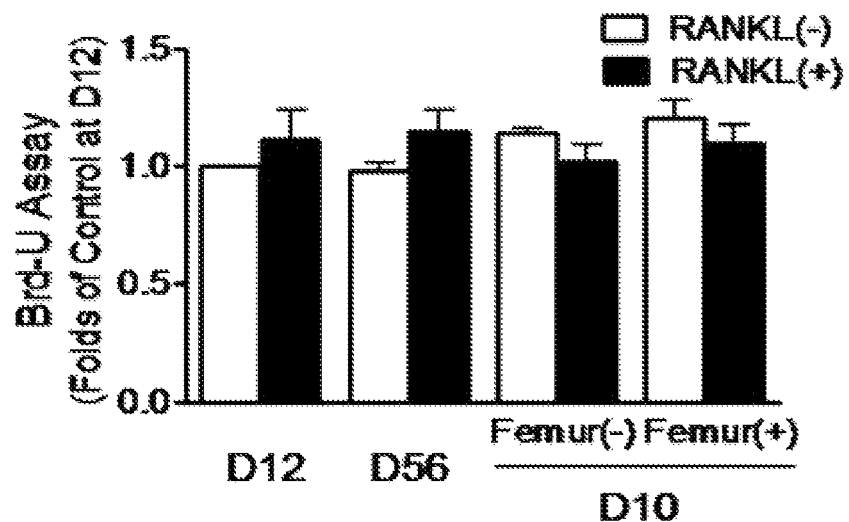
Figure 2D:
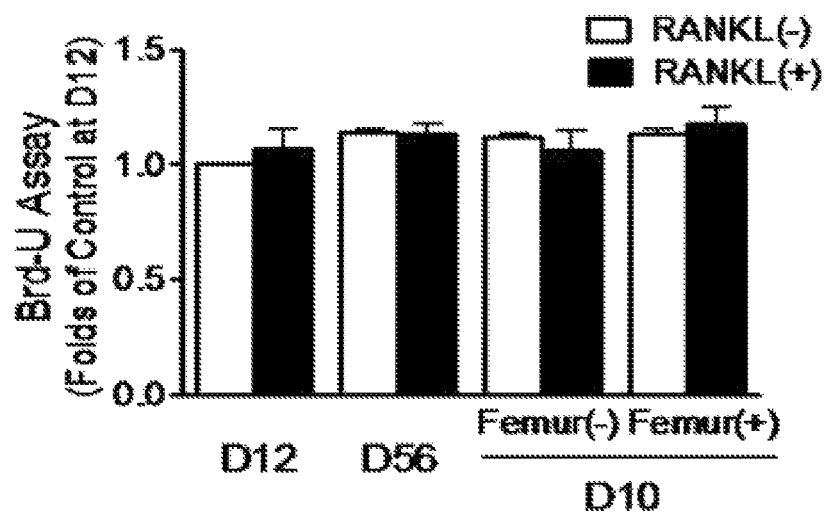
Figure 2E:
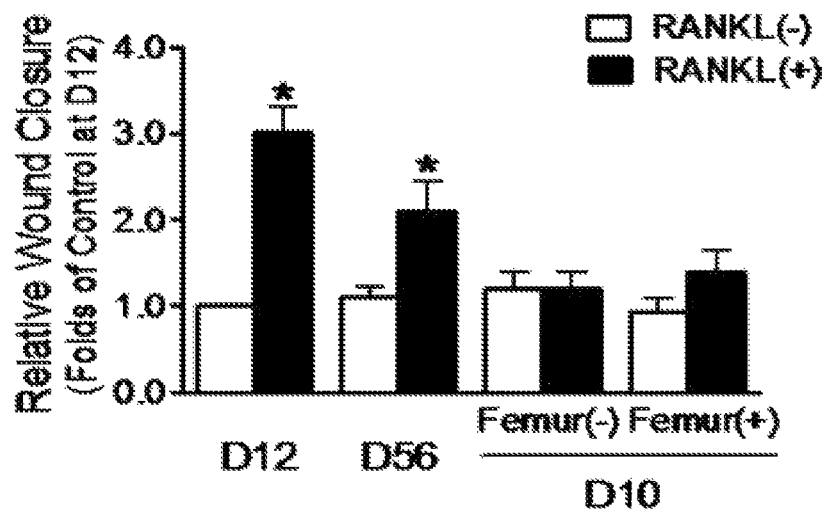
Figure 2F:
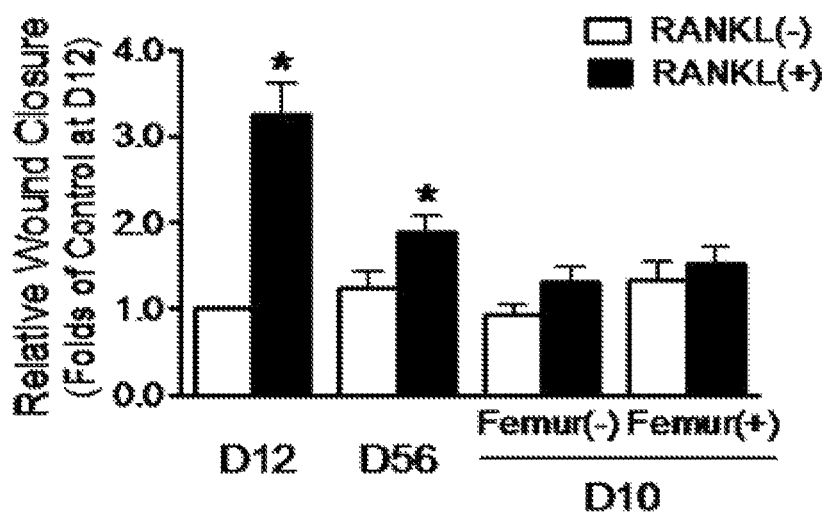
Figure 2G:
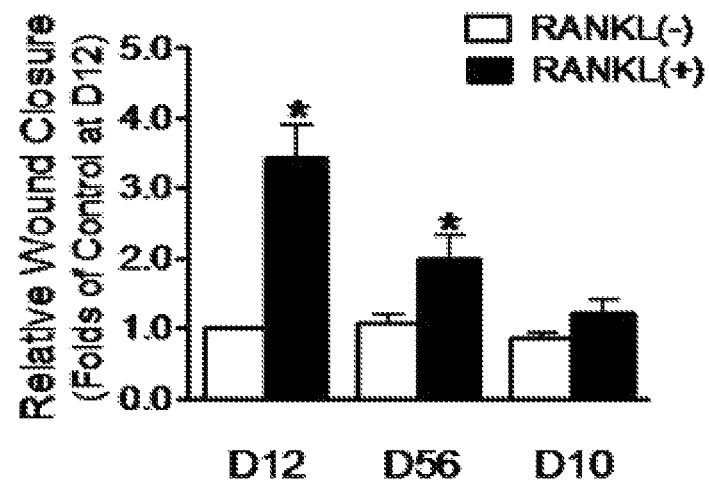

Primary mouse calvarial osteoclasts and MC3T3-E1 cells were treated with the CM collected from an osteoclast culture in each stage. Any medium of RANKL-treated BMMs had no significant effect on the viability and differentiation of primary osteoblasts (FIGS. 2a and 2c, respectively) or the viability and differentiation of MC3T3-E1 cells (FIGS. 2b and 2d, respectively) compared to the supernatant of a non-treated group. However, wound healing analysis indicated that CM obtained from RANKL-treated BMMs significantly increased the motility of both osteoblasts (FIG. 2e) and MC3T3-E1 (FIG. 2f) compared to a non-treated group. CM obtained from RANKL-treated Raw 264.7 cells also increased the mobility of MC3T3-E1 cells (FIG. 2g). Especially, the CM from RANKL-treated cells in the early differentiation stage most prominently the mobility of preosteoblasts, although those collected from RANKL-treated cells in the late differentiation stage stimulated it to a lesser degree. However, the CM from osteoclasts cultured with RANKL for 10 days did not stimulated motility regardless of the presence or absence of murine femur.

Such results suggest that possible coupling factors could be mainly secreted from early-differentiated osteoclasts, but not from resorptive processes.

Figure 2H:
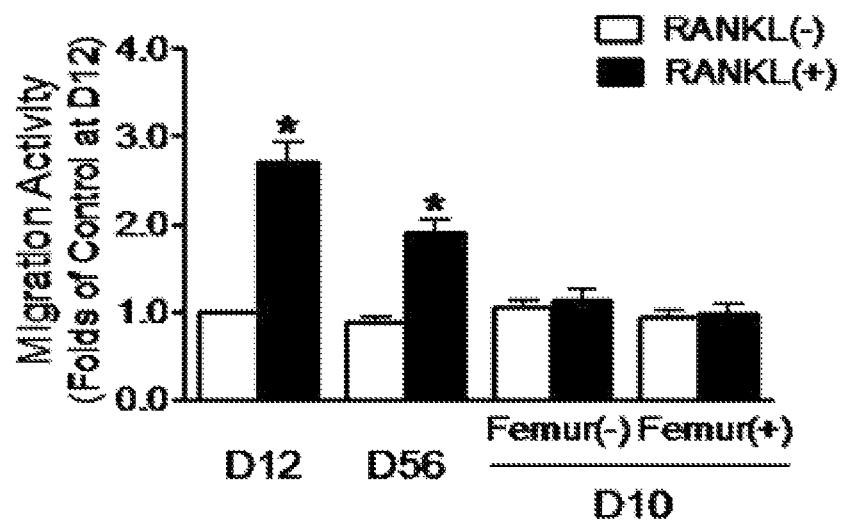
Figure 2I:
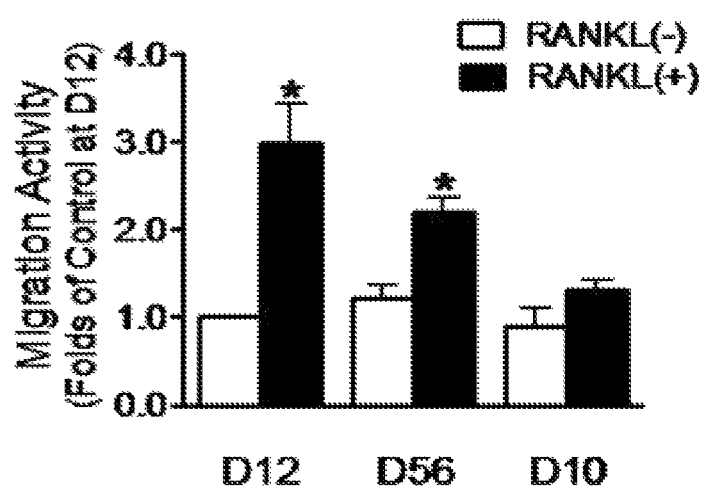

In order to assess the effect of the osteoclastic CM on the directional migration of osteoblastic lineages, the present inventors the Boyden chamber assay. The CM collected from both RANKL-treated BMM and Raw 264.7 cells also significantly stimulated the directional mobilization of MC3T3-E1 cells compared to a non-treated control (FIGS. 2h and 2i, respectively). Such results demonstrate that the stimulation of preosteoblastic recruitment by factors derived from an early osteoclastogenesis may be the key mechanism in the coupling phenomenon in a bone remodeling site.

Experimental Result 2: Identification of Putative Chemotactic Factors

To identify specific proteins that act as a chemokine for preosteoblasts, the present inventors performed fractioned LC-MS/MS. Briefly, 96 matched fractions of CM from RANKL-treated and -untreated Raw 264.7 cells were treated on MC3T3-E1 cells, and their effects on the mobilization of the cells were compared using the Boyden chamber assay. The present inventors selected the matched fractions that showed the most different effect on the migration of MC3T3-E1 cells. Proteomic analysis, as described in the Examples above, was performed on the selected fractions and contiguous RANKL-treated fractions. The present inventors identified 45 peptides that were expressed differently in the RANKL-treated fraction compared with its contiguous fractions and RANKL-untreated control. Among these, 9 peptides had secretory features (Table 1). Finally, slit3 protein was selected, and used in subsequent experiments.

TABLE 1

| Accession number | Name | MASCOTScore | Molecular weight | Matched peptides |
|---|---|---|---|---|
| O89020 | Afamin | 42 | 69.3 | 6 |
| Q80T21 | ADAMTS-like protein 4 | 33 | 113.3 | 3 |
| Q9Z319.2 | Atrial natriuretic peptide | 37 | 123.0 | 4 |
| P09470 | Angiotensin-converting enzyme | 38 | 150.8 | 3 |
| Q9WVB4 | Slit 3 | 34 | 167.7 | 3 |
| Q61292 | Laminin $\beta_2$ | 40 | 196.2 | 4 |
| NP_808531 | Fras-1 | 33 | 244.4 | 4 |
| NP031756 | Collagen α-1 chain | 39 | 333.4 | 7 |
| NP_067383 | Usherin | 40 | 569.4 | 5 |

Experimental Result 3: Slit3 is Secreted from Differentiated Osteoclasts

In order to examine whether slit3 is secreted from differentiated osteoclasts, the following experiment was performed. BMMs (bone marrow macrophages) were cultured in a medium containing ng/mL M-CSF (macrophage colony-stimulating factor) in the presence or absence of 100 ng/mL RANKL for 2 days, and Western blotting was performed on the cells. In addition, osteoclastogenesis in BMMs was suppressed using an siRNA for NFATc1 that is a master gene well known to be involved in osteoclastogenesis, and Western blotting was performed on the cells. The results are shown in FIGS. 3a and 3b.

Figure 3A:
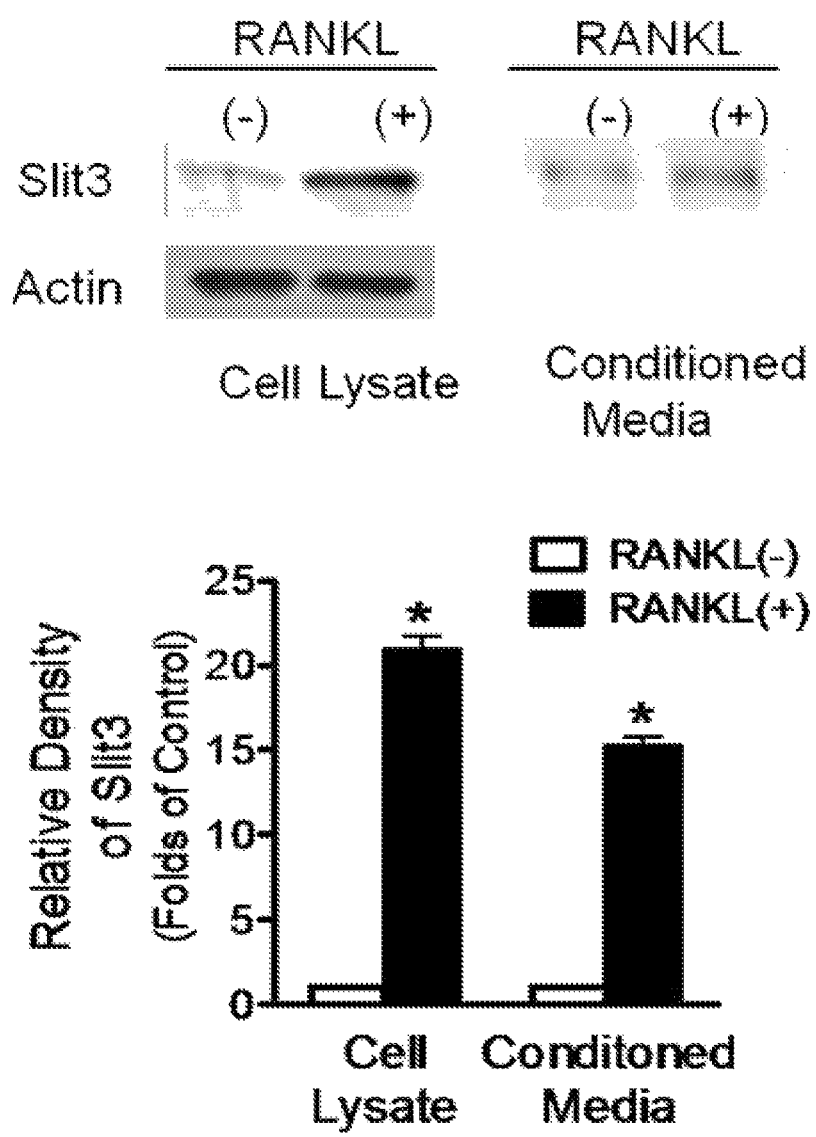
FIG. 3a is a view illustrating the secretion of slit3 from differentiated osteoclasts.

As can be seen in FIG. 3a, the expression of slit3 was increased in both the lysate and CM (conditioned media) of differentiated osteoclasts.

Figure 3B:
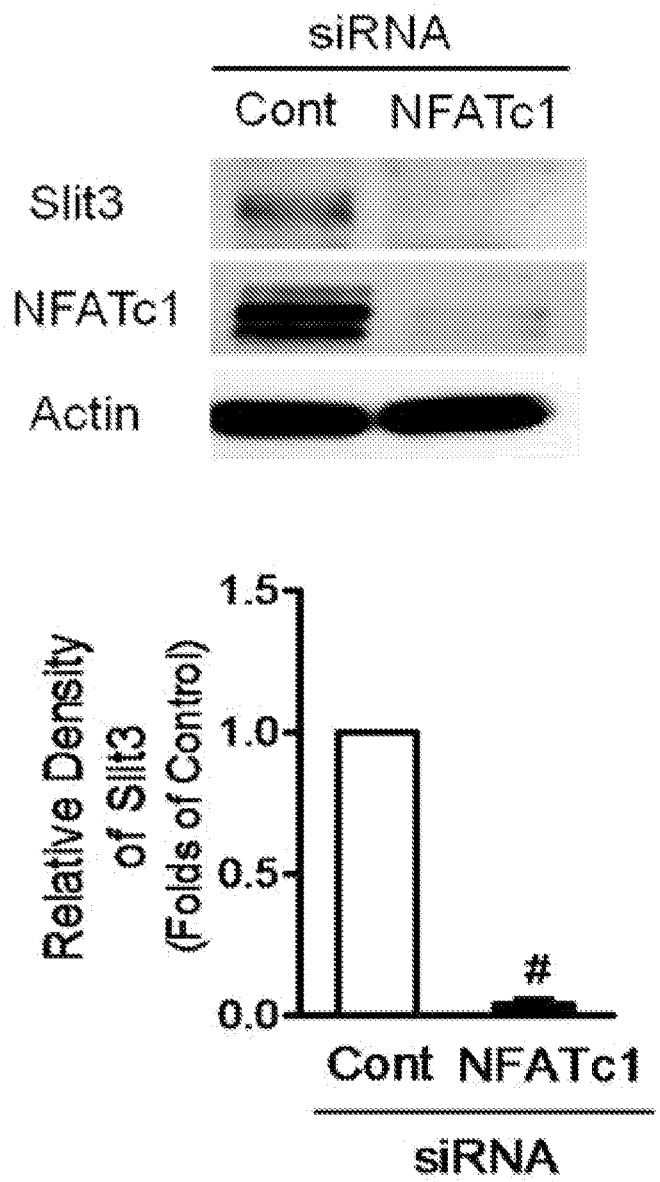
FIG. 3b is a view illustrating that the expression of slit3 in RANKL-differentiated osteoclasts is inhibited by pre-treatment with NFATc1 siRNA.

Also, as can be seen in FIG. 3b, the expression of slit3 stimulated by RANKL was completely suppressed by NFATc1-siRNA.

The above results revealed that slit3 is secreted from differentiated osteoclasts and is not secreted from osteoclast precursors.

Experimental Result 4: Slit3 Stimulates the Migration, Viability, Proliferation and Differentiation of Osteoblasts and the Production of OPG in Osteoblasts In order to examine the functions of slit3 in osteoblasts, MC3T3-E1 osteoblasts were treated with recombinant slit3, and then the effects of the recombinant slit3 on the migration, viability, proliferation and differentiation of the osteoblasts and the production of OPG (osteoprotegerin) in the osteoblasts. The results are shown in FIGS. 4a to 4g.

Figure 4A:
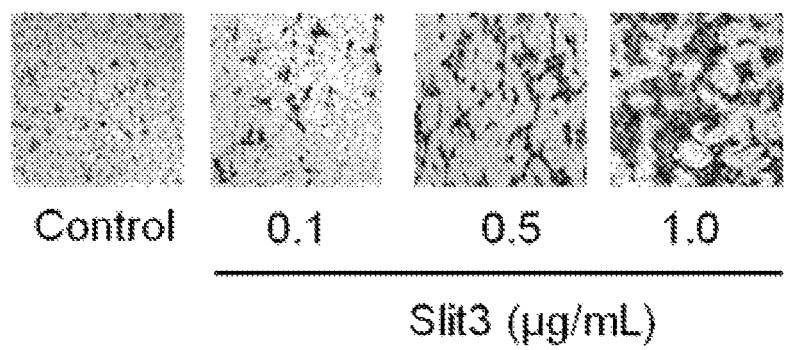
FIG. 4a is a view illustrating that the migration of osteoblasts increases depending on the concentration of slit3.
Figure 4A:
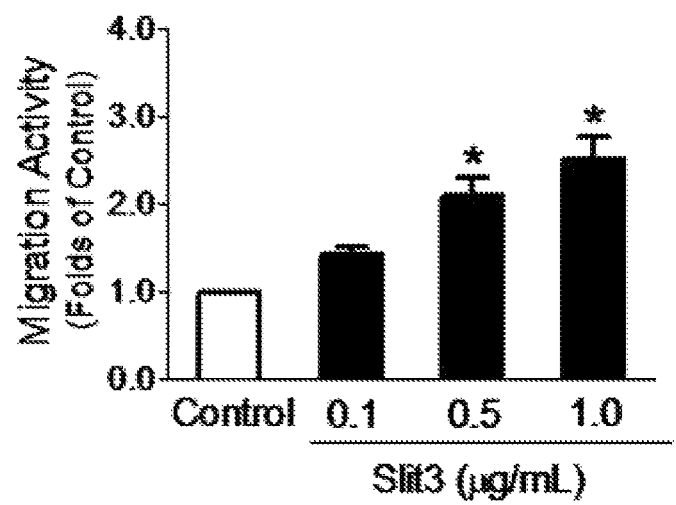

As can be seen in FIG. 4a, it was shown that, when MC3T3-E1 osteoblasts were treated with slit3 (0, 0.1, 0.5 and 1.0 μg/mL) for 24 hours, the migration of the preosteoblasts increased in a manner dependent on the concentration of slit3.

Figure 4B:
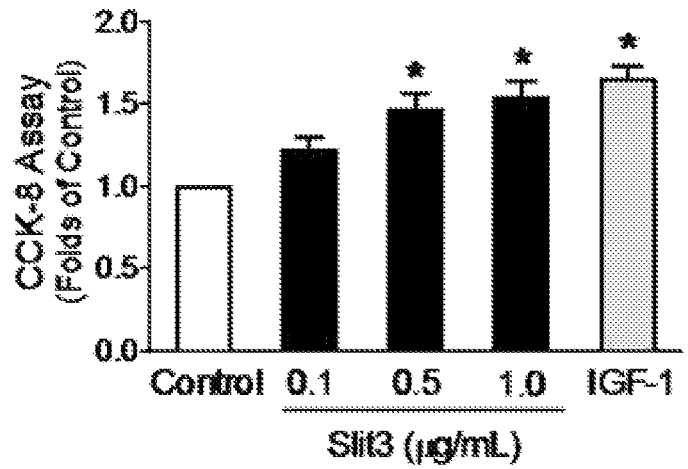
FIG. 4b is a view illustrating that the viability of osteoblasts increases depending on the concentration of slit3.
Figure 4C:
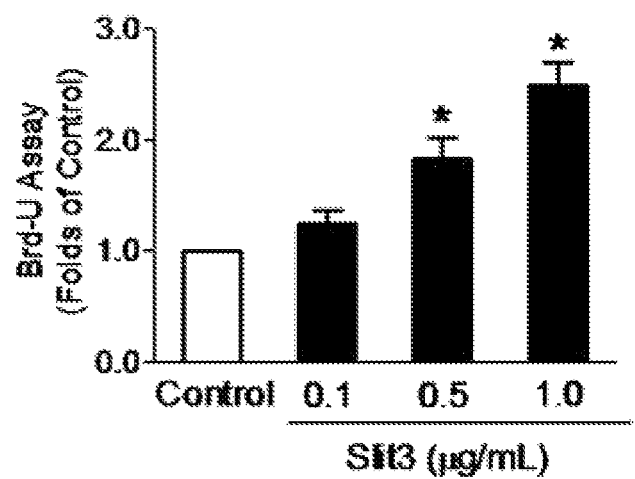
FIG. 4c is a view illustrating that the proliferation of osteoblasts increases depending on the concentration of slit3.

Also, as can be seen in FIGS. 4b and 4c, it was shown that, when MC3T3-E1 osteoblasts were treated with slit3 (0, 0.1, 0.5 and 1.0 μg/mL) for 48 hours and subjected to a CCK-8 assay and a Brd-U assay, the viability and proliferation of the osteoblasts were increased by treatment with slit3. In the CCK-8 assay, IGF-1 was used as a positive control.

Figure 4D:
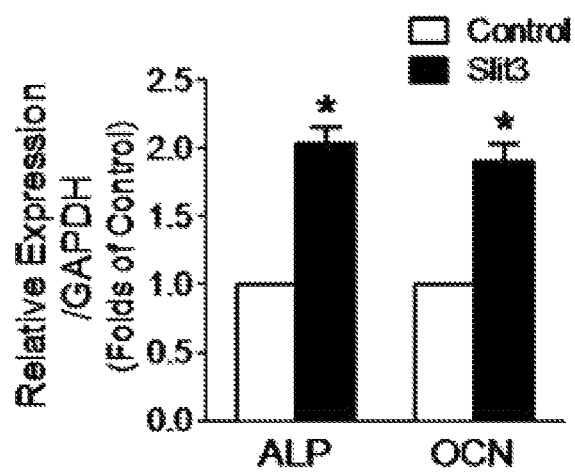
FIG. 4d is a view illustrating that the expression of osteoblast differentiation markers (ALP and OCN) is increased by slit3.

Moreover, as can be seen in FIG. 4d, it was shown that, when primary mouse BMSCs (bone marrow stromal cells) were treated with 1.0 μg/mL slit3 and the differentiation thereof was induced, the mRNA expression levels of ALP (alkaline phosphatase) and OCN (osteocalcin), which are osteoblast differentiation markers, were significantly increased by treatment with slit3.

Figure 4E:
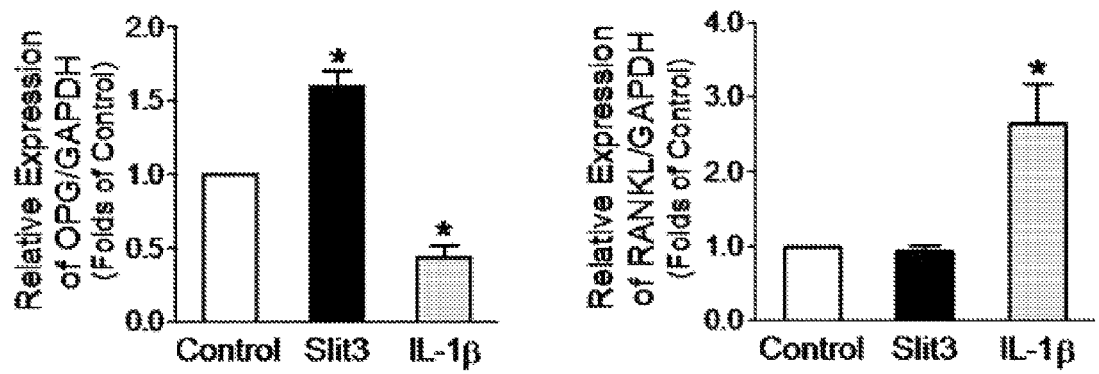
FIG. 4e is a view illustrating that the production of OPG in osteoblasts is stimulated by slit3.

Moreover, as can be seen in FIG. 4e, it was shown that, when primary mouse calvarial cells were treated with 1.0 μg/mL slit3 for 48 hours and subjected to QRT-PCR, slit3 stimulated the production of OPG and had no effect on the expression of RANKL.

Figure 4F:
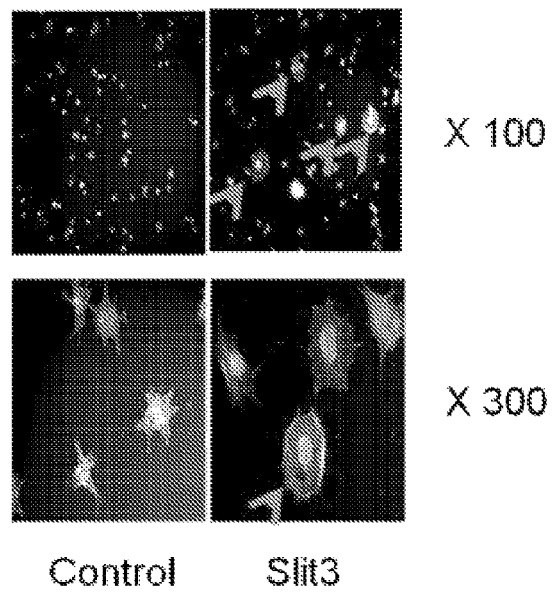
FIG. 4f is a view illustrating that lamellipodia in osteoblasts are observed by slit3.

In addition, as can be seen in FIG. 4f, slit3 stimulated the formation of lamellipodia, which move in the cell direction during cell migration and are substantially involved in mobility, suggesting that it has chemotactic action.

The above results revealed that slit3 functions to increase the migration, viability, proliferation and differentiation of osteoblasts and the production of OPG in osteoblasts, suggesting that it contributes to bone formation.

Figure 5:
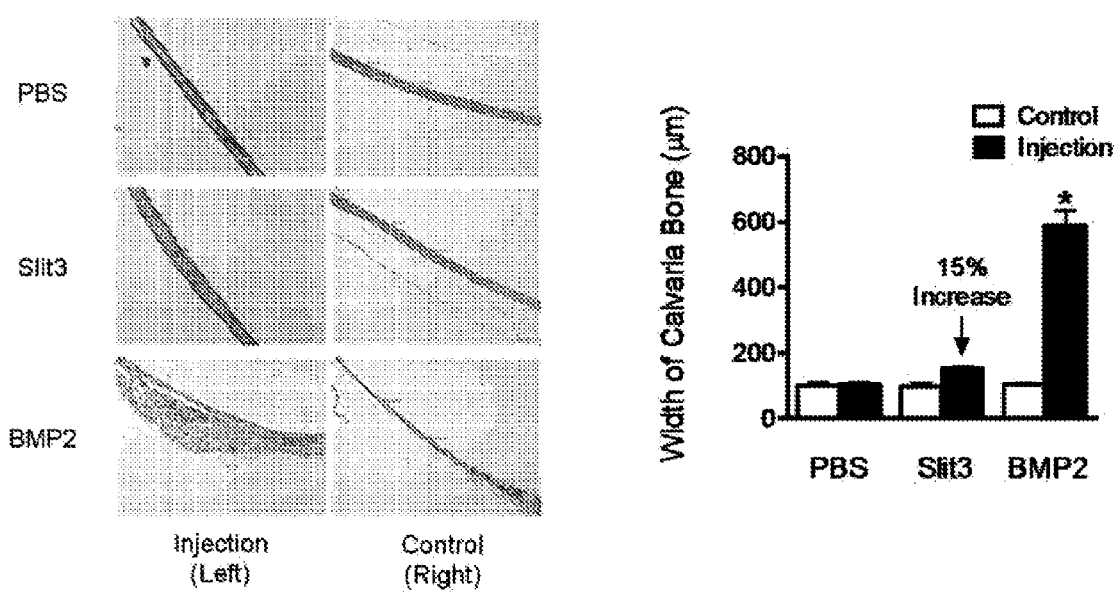
FIG. 5 is a view illustrating that bone formation in an animal model is increased by injection of slit3.
Figure 6:
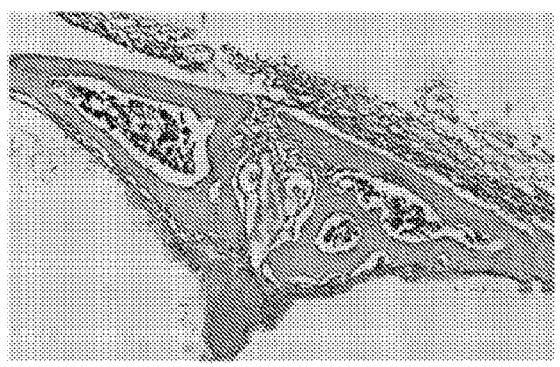
FIG. 6 is a view illustrating that bone loss in an animal model is inhibited by treatment with slit3.
Figure 6:
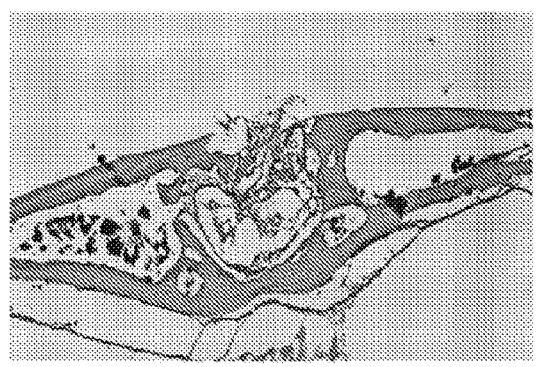
Figure 6:
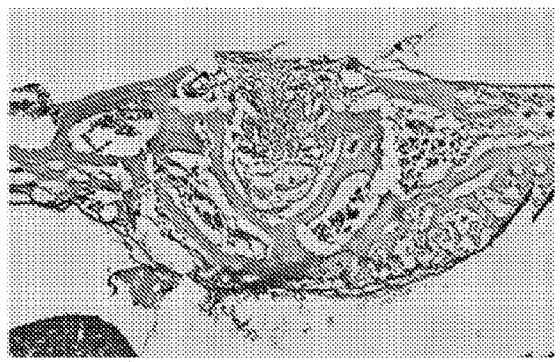
Figure 6:
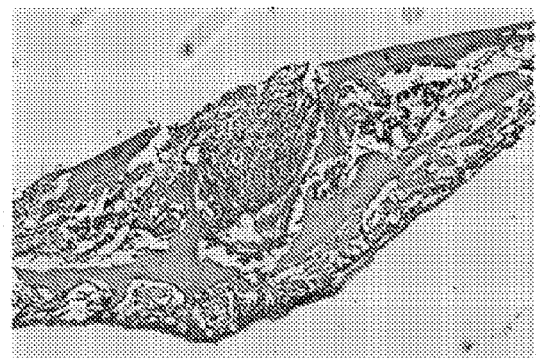

Experimental Result 5: Slit3 Increases Calvarial Bone Formation and Prevents IL-1-Induced Calvarial Bone Loss In order to verify the in vitro results for the effects of slit3 on osteocytes, an experiment was performed using an animal model. slit3 was injected directly into the calvaria, as a result, the width of the bone was increased by up to 15% compared to an untreated control (FIG. 5). In addition, it was demonstrated that, when calvarial bone loss in an animal was induced by treatment with IL-1, slit3 inhibited IL-1-induced bone loss (FIG. 6). Such results suggest that slit3 can be used as a therapeutic agent that increases bone formation while reducing bone resorption.

Figure 7:
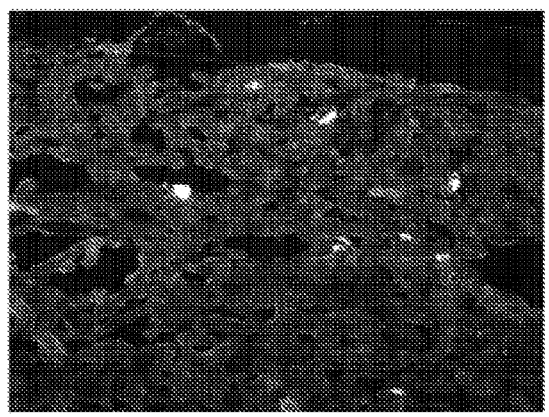
FIG. 7 is a view illustrating that the migration of osteoblasts to bone surfaces is increased by slit3.
Figure 7:
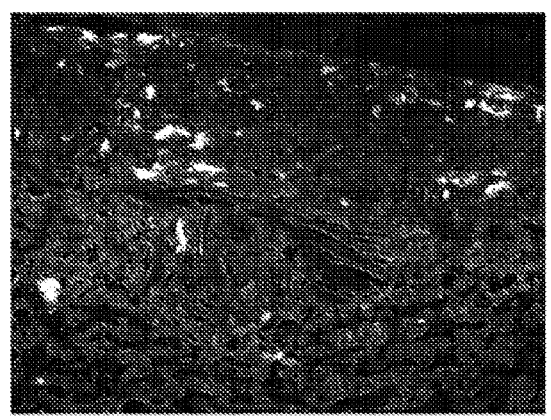

Experimental Result 6: Slit3 Stimulates the Migration of MC3T3-E1 Cells to Bone Surfaces When GFP-labeled MC3T3-E1 cells were injected into the bone marrow cavity, treatment with slit3 significantly increased the migration of the cells to the bone surfaces compared to a PBS-treated group (FIG. 7).

Figure 8A:
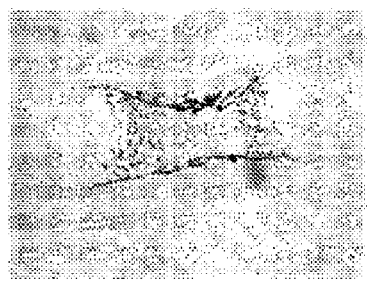
FIG. 8a is a view illustrating the results of observing the embryo of slit3 knockout mice by Von Kossa staining.
Figure 8A:
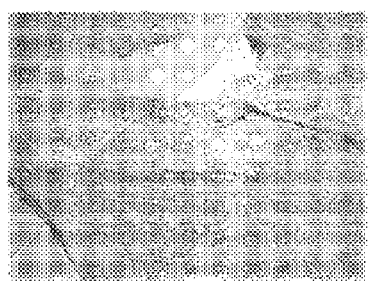
Figure 8B:
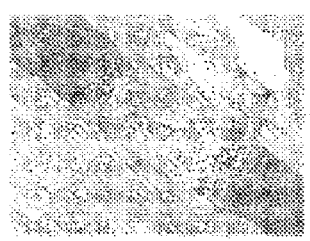
FIG. 8b is a view illustrating the results of observing the embryo of slit3 knockout mice by VEGF immunohistochemical staining.
Figure 8B:
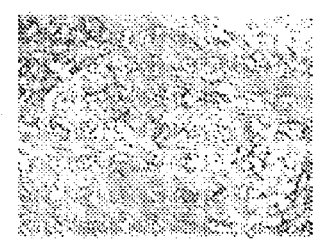
Figure 8B:
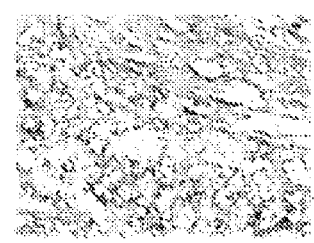
Figure 8B:
Figure 8B:
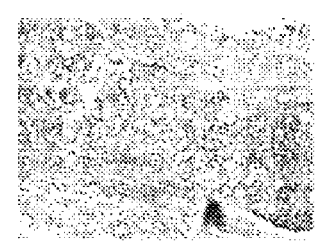
Figure 8B:

Experimental Result 7: Bone Formation and Angiogenesis in Slit3-Knockout Mouse Embryos Significantly Decrease To evaluate the accumulation of calcium in the femur of 17.5-day-old slit3-knockout mouse embryos, Von Kossa staining was performed and to evaluate the formation of blood vessels, VEGF IHC staining was performed. Slit3-knockout embryos were not substantially stained with Von Kossa (FIG. 8a) and VEGF IHC (FIG. 8b), unlike wild-type embryos. Such results suggest that slit3 continuously contributes to bone formation while playing an important role in increasing the expression of VEGF that is an essential factor for angiogenesis.

Experimental Result 8: The Action of Slit3 on Bone Cells is Mediated by Robo1 and Robo2 Receptors Because signaling pathways of slit ligand and Robo receptor in various types of cells are well known (Dickinson R E, et al., Reproduction 2010; 139: 697-704), the present inventors performed RT-PCR to investigate the expression of Robo receptor in bone cells.

Figure 9A:
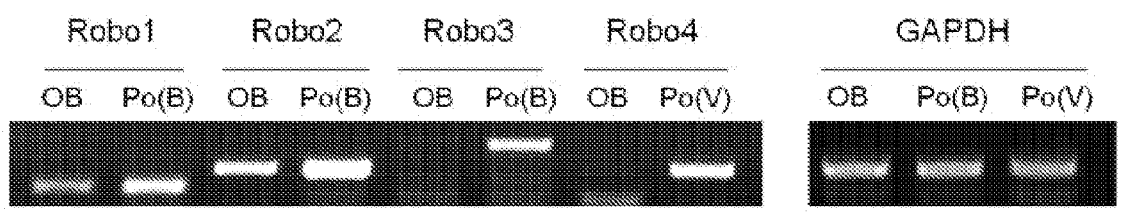
FIGS. 9a through 9e are view illustrating that the activity of slit3 in bone cells is mediated by robo1, robo2 or robo3 receptor.
Figure 9B:
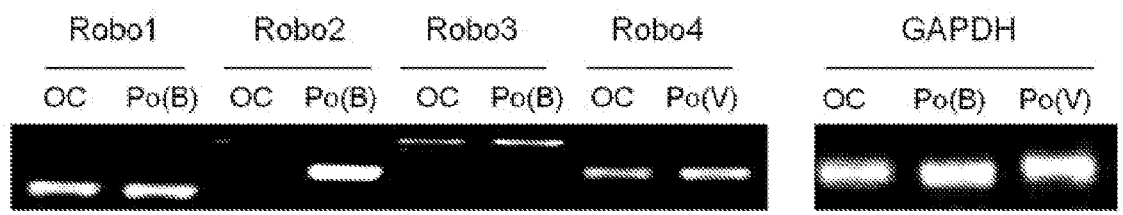
Figure 9C:
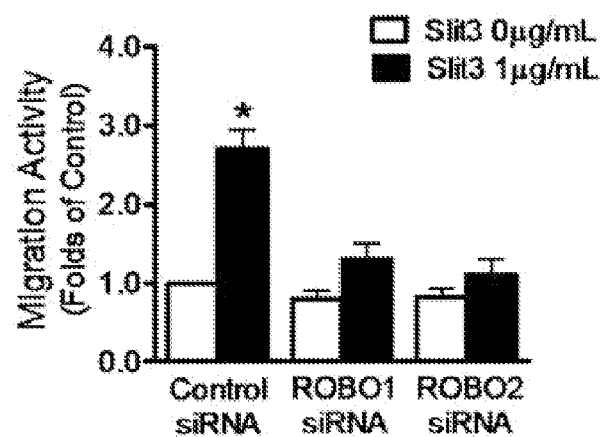
Figure 9D:
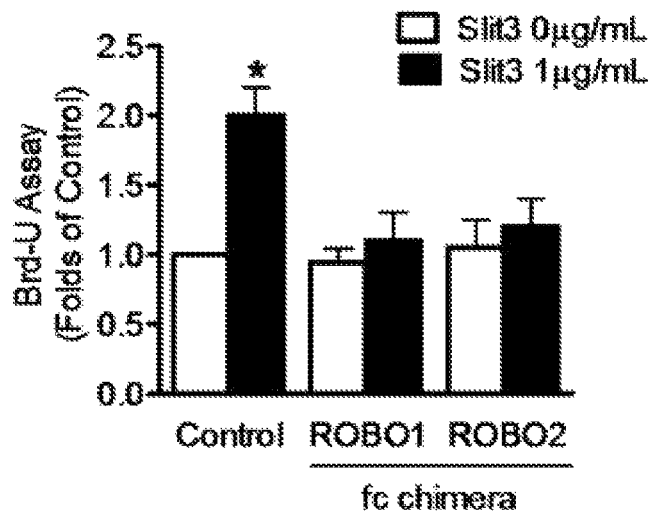
Figure 9E:
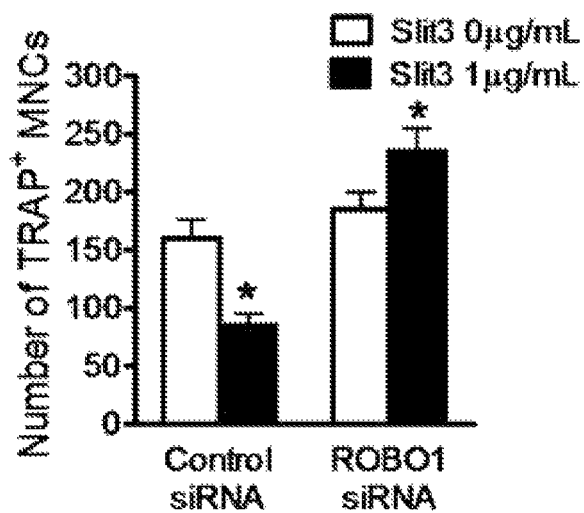

As a result, it was found that MC3T3-E1 cells expressed the Robo1 and Robo2 receptors (FIG. 9a). Primary osteoclasts mainly expressed the Robo1 receptor, whereas the expression levels of the Robo3 and Robo4 receptors therein weakly increased (FIG. 9b). When the transfection of siRNA in MC3T3-E1 cells and the fc chimera-mediated expression of Robo1 and Robo2 in the cells were suppressed, the slit3-stimulated migration and proliferation of the cells were inhibited (FIGS. 9c and 9d). In connection with primary osteoclasts, siRNA transfection for the Robo1 receptor completely restored the decrease in osteoclastogenesis by slit3 treatment (FIG. 9e).

Figure 10A:
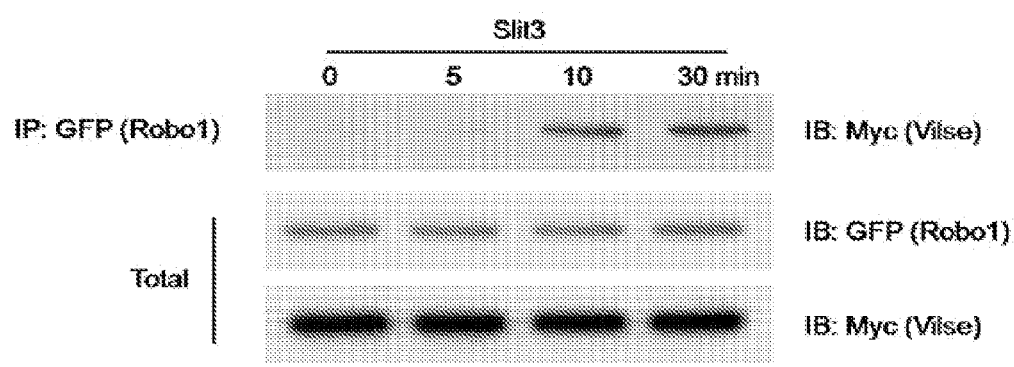
FIGS. 10a through 10c are views illustrating that the activity of slit by Robo1 receptor can be mediated by vilse in bone cells.
Figure 10B:
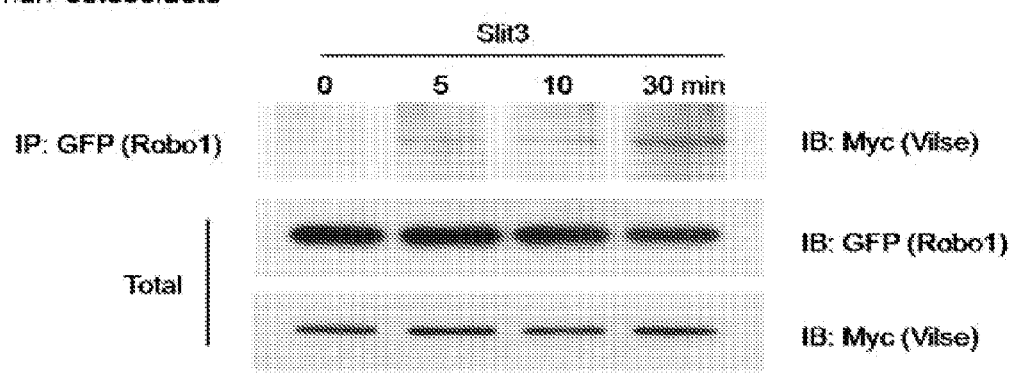
Figure 10C:
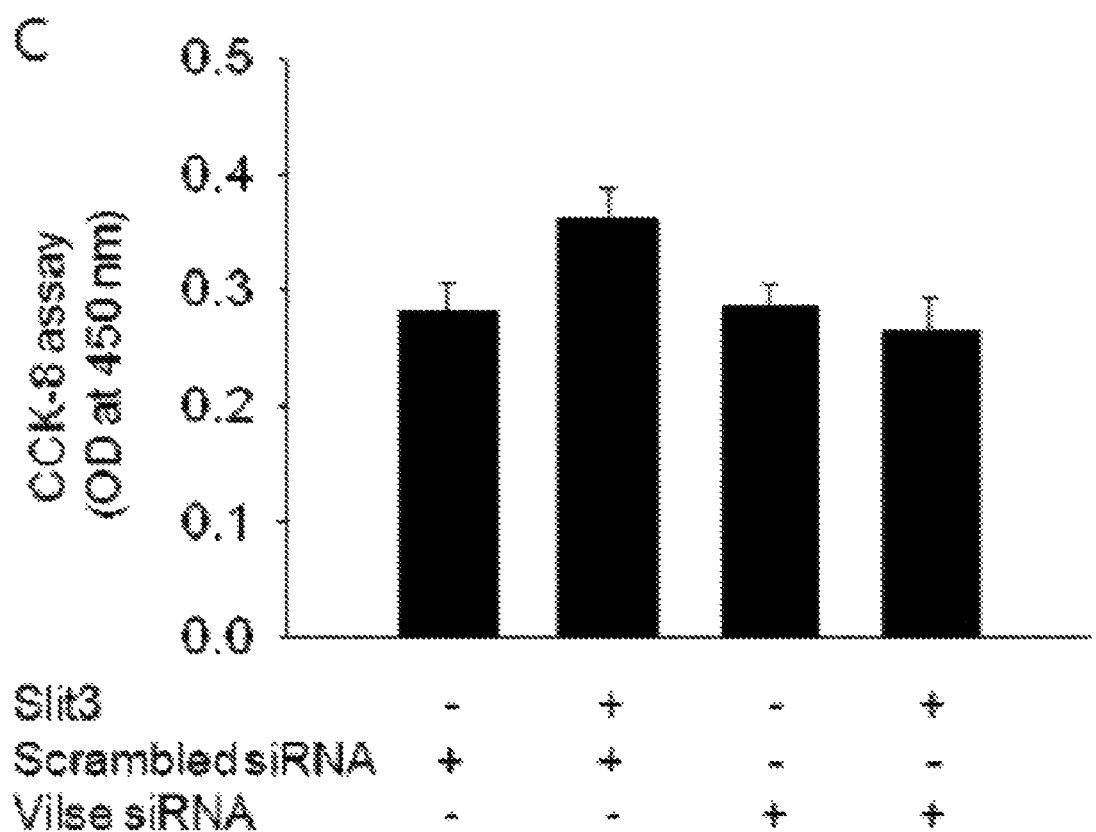

Experimental Result 9: Vilse is a Key Signaling Molecule that Mediates the Action of Slit3 by Robo1 Receptor in Osteoblasts and Osteoclasts When GFP-Robo1, produced from human BMSC and human PBMC, was transfected into osteoblasts (FIG. 10a) and osteoclasts (FIG. 10b) together with Myc-vilse, treatment with slit3 significantly increased Robo1-Vilse interactions in a co-immunoprecipitation assay. Knockdown of vilse with siRNA inhibited the slit3-stimulated viability of MC3T3-E1 cells (FIG. 10c). This result suggests that the action of slit by the Robo1 receptor can be mediated by vilse in osteocytes.

Figure 11:
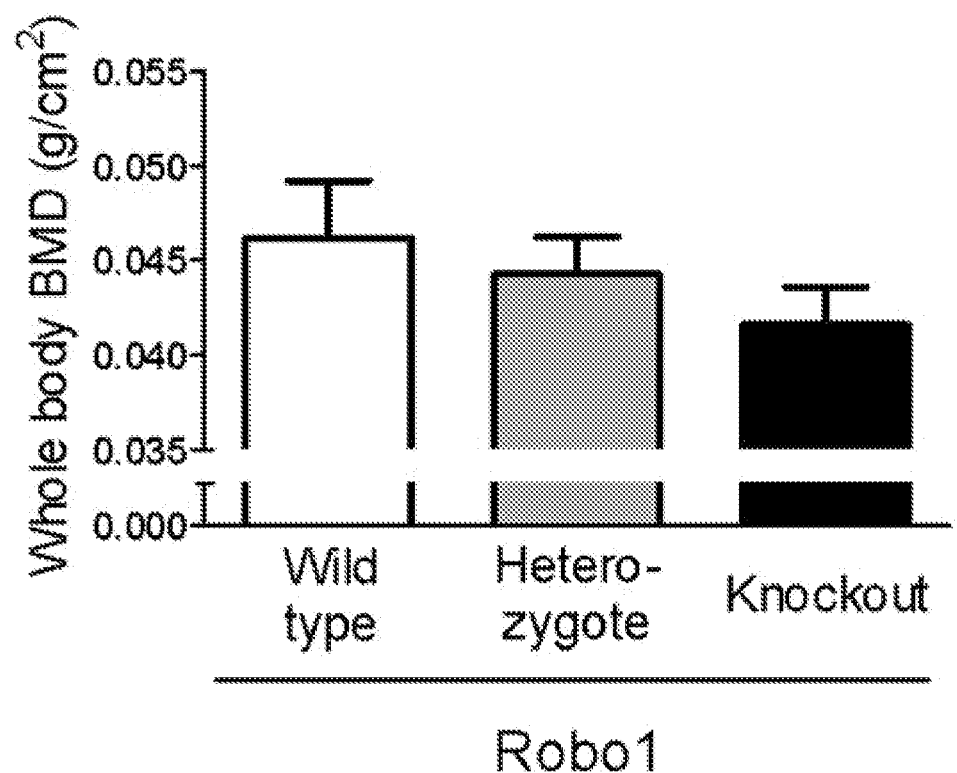
FIG. 11 is a view illustrating that bone mineral density in a Robo1-knockout animal model decreases.

Experimental Result 10: Systemic BMCs were Significantly Decreased in Robo1-Knockout Mice The systemic BMC values of 8-week-old male Robo1 wild-type, heterozygote and knockout mice were compared, and as a result, Robo1-knockout mice showed a significantly low BMD value (FIG. 11).

Figure 12:
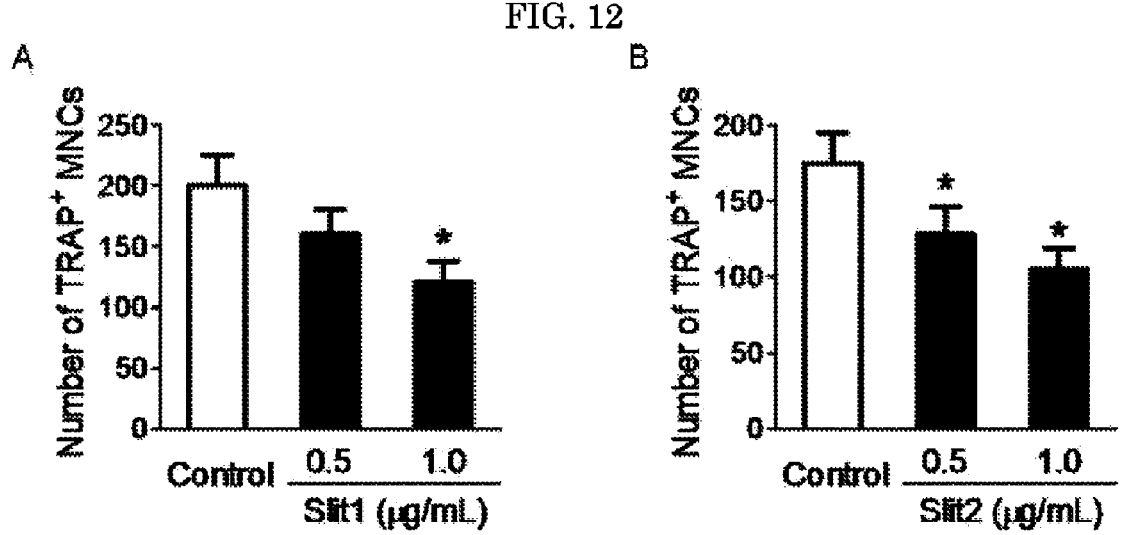
FIG. 12 is a view illustrating that the differentiation of osteoclasts is decreased by slit1 and slit2.

Experimental Result 11: Slit1 and Slit2 Reduce the Differentiation of Osteoclasts The effects of other proteins (slit1 and slit2) of the slit family on osteoclasts were tested by performing TRAP staining (FIG. 12). Slit1 and slit2 dose-dependently reduced the differentiation of osteoclasts, as observed with slit3.

Experimental Result 12: A Recombinant Slit3 LRR2 Peptide Reduces the Differentiation of Osteoclasts The LRR2 domain of slit protein was reported to bind to its receptors (Robos). Thus, the present inventors prepared a small recombinant peptide of slit3 as an LRR2 domain peptide. It was found that the recombinant peptide significantly inhibited the differentiation of osteoclasts (FIG. 13). This result suggests that the recombinant peptide can be effectively used for the treatment of osteoporosis.

Experimental Result: Clinical Test 13-1: Selection of Test Subjects

As test subjects, healthy postmenopausal women who visited the Asan Medical Center (Seoul, Korea) were selected. All the women visited because of concerns about osteoporosis or had osteoporosis detected in health examination. The postmenopausal women had sustained amenorrhea for at least 1 year, and were verified by measuring the concentration of FSH (follicle stimulating hormone) in the serum. Among the test subjects, the following subjects were excluded from the experiment: women who entered menopause before the age of 40; women who were administered with drugs, which could affect bone metabolism, before 6-12 months from the experiment; and women who suffered from diseases capable of affecting bone metabolism. 346 women were finally selected.

13-2: Measurement of Bone Mineral Density (BMD)

The age, weight, height, BMI, behavioral factors (smoking, drinking, exercise, etc.), bone mineral density and the like of the test subjects selected in the above section 13-1 were measured.

Bone mineral density (BMD, $g/cm^2$) was measured using DXA (Lunar; Prodigy, Madison, Wis., USA) for the lumbar spine (L1-L4), the femur neck of the proximal femur, the total femur, the trochanter, the shaft and the ward.

The results of the measurement are shown in Table 2 below.

TABLE 2

| Variables | Test subjects (n = 346) |
| --- | --- |
| Age (years) | 59.6 ± 7.1 |
| Weight (kg) | 55.6 ± 6.9 |
| Height (cm) | 155.2 ± 5.2 |
| Bone mass index (BMI; $kg/m^2$) | 23.1 ± 2.7 |
| Menopausal period | 9.7 ± 7.1 |
| Number of smokers (%) | 6 (1.7%) |
| Drinking ≥3 U/day, number (%) | 9 (2.6%) |
| Exercise ≥30 min/day, number (%) | 172 (49.7%) |
| Bone mineral density ($g/cm^2$) | |
| Lumbar spine | 0.882 ± 0.099 |
| Femur neck | 0.760 ± 0.085 |
| Total femur | 0.819 ± 0.091 |
| Ward | 0.556 ± 0.091 |
| Trochanter | 0.641 ± 0.084 |
| Shaft | 0.993 ± 0.119 |

13-3: Measurement of Slit3 Concentration in Blood

A fasting blood sample from each of the test subjects, selected in the above section 13-1, was centrifuged, and the supernatant was collected. The concentration of slit3 in the blood was measured using a slit3-competitive ELISA kit (Echelon Biosciences Inc, Salt Lake, Utah, USA), and the measurement was repeated twice. The data were analyzed by multiple linear regression analysis using the BMD or T-score in each bone position as a dependent variable and using the slit3 concentration as an independent variable. The results are sown in Table 3 below. Covariates included the age, weight, height, smoking, drinking and routine exercise of the test subjects.

TABLE 3

| Position | Variables | Standardized β-coefficients | P value | Position | Variables | Standardized β-coefficients | P value |
| --- | --- | --- | --- | --- | --- | --- | --- |
| Lumbar spine | BMD | 0.123 | 0.029 | ward | BMD | 0.178 | 0.001 |
| | T-score | 0.146 | 0.010 | | T-score | 0.118 | 0.026 |
| Femur neck | BMD | 0.138 | 0.012 | trochanter | BMD | 0.098 | 0.074 |
| | T-score | 0.164 | 0.003 | | T-score | 0.099 | 0.069 |
| Total femur) | BMD | 0.126 | 0.022 | shaft | BMD | 0.128 | 0.021 |
| | T-score | 0.162 | 0.003 | | | | |

As can be seen in Table 3 above, it was found that the concentration of slit3 in the blood was correlated with the BMD values and T-scores of the lumbar spine, the femur neck, the total femur, the ward, the trochanter and the shaft, after normalization with possible confounding factors.

In addition, the test subjects were grouped by quintile according to the concentration of slit3, and then the incidence of osteoporosis was observed. According to the WHO, T-score≤−2.5 SD in any one of lumbar spine, femur neck and total femur is defined as osteoporosis. The results of the observation are shown in Table 4 below.

TABLE 4

| slit3 quintile | Incidence (%) | ORs (95% CI)* |
|---|---|---|
| Q1 (1.1- 4.8 ng/mL) | 54.5 | 1 (Ref.) |
| Q2 (4.9-6.3 ng/mL) | 49.3 | 0.876 (0.420-1.830) |
| Q3 (6.4-7.5 ng/mL) | 45.6 | 0.663 (0.316-1.391) |
| Q4 (7.6-8.7 ng/mL) | 47.1 | 0.710 (0.421-1.423) |
| Q5 (8.8-14.1 ng/mL) | 38.2 | 0.421 (0.197-0.900) |

As can be seen in Table 4 above, osteoporosis odds ratio in the group (Q1) showing the lowest blood slit3 concentration was about 58% lower than that in the group (Q5) showing the highest blood slit3 concentration, after normalization with covariates.

The above results indicate that the concentration of slit3 in blood has a negative correlation with the incidence of osteoporosis, suggesting that slit3 can be used as a marker for predicting the risk of the occurrence of a fracture or osteoporosis.

Experimental Result 14: Seven SNPs in Slit2, Slit3, Robo1, Robo2 and Robo4 are Associated with the Risk of Low Bone Mineral Density The standard features of genetic research subjects according to the BMD status are shown in Table 5 below. Because the ages of the two groups were consistent, there was no significant difference in the age. As defined by the names of the groups, BMI was remarkably high in the severe-low BMD group, whereas the BMD values and T-scores in the lumbar spine and the femur neck were significantly high in the super-normal BMD group.

The genetic effects of several polymorphisms with the risk of severe-low BMD status were analyzed by targeted deep sequencing analysis and logistic regression analysis (Table 6).

One SNP (rs7655084) in slit2, two SNP (rs1549909 and rs10036727), one downstream SNP in robo1, two SNP (rs3821735 and rs78817248) in robo2, and one SNP (rs12418548) in robo4, had a significant association with the risk of severe-low BMD status.

TABLE 5

| Variables | Super-normal BMD group (n = 501) | Severe-low BMD group (n = 481) | P value |
|---|---|---|---|
| Age (years) | 58.4 ± 6.3 | 58.8 ± 7.0 | 0.343 |
| Weight (kg) | 54.5 ± 5.9 | 55.6 ± 6.7 | 0.007 |
| Height (cm) | 154.9 ± 4.8 | 154.6 ± 5.2 | 0.239 |
| Body mass index (kg/m$^2$) | 22.7 ± 2.6 | 23.3 ± 2.9 | 0.001 |
| Bone mineral density (g/cm$^2$) | | | |
| Lumbar spine | 0.983 ± 0.119 | 0.755 ± 0.095 | <0.001 |
| Femur neck | 0.778 ± 0.092 | 0.656 ± 0.094 | <0.001 |
| T-score | | | |
| Lumbar spine | −1.2 ± 0.9 | −3.2 ± 0.7 | <0.001 |
| Femur neck | −1.1 ± 0.7 | −2.3 ± 0.8 | <0.001 |
| A fracture history, no. (%) | 0 (0.0%) | 164 (34.1%) | <0.001 |

TABLE 6

| Gene | Location | Chr | Position | rs ID | Genotype | | |
|---|---|---|---|---|---|---|---|
| SLIT2 | START_GAINED | 4 | 20255306 | rs7655084 | TT (859) | GT (121) | GG (2) |
| SLIT3 | intron | 5 | 168180670 | rs1549909 | TT (359) | CT (484) | CC (138) |
| SLIT3 | exon | 5 | 168180081 | rs10036727 | TT (357) | CT (487) | CC (138) |
| ROBO1 | downstream | 3 | 78647361 | | AA (904) | AC (69) | CC (1) |
| ROBO2 | intron | 3 | 77684222 | rs3821735 | CC (606) | CT (327) | TT (49) |
| ROBO2 | intron | 3 | 77626788 | rs78817248 | CC (950) | CG (23) | GG (1) |
| ROBO4 | exon | 11 | 124757560 | rs12418548 | GG (865) | GA (112) | AA (5) |

| Gene | MAF | HWE * | Additive | | Dominant | | Recessive | |
|---|---|---|---|---|---|---|---|---|
| | | | OR (95% CI) | P | OR (95% CI) | P | OR (95% CI) | P |
| SLIT2 | 0.064 | 0.429 | 1.673 (1.145-2.445) | 0.008 | 1.655 (1.125-2.435) | 0.011 | ∞ | 0.980 |
| SLIT3 | 0.387 | 0.233 | 0.923 (0.766-1.112) | 0.399 | 1.067 (0.822-1.385) | 0.627 | 0.649 (0.449-0.938) | 0.021 |
| SLIT3 | 0.388 | 0.179 | 0.931 (0.772-1.122) | 0.450 | 1.084 (0.834-1.407) | 0.547 | 0.650 (0.450-0.940) | 0.022 |
| ROBO1 | 0.036 | 1.000 | 0.465 (0.278-0.781) | 0.004 | 0.467 (0.277-0.787) | 0.004 | 0 | 0.978 |
| ROBO2 | 0.216 | 0.579 | 0.787 (0.634-0.977) | 0.030 | 0.745 (0575-0.966) | 0.026 | 0.761 (0.425-1.364) | 0.360 |

TABLE 6-continued

|  | | | | | | | | |
|---|---|---|---|---|---|---|---|---|
| ROBO2 | 0.013 | 0.145 | 2.596 (1.097-6.142) | 0.030 | 2.593 (1.062-6.333) | 0.036 | ∞ | 0.978 |
| ROBO4 | 0.062 | 0.422 | 0.667 (0.459-0.968) | 0.033 | 0.644 (0.434-0.957) | 0.030 | 0.674 (0.112-4.077) | 0.668 |

Chr, chromosome;
MAF, minor allele frequency;
* P values for the deviation from a Hardy Weinberg Equilibrium (HWE) among all subjects.

While the present invention has been described with reference to exemplary embodiments, it will be understood by those skilled in the art to which the present invention pertains that the present invention may be embodied in other specific forms without departing from the essential characteristics of the present invention. Therefore, the embodiments disclosed above should be considered to be illustrative in all respects and not restrictive. Furthermore, the scope of the present invention should be defined by the appended claims rather than the detailed description, and all differences equivalent to the present disclosure should be interpreted to fall within the scope of the present invention.

The slit or robo protein according to the present invention increases bone formation and reduces bone resorption in cells and animal models, and has a negative correlation with the incidence of osteoporosis. Thus, it can be effectively used as a composition for preventing or treating a fracture or osteoporosis or a biomarker for predicting the risk of the occurrence of a fracture or osteoporosis.

The invention claimed is:

1. A method for treating osteoporosis, the method comprising administering a therapeutically effective amount of a peptide of a leucine-rich repeat 2 (LRR2) domain of slit3 protein to a subject requiring a treatment of said osteoporosis,
    wherein the peptide of LRR2 domain has the amino acid sequence encoded by the nucleotide sequence of SEQ ID NO: 17, and the coding region corresponds to nucleotide residues 2 to 391 of SEQ ID NO: 17.

2. A method for treating osteoporosis, the method comprising administering a therapeutically effective amount of a peptide of a leucine-rich repeat 2 (LRR2) domain of slit3 protein to a subject requiring a treatment of said osteoporosis,
    wherein the peptide of LRR2 domain has the amino acid sequence of SEQ ID NO: 46.

* * * * *

```
                          SEQUENCE LISTING

<160> NUMBER OF SEQ ID NOS: 46

<210> SEQ ID NO 1
<211> LENGTH: 1534
<212> TYPE: PRT
<213> ORGANISM: Homo sapiens

<400> SEQUENCE: 1

Met Ala Leu Thr Pro Gly Trp Gly Ser Ser Ala Gly Pro Val Arg Pro
1               5                   10                  15

Glu Leu Trp Leu Leu Trp Ala Ala Ala Trp Arg Leu Gly Ala Ser
            20                  25                  30

Ala Cys Pro Ala Leu Cys Thr Cys Thr Gly Thr Thr Val Asp Cys His
        35                  40                  45

Gly Thr Gly Leu Gln Ala Ile Pro Lys Asn Ile Pro Arg Asn Thr Glu
    50                  55                  60

Arg Leu Glu Leu Asn Gly Asn Asn Ile Thr Arg Ile His Lys Asn Asp
65                  70                  75                  80

Phe Ala Gly Leu Lys Gln Leu Arg Val Leu Gln Leu Met Glu Asn Gln
                85                  90                  95

Ile Gly Ala Val Glu Arg Gly Ala Phe Asp Asp Met Lys Glu Leu Glu
            100                 105                 110

Arg Leu Arg Leu Asn Arg Asn Gln Leu His Met Leu Pro Glu Leu Leu
        115                 120                 125

Phe Gln Asn Asn Gln Ala Leu Ser Arg Leu Asp Leu Ser Glu Asn Ala
    130                 135                 140

Ile Gln Ala Ile Pro Arg Lys Ala Phe Arg Gly Ala Thr Asp Leu Lys
145                 150                 155                 160

Asn Leu Gln Leu Asp Lys Asn Gln Ile Ser Cys Ile Glu Glu Gly Ala
                165                 170                 175

Phe Arg Ala Leu Arg Gly Leu Glu Val Leu Thr Leu Asn Asn Asn Asn
            180                 185                 190

Ile Thr Thr Ile Pro Val Ser Ser Phe Asn His Met Pro Lys Leu Arg
        195                 200                 205

Thr Phe Arg Leu His Ser Asn His Leu Phe Cys Asp Cys His Leu Ala
    210                 215                 220
```

```
Trp Leu Ser Gln Trp Leu Arg Gln Arg Pro Thr Ile Gly Leu Phe Thr
225                 230                 235                 240

Gln Cys Ser Gly Pro Ala Ser Leu Arg Gly Leu Asn Val Ala Glu Val
            245                 250                 255

Gln Lys Ser Glu Phe Ser Cys Ser Gly Gln Gly Glu Ala Gly Arg Val
        260                 265                 270

Pro Thr Cys Thr Leu Ser Ser Gly Ser Cys Pro Ala Met Cys Thr Cys
    275                 280                 285

Ser Asn Gly Ile Val Asp Cys Arg Gly Lys Gly Leu Thr Ala Ile Pro
290                 295                 300

Ala Asn Leu Pro Glu Thr Met Thr Glu Ile Arg Leu Glu Leu Asn Gly
305                 310                 315                 320

Ile Lys Ser Ile Pro Pro Gly Ala Phe Ser Pro Tyr Arg Lys Leu Arg
                325                 330                 335

Arg Ile Asp Leu Ser Asn Asn Gln Ile Ala Glu Ile Ala Pro Asp Ala
            340                 345                 350

Phe Gln Gly Leu Arg Ser Leu Asn Ser Leu Val Leu Tyr Gly Asn Lys
        355                 360                 365

Ile Thr Asp Leu Pro Arg Gly Val Phe Gly Gly Leu Tyr Thr Leu Gln
    370                 375                 380

Leu Leu Leu Leu Asn Ala Asn Lys Ile Asn Cys Ile Arg Pro Asp Ala
385                 390                 395                 400

Phe Gln Asp Leu Gln Asn Leu Ser Leu Leu Ser Leu Tyr Asp Asn Lys
                405                 410                 415

Ile Gln Ser Leu Ala Lys Gly Thr Phe Thr Ser Leu Arg Ala Ile Gln
            420                 425                 430

Thr Leu His Leu Ala Gln Asn Pro Phe Ile Cys Asp Cys Asn Leu Lys
        435                 440                 445

Trp Leu Ala Asp Phe Leu Arg Thr Asn Pro Ile Glu Thr Ser Gly Ala
    450                 455                 460

Arg Cys Ala Ser Pro Arg Arg Leu Ala Asn Lys Arg Ile Gly Gln Ile
465                 470                 475                 480

Lys Ser Lys Lys Phe Arg Cys Ser Ala Lys Glu Gln Tyr Phe Ile Pro
                485                 490                 495

Gly Thr Glu Asp Tyr Gln Leu Asn Ser Glu Cys Asn Ser Asp Val Val
            500                 505                 510

Cys Pro His Lys Cys Arg Cys Glu Ala Asn Val Val Glu Cys Ser Ser
        515                 520                 525

Leu Lys Leu Thr Lys Ile Pro Glu Arg Ile Pro Gln Ser Thr Ala Glu
    530                 535                 540

Leu Arg Leu Asn Asn Asn Glu Ile Ser Ile Leu Glu Ala Thr Gly Met
545                 550                 555                 560

Phe Lys Lys Leu Thr His Leu Lys Lys Ile Asn Leu Ser Asn Asn Lys
                565                 570                 575

Val Ser Glu Ile Glu Asp Gly Ala Phe Glu Gly Ala Ala Ser Val Ser
            580                 585                 590

Glu Leu His Leu Thr Ala Asn Gln Leu Glu Ser Ile Arg Ser Gly Met
        595                 600                 605

Phe Arg Gly Leu Asp Gly Leu Arg Thr Leu Met Leu Arg Asn Asn Arg
    610                 615                 620

Ile Ser Cys Ile His Asn Asp Ser Phe Thr Gly Leu Arg Asn Val Arg
625                 630                 635                 640

Leu Leu Ser Leu Tyr Asp Asn Gln Ile Thr Thr Val Ser Pro Gly Ala
```

645                 650                 655
Phe Asp Thr Leu Gln Ser Leu Ser Thr Leu Asn Leu Leu Ala Asn Pro
                660                 665                 670

Phe Asn Cys Asn Cys Gln Leu Ala Trp Leu Gly Gly Trp Leu Arg Lys
                675                 680                 685

Arg Lys Ile Val Thr Gly Asn Pro Arg Cys Gln Asn Pro Asp Phe Leu
            690                 695                 700

Arg Gln Ile Pro Leu Gln Asp Val Ala Phe Pro Asp Phe Arg Cys Glu
705                 710                 715                 720

Glu Gly Gln Glu Glu Gly Gly Cys Leu Pro Arg Pro Gln Cys Pro Gln
                725                 730                 735

Glu Cys Ala Cys Leu Asp Thr Val Val Arg Cys Ser Asn Lys His Leu
                740                 745                 750

Arg Ala Leu Pro Lys Gly Ile Pro Lys Asn Val Thr Glu Leu Tyr Leu
                755                 760                 765

Asp Gly Asn Gln Phe Thr Leu Val Pro Gly Gln Leu Ser Thr Phe Lys
            770                 775                 780

Tyr Leu Gln Leu Val Asp Leu Ser Asn Asn Lys Ile Ser Ser Leu Ser
785                 790                 795                 800

Asn Ser Ser Phe Thr Asn Met Ser Gln Leu Thr Thr Leu Ile Leu Ser
                805                 810                 815

Tyr Asn Ala Leu Gln Cys Ile Pro Pro Leu Ala Phe Gln Gly Leu Arg
                820                 825                 830

Ser Leu Arg Leu Leu Ser Leu His Gly Asn Asp Ile Ser Thr Leu Gln
                835                 840                 845

Glu Gly Ile Phe Ala Asp Val Thr Ser Leu Ser His Leu Ala Ile Gly
            850                 855                 860

Ala Asn Pro Leu Tyr Cys Asp Cys His Leu Arg Trp Leu Ser Ser Trp
865                 870                 875                 880

Val Lys Thr Gly Tyr Lys Glu Pro Gly Ile Ala Arg Cys Ala Gly Pro
                885                 890                 895

Gln Asp Met Glu Gly Lys Leu Leu Leu Thr Thr Pro Ala Lys Lys Phe
                900                 905                 910

Glu Cys Gln Gly Pro Pro Thr Leu Ala Val Gln Ala Lys Cys Asp Leu
                915                 920                 925

Cys Leu Ser Ser Pro Cys Gln Asn Gln Gly Thr Cys His Asn Asp Pro
            930                 935                 940

Leu Glu Val Tyr Arg Cys Ala Cys Pro Ser Gly Tyr Lys Gly Arg Asp
945                 950                 955                 960

Cys Glu Val Ser Leu Asp Ser Cys Ser Ser Gly Pro Cys Glu Asn Gly
                965                 970                 975

Gly Thr Cys His Ala Gln Glu Gly Glu Asp Ala Pro Phe Thr Cys Ser
                980                 985                 990

Cys Pro Thr Gly Phe Glu Gly Pro Thr Cys Gly Val Asn Thr Asp Asp
            995                 1000                1005

Cys Val Asp His Ala Cys Ala Asn Gly Gly Val Cys Val Asp Gly
            1010                1015                1020

Val Gly Asn Tyr Thr Cys Gln Cys Pro Leu Gln Tyr Glu Gly Lys
            1025                1030                1035

Ala Cys Glu Gln Leu Val Asp Leu Cys Ser Pro Asp Leu Asn Pro
            1040                1045                1050

Cys Gln His Glu Ala Gln Cys Val Gly Thr Pro Asp Gly Pro Arg
            1055                1060                1065

-continued

```
Cys Glu Cys Met Pro Gly Tyr Ala Gly Asp Asn Cys Ser Glu Asn
    1070            1075            1080

Gln Asp Asp Cys Arg Asp His Arg Cys Gln Asn Gly Ala Gln Cys
    1085            1090            1095

Met Asp Glu Val Asn Ser Tyr Ser Cys Leu Cys Ala Glu Gly Tyr
    1100            1105            1110

Ser Gly Gln Leu Cys Glu Ile Pro Pro His Leu Pro Ala Pro Lys
    1115            1120            1125

Ser Pro Cys Glu Gly Thr Glu Cys Gln Asn Gly Ala Asn Cys Val
    1130            1135            1140

Asp Gln Gly Asn Arg Pro Val Cys Gln Cys Leu Pro Gly Phe Gly
    1145            1150            1155

Gly Pro Glu Cys Glu Lys Leu Leu Ser Val Asn Phe Val Asp Arg
    1160            1165            1170

Asp Thr Tyr Leu Gln Phe Thr Asp Leu Gln Asn Trp Pro Arg Ala
    1175            1180            1185

Asn Ile Thr Leu Gln Val Ser Thr Ala Glu Asp Asn Gly Ile Leu
    1190            1195            1200

Leu Tyr Asn Gly Asp Asn Asp His Ile Ala Val Glu Leu Tyr Gln
    1205            1210            1215

Gly His Val Arg Val Ser Tyr Asp Pro Gly Ser Tyr Pro Ser Ser
    1220            1225            1230

Ala Ile Tyr Ser Ala Glu Thr Ile Asn Asp Gly Gln Phe His Thr
    1235            1240            1245

Val Glu Leu Val Ala Phe Asp Gln Met Val Asn Leu Ser Ile Asp
    1250            1255            1260

Gly Gly Ser Pro Met Thr Met Asp Asn Phe Gly Lys His Tyr Thr
    1265            1270            1275

Leu Asn Ser Glu Ala Pro Leu Tyr Val Gly Gly Met Pro Val Asp
    1280            1285            1290

Val Asn Ser Ala Ala Phe Arg Leu Trp Gln Ile Leu Asn Gly Thr
    1295            1300            1305

Gly Phe His Gly Cys Ile Arg Asn Leu Tyr Ile Asn Asn Glu Leu
    1310            1315            1320

Gln Asp Phe Thr Lys Thr Gln Met Lys Pro Gly Val Val Pro Gly
    1325            1330            1335

Cys Glu Pro Cys Arg Lys Leu Tyr Cys Leu His Gly Ile Cys Gln
    1340            1345            1350

Pro Asn Ala Thr Pro Gly Pro Met Cys His Cys Glu Ala Gly Trp
    1355            1360            1365

Val Gly Leu His Cys Asp Gln Pro Ala Asp Gly Pro Cys His Gly
    1370            1375            1380

His Lys Cys Val His Gly Gln Cys Val Pro Leu Asp Ala Leu Ser
    1385            1390            1395

Tyr Ser Cys Gln Cys Gln Asp Gly Tyr Ser Gly Ala Leu Cys Asn
    1400            1405            1410

Gln Ala Gly Ala Leu Ala Glu Pro Cys Arg Gly Leu Gln Cys Leu
    1415            1420            1425

His Gly His Cys Gln Ala Ser Gly Thr Lys Gly Ala His Cys Val
    1430            1435            1440

Cys Asp Pro Gly Phe Ser Gly Glu Leu Cys Glu Gln Glu Ser Glu
    1445            1450            1455
```

```
Cys Arg Gly Asp Pro Val Arg Asp Phe His Gln Val Gln Arg Gly
    1460                1465                1470

Tyr Ala Ile Cys Gln Thr Thr Arg Pro Leu Ser Trp Val Glu Cys
    1475                1480                1485

Arg Gly Ser Cys Pro Gly Gln Gly Cys Cys Gln Gly Leu Arg Leu
    1490                1495                1500

Lys Arg Arg Lys Phe Thr Phe Glu Cys Ser Asp Gly Thr Ser Phe
    1505                1510                1515

Ala Glu Glu Val Glu Lys Pro Thr Lys Cys Gly Cys Ala Leu Cys
    1520                1525                1530

Ala

<210> SEQ ID NO 2
<211> LENGTH: 1525
<212> TYPE: PRT
<213> ORGANISM: Homo sapiens

<400> SEQUENCE: 2

Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Lys Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Glu Gly His Gln Ser Phe Met Ala Pro Ser Cys
            260                 265                 270

Ser Val Leu His Cys Pro Ala Ala Cys Thr Cys Ser Asn Asn Ile Val
        275                 280                 285
```

```
Asp Cys Arg Gly Lys Gly Leu Thr Glu Ile Pro Thr Asn Leu Pro Glu
290                 295                 300
Thr Ile Thr Glu Ile Arg Leu Glu Gln Asn Thr Ile Lys Val Ile Pro
305                 310                 315                 320
Pro Gly Ala Phe Ser Pro Tyr Lys Lys Leu Arg Arg Ile Asp Leu Ser
                325                 330                 335
Asn Asn Gln Ile Ser Glu Leu Ala Pro Asp Ala Phe Gln Gly Leu Arg
                340                 345                 350
Ser Leu Asn Ser Leu Val Leu Tyr Gly Asn Lys Ile Thr Glu Leu Pro
            355                 360                 365
Lys Ser Leu Phe Glu Gly Leu Phe Ser Leu Gln Leu Leu Leu Leu Asn
370                 375                 380
Ala Asn Lys Ile Asn Cys Leu Arg Val Asp Ala Phe Gln Asp Leu His
385                 390                 395                 400
Asn Leu Asn Leu Leu Ser Leu Tyr Asp Asn Lys Leu Gln Thr Ile Ala
                405                 410                 415
Lys Gly Thr Phe Ser Pro Leu Arg Ala Ile Gln Thr Met His Leu Ala
                420                 425                 430
Gln Asn Pro Phe Ile Cys Asp Cys His Leu Lys Trp Leu Ala Asp Tyr
            435                 440                 445
Leu His Thr Asn Pro Ile Glu Thr Ser Gly Ala Arg Cys Thr Ser Pro
450                 455                 460
Arg Arg Leu Ala Asn Lys Arg Ile Gly Gln Ile Lys Ser Lys Lys Phe
465                 470                 475                 480
Arg Cys Ser Gly Thr Glu Asp Tyr Arg Ser Lys Leu Ser Gly Asp Cys
                485                 490                 495
Phe Ala Asp Leu Ala Cys Pro Glu Lys Cys Arg Cys Glu Gly Thr Thr
                500                 505                 510
Val Asp Cys Ser Asn Gln Lys Leu Asn Lys Ile Pro Glu His Ile Pro
            515                 520                 525
Gln Tyr Thr Ala Glu Leu Arg Leu Asn Asn Asn Glu Phe Thr Val Leu
            530                 535                 540
Glu Ala Thr Gly Ile Phe Lys Lys Leu Pro Gln Leu Arg Lys Ile Asn
545                 550                 555                 560
Phe Ser Asn Asn Lys Ile Thr Asp Ile Glu Glu Gly Ala Phe Glu Gly
                565                 570                 575
Ala Ser Gly Val Asn Glu Ile Leu Leu Thr Ser Asn Arg Leu Glu Asn
                580                 585                 590
Val Gln His Lys Met Phe Lys Gly Leu Glu Ser Leu Lys Thr Leu Met
            595                 600                 605
Leu Arg Ser Asn Arg Ile Thr Cys Val Gly Asn Asp Ser Phe Ile Gly
610                 615                 620
Leu Ser Ser Val Arg Leu Leu Ser Leu Tyr Asp Asn Gln Ile Thr Thr
625                 630                 635                 640
Val Ala Pro Gly Ala Phe Asp Thr Leu His Ser Leu Ser Thr Leu Asn
                645                 650                 655
Leu Leu Ala Asn Pro Phe Asn Cys Asn Cys Tyr Leu Ala Trp Leu Gly
                660                 665                 670
Glu Trp Leu Arg Lys Lys Arg Ile Val Thr Gly Asn Pro Arg Cys Gln
            675                 680                 685
Lys Pro Tyr Phe Leu Lys Glu Ile Pro Ile Gln Asp Val Ala Ile Gln
690                 695                 700
Asp Phe Thr Cys Asp Asp Gly Asn Asp Asp Asn Ser Cys Ser Pro Leu
```

```
                705                 710                 715                 720
Ser Arg Cys Pro Thr Glu Cys Thr Cys Leu Asp Thr Val Val Arg Cys
                    725                 730                 735

Ser Asn Lys Gly Leu Lys Val Leu Pro Lys Gly Ile Pro Arg Asp Val
                    740                 745                 750

Thr Glu Leu Tyr Leu Asp Gly Asn Gln Phe Thr Leu Val Pro Lys Glu
                    755                 760                 765

Leu Ser Asn Tyr Lys His Leu Thr Leu Ile Asp Leu Ser Asn Asn Arg
770                 775                 780

Ile Ser Thr Leu Ser Asn Gln Ser Phe Ser Asn Met Thr Gln Leu Leu
785                 790                 795                 800

Thr Leu Ile Leu Ser Tyr Asn Arg Leu Arg Cys Ile Pro Pro Arg Thr
                    805                 810                 815

Phe Asp Gly Leu Lys Ser Leu Arg Leu Leu Ser Leu His Gly Asn Asp
                    820                 825                 830

Ile Ser Val Val Pro Glu Gly Ala Phe Asn Asp Leu Ser Ala Leu Ser
                    835                 840                 845

His Leu Ala Ile Gly Ala Asn Pro Leu Tyr Cys Asp Cys Asn Met Gln
850                 855                 860

Trp Leu Ser Asp Trp Val Lys Ser Glu Tyr Lys Glu Pro Gly Ile Ala
865                 870                 875                 880

Arg Cys Ala Gly Pro Gly Glu Met Ala Asp Lys Leu Leu Leu Thr Thr
                    885                 890                 895

Pro Ser Lys Lys Phe Thr Cys Gln Gly Pro Val Asp Val Asn Ile Leu
                    900                 905                 910

Ala Lys Cys Asn Pro Cys Leu Ser Asn Pro Cys Lys Asn Asp Gly Thr
                    915                 920                 925

Cys Asn Ser Asp Pro Val Asp Phe Tyr Arg Cys Thr Cys Pro Tyr Gly
                    930                 935                 940

Phe Lys Gly Gln Asp Cys Asp Val Pro Ile His Ala Cys Ile Ser Asn
945                 950                 955                 960

Pro Cys Lys His Gly Gly Thr Cys His Leu Lys Glu Gly Glu Glu Asp
                    965                 970                 975

Gly Phe Trp Cys Ile Cys Ala Asp Gly Phe Glu Gly Glu Asn Cys Glu
                    980                 985                 990

Val Asn Val Asp Cys Glu Asn Asp Cys Glu Asn Asn Ser Thr
                    995                 1000                1005

Cys Val Asp Gly Ile Asn Asn Tyr Thr Cys Leu Cys Pro Pro Glu
    1010                1015                1020

Tyr Thr Gly Glu Leu Cys Glu Glu Lys Leu Asp Phe Cys Ala Gln
    1025                1030                1035

Asp Leu Asn Pro Cys Gln His Asp Ser Lys Cys Ile Leu Thr Pro
    1040                1045                1050

Lys Gly Phe Lys Cys Asp Cys Thr Pro Gly Tyr Val Gly Glu His
    1055                1060                1065

Cys Asp Ile Asp Phe Asp Asp Cys Gln Asp Asn Lys Cys Lys Asn
    1070                1075                1080

Gly Ala His Cys Thr Asp Ala Val Asn Gly Tyr Thr Cys Ile Cys
    1085                1090                1095

Pro Glu Gly Tyr Ser Gly Leu Phe Cys Glu Phe Ser Pro Pro Met
    1100                1105                1110

Val Leu Pro Arg Thr Ser Pro Cys Asp Asn Phe Asp Cys Gln Asn
    1115                1120                1125
```

-continued

```
Gly Ala Gln Cys Ile Val Arg Ile Asn Glu Pro Ile Cys Gln Cys
    1130                1135                1140

Leu Pro Gly Tyr Gln Gly Glu Lys Cys Glu Lys Leu Val Ser Val
    1145                1150                1155

Asn Phe Ile Asn Lys Glu Ser Tyr Leu Gln Ile Pro Ser Ala Lys
    1160                1165                1170

Val Arg Pro Gln Thr Asn Ile Thr Leu Gln Ile Ala Thr Asp Glu
    1175                1180                1185

Asp Ser Gly Ile Leu Leu Tyr Lys Gly Asp Lys Asp His Ile Ala
    1190                1195                1200

Val Glu Leu Tyr Arg Gly Arg Val Arg Ala Ser Tyr Asp Thr Gly
    1205                1210                1215

Ser His Pro Ala Ser Ala Ile Tyr Ser Val Glu Thr Ile Asn Asp
    1220                1225                1230

Gly Asn Phe His Ile Val Glu Leu Leu Ala Leu Asp Gln Ser Leu
    1235                1240                1245

Ser Leu Ser Val Asp Gly Gly Asn Pro Lys Ile Ile Thr Asn Leu
    1250                1255                1260

Ser Lys Gln Ser Thr Leu Asn Phe Asp Ser Pro Leu Tyr Val Gly
    1265                1270                1275

Gly Met Pro Gly Lys Ser Asn Val Ala Ser Leu Arg Gln Ala Pro
    1280                1285                1290

Gly Gln Asn Gly Thr Ser Phe His Gly Cys Ile Arg Asn Leu Tyr
    1295                1300                1305

Ile Asn Ser Glu Leu Gln Asp Phe Gln Lys Val Pro Met Gln Thr
    1310                1315                1320

Gly Ile Leu Pro Gly Cys Glu Pro Cys His Lys Lys Val Cys Ala
    1325                1330                1335

His Gly Thr Cys Gln Pro Ser Ser Gln Ala Gly Phe Thr Cys Glu
    1340                1345                1350

Cys Gln Glu Gly Trp Met Gly Pro Leu Cys Asp Gln Arg Thr Asn
    1355                1360                1365

Asp Pro Cys Leu Gly Asn Lys Cys Val His Gly Thr Cys Leu Pro
    1370                1375                1380

Ile Asn Ala Phe Ser Tyr Ser Cys Lys Cys Leu Glu Gly His Gly
    1385                1390                1395

Gly Val Leu Cys Asp Glu Glu Asp Leu Phe Asn Pro Cys Gln
    1400                1405                1410

Ala Ile Lys Cys Lys His Gly Lys Cys Arg Leu Ser Gly Leu Gly
    1415                1420                1425

Gln Pro Tyr Cys Glu Cys Ser Gly Tyr Thr Gly Asp Ser Cys
    1430                1435                1440

Asp Arg Glu Ile Ser Cys Arg Gly Glu Arg Ile Arg Asp Tyr Tyr
    1445                1450                1455

Gln Lys Gln Gln Gly Tyr Ala Ala Cys Gln Thr Thr Lys Lys Val
    1460                1465                1470

Ser Arg Leu Glu Cys Arg Gly Gly Cys Ala Gly Gly Gln Cys Cys
    1475                1480                1485

Gly Pro Leu Arg Ser Lys Arg Arg Lys Tyr Ser Phe Glu Cys Thr
    1490                1495                1500

Asp Gly Ser Ser Phe Val Asp Glu Val Glu Lys Val Val Lys Cys
    1505                1510                1515
```

```
Gly Cys  Thr Arg Cys Val Ser
    1520              1525

<210> SEQ ID NO 3
<211> LENGTH: 1523
<212> TYPE: PRT
<213> ORGANISM: Homo sapiens

<400> SEQUENCE: 3

Met Ala Pro Gly Trp Ala Gly Val Gly Ala Val Arg Ala Arg Leu
1               5                   10                  15

Ala Leu Ala Leu Ala Leu Ala Ser Val Leu Ser Gly Pro Pro Ala Val
            20                  25                  30

Ala Cys Pro Thr Lys Cys Thr Cys Ser Ala Ala Ser Val Asp Cys His
            35                  40                  45

Gly Leu Gly Leu Arg Ala Val Pro Arg Gly Ile Pro Arg Asn Ala Glu
        50                  55                  60

Arg Leu Asp Leu Asp Arg Asn Asn Ile Thr Arg Ile Thr Lys Met Asp
65                  70                  75                  80

Phe Ala Gly Leu Lys Asn Leu Arg Val Leu His Leu Glu Asp Asn Gln
                85                  90                  95

Val Ser Val Ile Glu Arg Gly Ala Phe Gln Asp Leu Lys Gln Leu Glu
            100                 105                 110

Arg Leu Arg Leu Asn Lys Asn Lys Leu Gln Val Leu Pro Glu Leu Leu
        115                 120                 125

Phe Gln Ser Thr Pro Lys Leu Thr Arg Leu Asp Leu Ser Glu Asn Gln
    130                 135                 140

Ile Gln Gly Ile Pro Arg Lys Ala Phe Arg Gly Ile Thr Asp Val Lys
145                 150                 155                 160

Asn Leu Gln Leu Asp Asn Asn His Ile Ser Cys Ile Glu Asp Gly Ala
                165                 170                 175

Phe Arg Ala Leu Arg Asp Leu Glu Ile Leu Thr Leu Asn Asn Asn Asn
            180                 185                 190

Ile Ser Arg Ile Leu Val Thr Ser Phe Asn His Met Pro Lys Ile Arg
        195                 200                 205

Thr Leu Arg Leu His Ser Asn His Leu Tyr Cys Asp Cys His Leu Ala
    210                 215                 220

Trp Leu Ser Asp Trp Leu Arg Gln Arg Arg Thr Val Gly Gln Phe Thr
225                 230                 235                 240

Leu Cys Met Ala Pro Val His Leu Arg Gly Phe Asn Val Ala Asp Val
                245                 250                 255

Gln Lys Lys Glu Tyr Val Cys Pro Ala Pro His Ser Glu Pro Pro Ser
            260                 265                 270

Cys Asn Ala Asn Ser Ile Ser Cys Pro Ser Pro Cys Thr Cys Ser Asn
        275                 280                 285

Asn Ile Val Asp Cys Arg Gly Lys Gly Leu Met Glu Ile Pro Ala Asn
    290                 295                 300

Leu Pro Glu Gly Ile Val Glu Ile Arg Leu Glu Gln Asn Ser Ile Lys
305                 310                 315                 320

Ala Ile Pro Ala Gly Ala Phe Thr Gln Tyr Lys Lys Leu Lys Arg Ile
                325                 330                 335

Asp Ile Ser Lys Asn Gln Ile Ser Asp Ile Ala Pro Asp Ala Phe Gln
            340                 345                 350

Gly Leu Lys Ser Leu Thr Ser Leu Val Leu Tyr Gly Asn Lys Ile Thr
        355                 360                 365
```

```
Glu Ile Ala Lys Gly Leu Phe Asp Gly Leu Val Ser Leu Gln Leu Leu
    370                 375                 380

Leu Leu Asn Ala Asn Lys Ile Asn Cys Leu Arg Val Asn Thr Phe Gln
385                 390                 395                 400

Asp Leu Gln Asn Leu Asn Leu Leu Ser Leu Tyr Asp Asn Lys Leu Gln
                405                 410                 415

Thr Ile Ser Lys Gly Leu Phe Ala Pro Leu Gln Ser Ile Gln Thr Leu
            420                 425                 430

His Leu Ala Gln Asn Pro Phe Val Cys Asp Cys His Leu Lys Trp Leu
        435                 440                 445

Ala Asp Tyr Leu Gln Asp Asn Pro Ile Glu Thr Ser Gly Ala Arg Cys
450                 455                 460

Ser Ser Pro Arg Arg Leu Ala Asn Lys Arg Ile Ser Gln Ile Lys Ser
465                 470                 475                 480

Lys Lys Phe Arg Cys Ser Gly Ser Glu Asp Tyr Arg Ser Arg Phe Ser
                485                 490                 495

Ser Glu Cys Phe Met Asp Leu Val Cys Pro Glu Lys Cys Arg Cys Glu
            500                 505                 510

Gly Thr Ile Val Asp Cys Ser Asn Gln Lys Leu Val Arg Ile Pro Ser
        515                 520                 525

His Leu Pro Glu Tyr Val Thr Asp Leu Arg Leu Asn Asp Asn Glu Val
    530                 535                 540

Ser Val Leu Glu Ala Thr Gly Ile Phe Lys Lys Leu Pro Asn Leu Arg
545                 550                 555                 560

Lys Ile Asn Leu Ser Asn Asn Lys Ile Lys Glu Val Arg Glu Gly Ala
                565                 570                 575

Phe Asp Gly Ala Ala Ser Val Gln Glu Leu Met Leu Thr Gly Asn Gln
            580                 585                 590

Leu Glu Thr Val His Gly Arg Val Phe Arg Gly Leu Ser Gly Leu Lys
        595                 600                 605

Thr Leu Met Leu Arg Ser Asn Leu Ile Ser Cys Val Ser Asn Asp Thr
    610                 615                 620

Phe Ala Gly Leu Ser Ser Val Arg Leu Leu Ser Leu Tyr Asp Asn Arg
625                 630                 635                 640

Ile Thr Thr Ile Thr Pro Gly Ala Phe Thr Thr Leu Val Ser Leu Ser
                645                 650                 655

Thr Ile Asn Leu Leu Ser Asn Pro Phe Asn Cys Asn Cys His Leu Ala
            660                 665                 670

Trp Leu Gly Lys Trp Leu Arg Lys Arg Arg Ile Val Ser Gly Asn Pro
        675                 680                 685

Arg Cys Gln Lys Pro Phe Phe Leu Lys Glu Ile Pro Ile Gln Asp Val
    690                 695                 700

Ala Ile Gln Asp Phe Thr Cys Asp Gly Asn Glu Glu Ser Ser Cys Gln
705                 710                 715                 720

Leu Ser Pro Arg Cys Pro Glu Gln Cys Thr Cys Met Glu Thr Val Val
                725                 730                 735

Arg Cys Ser Asn Lys Gly Leu Arg Ala Leu Pro Arg Gly Met Pro Lys
            740                 745                 750

Asp Val Thr Glu Leu Tyr Leu Glu Gly Asn His Leu Thr Ala Val Pro
        755                 760                 765

Arg Glu Leu Ser Ala Leu Arg His Leu Thr Leu Ile Asp Leu Ser Asn
    770                 775                 780
```

```
Asn Ser Ile Ser Met Leu Thr Asn Tyr Thr Phe Ser Asn Met Ser His
785                 790                 795                 800

Leu Ser Thr Leu Ile Leu Ser Tyr Asn Arg Leu Arg Cys Ile Pro Val
        805                 810                 815

His Ala Phe Asn Gly Leu Arg Ser Leu Arg Val Leu Thr Leu His Gly
            820                 825                 830

Asn Asp Ile Ser Ser Val Pro Glu Gly Ser Phe Asn Asp Leu Thr Ser
        835                 840                 845

Leu Ser His Leu Ala Leu Gly Thr Asn Pro Leu His Cys Asp Cys Ser
    850                 855                 860

Leu Arg Trp Leu Ser Glu Trp Val Lys Ala Gly Tyr Lys Glu Pro Gly
865                 870                 875                 880

Ile Ala Arg Cys Ser Ser Pro Glu Pro Met Ala Asp Arg Leu Leu Leu
                885                 890                 895

Thr Thr Pro Thr His Arg Phe Gln Cys Lys Gly Pro Val Asp Ile Asn
            900                 905                 910

Ile Val Ala Lys Cys Asn Ala Cys Leu Ser Ser Pro Cys Lys Asn Asn
            915                 920                 925

Gly Thr Cys Thr Gln Asp Pro Val Glu Leu Tyr Arg Cys Ala Cys Pro
930                 935                 940

Tyr Ser Tyr Lys Gly Lys Asp Cys Thr Val Pro Ile Asn Thr Cys Ile
945                 950                 955                 960

Gln Asn Pro Cys Gln His Gly Gly Thr Cys His Leu Ser Asp Ser His
                965                 970                 975

Lys Asp Gly Phe Ser Cys Ser Cys Pro Leu Gly Phe Glu Gly Gln Arg
            980                 985                 990

Cys Glu Ile Asn Pro Asp Asp Cys  Glu Asp Asn Asp Cys  Glu Asn Asn
            995                 1000                1005

Ala Thr  Cys Val Asp Gly Ile  Asn Asn Tyr Val Cys  Ile Cys Pro
    1010                 1015                 1020

Pro Asn  Tyr Thr Gly Glu Leu  Cys Asp Glu Val Ile  Asp His Cys
    1025                 1030                 1035

Val Pro  Glu Leu Asn Leu Cys  Gln His Glu Ala Lys  Cys Ile Pro
    1040                 1045                 1050

Leu Asp  Lys Gly Phe Ser Cys  Glu Cys Val Pro Gly  Tyr Ser Gly
    1055                 1060                 1065

Lys Leu  Cys Glu Thr Asp Asn  Asp Asp Cys Val Ala  His Lys Cys
    1070                 1075                 1080

Arg His  Gly Ala Gln Cys Val  Asp Thr Ile Asn Gly  Tyr Thr Cys
    1085                 1090                 1095

Thr Cys  Pro Gln Gly Phe Ser  Gly Pro Phe Cys Glu  His Pro Pro
    1100                 1105                 1110

Pro Met  Val Leu Leu Gln Thr  Ser Pro Cys Asp Gln  Tyr Glu Cys
    1115                 1120                 1125

Gln Asn  Gly Ala Gln Cys Ile  Val Val Gln Gln Glu  Pro Thr Cys
    1130                 1135                 1140

Arg Cys  Pro Pro Gly Phe Ala  Gly Pro Arg Cys Glu  Lys Leu Ile
    1145                 1150                 1155

Thr Val  Asn Phe Val Gly Lys  Asp Ser Tyr Val Glu  Leu Ala Ser
    1160                 1165                 1170

Ala Lys  Val Arg Pro Gln Ala  Asn Ile Ser Leu Gln  Val Ala Thr
    1175                 1180                 1185

Asp Lys  Asp Asn Gly Ile Leu  Leu Tyr Lys Gly Asp  Asn Asp Pro
```

```
                1190               1195               1200
Leu Ala Leu Glu Leu Tyr Gln Gly His Val Arg Leu Val Tyr Asp
    1205               1210               1215

Ser Leu Ser Ser Pro Pro Thr Thr Val Tyr Ser Val Glu Thr Val
    1220               1225               1230

Asn Asp Gly Gln Phe His Ser Val Glu Leu Val Thr Leu Asn Gln
    1235               1240               1245

Thr Leu Asn Leu Val Val Asp Lys Gly Thr Pro Lys Ser Leu Gly
    1250               1255               1260

Lys Leu Gln Lys Gln Pro Ala Val Gly Ile Asn Ser Pro Leu Tyr
    1265               1270               1275

Leu Gly Gly Ile Pro Thr Ser Thr Gly Leu Ser Ala Leu Arg Gln
    1280               1285               1290

Gly Thr Asp Arg Pro Leu Gly Gly Phe His Gly Cys Ile His Glu
    1295               1300               1305

Val Arg Ile Asn Asn Glu Leu Gln Asp Phe Lys Ala Leu Pro Pro
    1310               1315               1320

Gln Ser Leu Gly Val Ser Pro Gly Cys Lys Ser Cys Thr Val Cys
    1325               1330               1335

Lys His Gly Leu Cys Arg Ser Val Glu Lys Asp Ser Val Val Cys
    1340               1345               1350

Glu Cys Arg Pro Gly Trp Thr Gly Pro Leu Cys Asp Gln Glu Ala
    1355               1360               1365

Arg Asp Pro Cys Leu Gly His Arg Cys His His Gly Lys Cys Val
    1370               1375               1380

Ala Thr Gly Thr Ser Tyr Met Cys Lys Cys Ala Glu Gly Tyr Gly
    1385               1390               1395

Gly Asp Leu Cys Asp Asn Lys Asn Asp Ser Ala Asn Ala Cys Ser
    1400               1405               1410

Ala Phe Lys Cys His His Gly Gln Cys His Ile Ser Asp Gln Gly
    1415               1420               1425

Glu Pro Tyr Cys Leu Cys Gln Pro Gly Phe Ser Gly Glu His Cys
    1430               1435               1440

Gln Gln Glu Asn Pro Cys Leu Gly Gln Val Val Arg Glu Val Ile
    1445               1450               1455

Arg Arg Gln Lys Gly Tyr Ala Ser Cys Ala Thr Ala Ser Lys Val
    1460               1465               1470

Pro Ile Met Glu Cys Arg Gly Gly Cys Gly Pro Gln Cys Cys Gln
    1475               1480               1485

Pro Thr Arg Ser Lys Arg Arg Lys Tyr Val Phe Gln Cys Thr Asp
    1490               1495               1500

Gly Ser Ser Phe Val Glu Glu Val Glu Arg His Leu Glu Cys Gly
    1505               1510               1515

Cys Leu Ala Cys Ser
    1520

<210> SEQ ID NO 4
<211> LENGTH: 1606
<212> TYPE: PRT
<213> ORGANISM: Homo sapiens

<400> SEQUENCE: 4

Met Ile Ala Glu Pro Ala His Phe Tyr Leu Phe Gly Leu Ile Cys Leu
1               5                   10                  15
```

```
Cys Ser Gly Ser Arg Leu Arg Gln Glu Asp Phe Pro Arg Ile Val
             20                  25                  30

Glu His Pro Ser Asp Leu Ile Val Ser Lys Gly Glu Pro Ala Thr Leu
         35                  40                  45

Asn Cys Lys Ala Glu Gly Arg Pro Thr Pro Thr Ile Glu Trp Tyr Lys
 50                  55                  60

Gly Gly Glu Arg Val Glu Thr Asp Lys Asp Pro Arg Ser His Arg
 65                  70                  75                  80

Met Leu Leu Pro Ser Gly Ser Leu Phe Phe Leu Arg Ile Val His Gly
                 85                  90                  95

Arg Lys Ser Arg Pro Asp Glu Gly Val Tyr Val Cys Val Ala Arg Asn
             100                 105                 110

Tyr Leu Gly Glu Ala Val Ser His Asn Ala Ser Leu Glu Val Ala Ile
         115                 120                 125

Leu Arg Asp Asp Phe Arg Gln Asn Pro Ser Asp Val Met Val Ala Val
     130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                 165                 170                 175

Glu Arg Ile Thr Ile Arg Gly Gly Lys Leu Met Ile Thr Tyr Thr Arg
             180                 185                 190

Lys Ser Asp Ala Gly Lys Tyr Val Cys Val Gly Thr Asn Met Val Gly
         195                 200                 205

Glu Arg Glu Ser Glu Val Ala Glu Leu Thr Val Leu Glu Arg Pro Ser
     210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                 245                 250                 255

Arg Lys Asp Asp Gly Glu Leu Pro Lys Ser Arg Tyr Glu Ile Arg Asp
             260                 265                 270

Asp His Thr Leu Lys Ile Arg Lys Val Thr Ala Gly Asp Met Gly Ser
         275                 280                 285

Tyr Thr Cys Val Ala Glu Asn Met Val Gly Lys Ala Glu Ala Ser Ala
     290                 295                 300

Thr Leu Thr Val Gln Val Gly Ser Glu Pro Pro His Phe Val Val Lys
305                 310                 315                 320

Pro Arg Asp Gln Val Val Ala Leu Gly Arg Thr Val Thr Phe Gln Cys
                 325                 330                 335

Glu Ala Thr Gly Asn Pro Gln Pro Ala Ile Phe Trp Arg Arg Glu Gly
             340                 345                 350

Ser Gln Asn Leu Leu Phe Ser Tyr Gln Pro Pro Gln Ser Ser Ser Arg
         355                 360                 365

Phe Ser Val Ser Gln Thr Gly Asp Leu Thr Ile Thr Asn Val Gln Arg
     370                 375                 380

Ser Asp Val Gly Tyr Tyr Ile Cys Gln Thr Leu Asn Val Ala Gly Ser
385                 390                 395                 400

Ile Ile Thr Lys Ala Tyr Leu Glu Val Thr Asp Val Ile Ala Asp Arg
                 405                 410                 415

Pro Pro Pro Val Ile Arg Gln Gly Pro Val Asn Gln Thr Val Ala Val
             420                 425                 430

Asp Gly Thr Phe Val Leu Ser Cys Val Ala Thr Gly Ser Pro Val Pro
```

```
                435                 440                 445
Thr Ile Leu Trp Arg Lys Asp Gly Val Leu Val Ser Thr Gln Asp Ser
450                 455                 460

Arg Ile Lys Gln Leu Glu Asn Gly Val Leu Gln Ile Arg Tyr Ala Lys
465                 470                 475                 480

Leu Gly Asp Thr Gly Arg Tyr Thr Cys Ile Ala Ser Thr Pro Ser Gly
                485                 490                 495

Glu Ala Thr Trp Ser Ala Tyr Ile Glu Val Gln Glu Phe Gly Val Pro
                500                 505                 510

Val Gln Pro Pro Arg Pro Thr Asp Pro Asn Leu Ile Pro Ser Ala Pro
            515                 520                 525

Ser Lys Pro Glu Val Thr Asp Val Ser Arg Asn Thr Val Thr Leu Ser
530                 535                 540

Trp Gln Pro Asn Leu Asn Ser Gly Ala Thr Pro Thr Ser Tyr Ile Ile
545                 550                 555                 560

Glu Ala Phe Ser His Ala Ser Gly Ser Ser Trp Gln Thr Val Ala Glu
                565                 570                 575

Asn Val Lys Thr Glu Thr Ser Ala Ile Lys Gly Leu Lys Pro Asn Ala
                580                 585                 590

Ile Tyr Leu Phe Leu Val Arg Ala Ala Asn Ala Tyr Gly Ile Ser Asp
                595                 600                 605

Pro Ser Gln Ile Ser Asp Pro Val Lys Thr Gln Asp Val Leu Pro Thr
610                 615                 620

Ser Gln Gly Val Asp His Lys Val Gln Arg Glu Leu Gly Asn Ala
625                 630                 635                 640

Val Leu His Leu His Asn Pro Thr Val Leu Ser Ser Ser Ile Glu
                645                 650                 655

Val His Trp Thr Val Asp Gln Gln Ser Gln Tyr Ile Gln Gly Tyr Lys
                660                 665                 670

Ile Leu Tyr Arg Pro Ser Gly Ala Asn His Gly Glu Ser Asp Trp Leu
                675                 680                 685

Val Phe Glu Val Arg Thr Pro Ala Lys Asn Ser Val Val Ile Pro Asp
690                 695                 700

Leu Arg Lys Gly Val Asn Tyr Glu Ile Lys Ala Arg Pro Phe Phe Asn
705                 710                 715                 720

Glu Phe Gln Gly Ala Asp Ser Glu Ile Lys Phe Ala Lys Thr Leu Glu
                725                 730                 735

Glu Ala Pro Ser Ala Pro Pro Gln Gly Val Thr Val Ser Lys Asn Asp
                740                 745                 750

Gly Asn Gly Thr Ala Ile Leu Val Ser Trp Gln Pro Pro Glu Asp
                755                 760                 765

Thr Gln Asn Gly Met Val Gln Glu Tyr Lys Val Trp Cys Leu Gly Asn
            770                 775                 780

Glu Thr Arg Tyr His Ile Asn Lys Thr Val Asp Gly Ser Thr Phe Ser
785                 790                 795                 800

Val Val Ile Pro Phe Leu Val Pro Gly Ile Arg Tyr Ser Val Glu Val
                805                 810                 815

Ala Ala Ser Thr Gly Ala Gly Ser Gly Val Lys Ser Glu Pro Gln Phe
                820                 825                 830

Ile Gln Leu Asp Ala His Gly Asn Pro Val Ser Pro Glu Asp Gln Val
                835                 840                 845

Ser Leu Ala Gln Gln Ile Ser Asp Val Val Lys Gln Pro Ala Phe Ile
850                 855                 860
```

```
Ala Gly Ile Gly Ala Ala Cys Trp Ile Ile Leu Met Val Phe Ser Ile
865                 870                 875                 880

Trp Leu Tyr Arg His Arg Lys Arg Asn Gly Leu Thr Ser Thr Tyr
            885                 890                 895

Ala Gly Ile Arg Lys Val Thr Tyr Gln Arg Gly Gly Glu Ala Val Ser
            900                 905                 910

Ser Gly Gly Arg Pro Gly Leu Leu Asn Ile Ser Glu Pro Ala Ala Gln
            915                 920                 925

Pro Trp Leu Ala Asp Thr Trp Pro Asn Thr Gly Asn Asn His Asn Asp
            930                 935                 940

Cys Ser Ile Ser Cys Cys Thr Ala Gly Asn Gly Asn Ser Asp Ser Asn
945                 950                 955                 960

Leu Thr Thr Tyr Ser Arg Pro Ala Asp Cys Ile Ala Asn Tyr Asn Asn
            965                 970                 975

Gln Leu Asp Asn Lys Gln Thr Asn Leu Met Leu Pro Glu Ser Thr Val
            980                 985                 990

Tyr Gly Asp Val Asp Leu Ser Asn Lys Ile Asn Glu Met Lys Thr Phe
            995                 1000                1005

Asn Ser Pro Asn Leu Lys Asp Gly Arg Phe Val Asn Pro Ser Gly
1010                1015                1020

Gln Pro Thr Pro Tyr Ala Thr Thr Gln Leu Ile Gln Ser Asn Leu
1025                1030                1035

Ser Asn Asn Met Asn Asn Gly Ser Gly Asp Ser Gly Glu Lys His
1040                1045                1050

Trp Lys Pro Leu Gly Gln Gln Lys Gln Glu Val Ala Pro Val Gln
1055                1060                1065

Tyr Asn Ile Val Glu Gln Asn Lys Leu Asn Lys Asp Tyr Arg Ala
1070                1075                1080

Asn Asp Thr Val Pro Pro Thr Ile Pro Tyr Asn Gln Ser Tyr Asp
1085                1090                1095

Gln Asn Thr Gly Gly Ser Tyr Asn Ser Ser Asp Arg Gly Ser Ser
1100                1105                1110

Thr Ser Gly Ser Gln Gly His Lys Lys Gly Ala Arg Thr Pro Lys
1115                1120                1125

Val Pro Lys Gln Gly Gly Met Asn Trp Ala Asp Leu Leu Pro Pro
1130                1135                1140

Pro Pro Ala His Pro Pro His Ser Asn Ser Glu Glu Tyr Asn
1145                1150                1155

Ile Ser Val Asp Glu Ser Tyr Asp Gln Glu Met Pro Cys Pro Val
1160                1165                1170

Pro Pro Ala Arg Met Tyr Leu Gln Gln Asp Glu Leu Glu Glu Glu
1175                1180                1185

Glu Asp Glu Arg Gly Pro Thr Pro Pro Val Arg Gly Ala Ala Ser
1190                1195                1200

Ser Pro Ala Ala Val Ser Tyr Ser His Gln Ser Thr Ala Thr Leu
1205                1210                1215

Thr Pro Ser Pro Gln Glu Glu Leu Gln Pro Met Leu Gln Asp Cys
1220                1225                1230

Pro Glu Glu Thr Gly His Met Gln His Gln Pro Asp Arg Arg Arg
1235                1240                1245

Gln Pro Val Ser Pro Pro Pro Pro Arg Pro Ile Ser Pro Pro
1250                1255                1260
```

His Thr Tyr Gly Tyr Ile Ser Gly Pro Leu Val Ser Asp Met Asp
1265             1270            1275

Thr Asp Ala Pro Glu Glu Glu Asp Glu Ala Asp Met Glu Val
1280            1285            1290

Ala Lys Met Gln Thr Arg Arg Leu Leu Leu Arg Gly Leu Glu Gln
1295            1300            1305

Thr Pro Ala Ser Ser Val Gly Asp Leu Glu Ser Val Thr Gly
1310            1315            1320

Ser Met Ile Asn Gly Trp Gly Ser Ala Ser Glu Glu Asp Asn Ile
1325            1330            1335

Ser Ser Gly Arg Ser Ser Val Ser Ser Ser Asp Gly Ser Phe Phe
1340            1345            1350

Thr Asp Ala Asp Phe Ala Gln Ala Val Ala Ala Ala Glu Tyr
1355            1360            1365

Ala Gly Leu Lys Val Ala Arg Arg Gln Met Gln Asp Ala Ala Gly
1370            1375            1380

Arg Arg His Phe His Ala Ser Gln Cys Pro Arg Pro Thr Ser Pro
1385            1390            1395

Val Ser Thr Asp Ser Asn Met Ser Ala Ala Val Met Gln Lys Thr
1400            1405            1410

Arg Pro Ala Lys Lys Leu Lys His Gln Pro Gly His Leu Arg Arg
1415            1420            1425

Glu Thr Tyr Thr Asp Asp Leu Pro Pro Pro Pro Val Pro Pro Pro
1430            1435            1440

Ala Ile Lys Ser Pro Thr Ala Gln Ser Lys Thr Gln Leu Glu Val
1445            1450            1455

Arg Pro Val Val Pro Lys Leu Pro Ser Met Asp Ala Arg Thr
1460            1465            1470

Asp Arg Ser Ser Asp Arg Lys Gly Ser Ser Tyr Lys Gly Arg Glu
1475            1480            1485

Val Leu Asp Gly Arg Gln Val Val Asp Met Arg Thr Asn Pro Gly
1490            1495            1500

Asp Pro Arg Glu Ala Gln Glu Gln Gln Asn Asp Gly Lys Gly Arg
1505            1510            1515

Gly Asn Lys Ala Ala Lys Arg Asp Leu Pro Pro Ala Lys Thr His
1520            1525            1530

Leu Ile Gln Glu Asp Ile Leu Pro Tyr Cys Arg Pro Thr Phe Pro
1535            1540            1545

Thr Ser Asn Asn Pro Arg Asp Pro Ser Ser Ser Ser Met Ser
1550            1555            1560

Ser Arg Gly Ser Gly Ser Arg Gln Arg Glu Gln Ala Asn Val Gly
1565            1570            1575

Arg Arg Asn Ile Ala Glu Met Gln Val Leu Gly Gly Tyr Glu Arg
1580            1585            1590

Gly Glu Asp Asn Asn Glu Glu Leu Glu Glu Thr Glu Ser
1595            1600            1605

<210> SEQ ID NO 5
<211> LENGTH: 1378
<212> TYPE: PRT
<213> ORGANISM: Homo sapiens

<400> SEQUENCE: 5

Met Ser Leu Leu Met Phe Thr Gln Leu Leu Leu Cys Gly Phe Leu Tyr
1               5                   10                  15

-continued

Val Arg Val Asp Gly Ser Arg Leu Arg Gln Glu Asp Phe Pro Pro Arg
            20                  25                  30

Ile Val Glu His Pro Ser Asp Val Ile Val Ser Lys Gly Glu Pro Thr
            35                  40                  45

Thr Leu Asn Cys Lys Ala Glu Gly Arg Pro Thr Pro Thr Ile Glu Trp
50                  55                  60

Tyr Lys Asp Gly Glu Arg Val Glu Thr Asp Lys Asp Asp Pro Arg Ser
65                  70                  75                  80

His Arg Met Leu Leu Pro Ser Gly Ser Leu Phe Phe Leu Arg Ile Val
                85                  90                  95

His Gly Arg Arg Ser Lys Pro Asp Glu Gly Ser Tyr Val Cys Val Ala
            100                 105                 110

Arg Asn Tyr Leu Gly Glu Ala Val Ser Arg Asn Ala Ser Leu Glu Val
            115                 120                 125

Ala Leu Leu Arg Asp Asp Phe Arg Gln Asn Pro Thr Asp Val Val Val
130                 135                 140

Ala Ala Gly Glu Pro Ala Ile Leu Glu Cys Gln Pro Pro Arg Gly His
145                 150                 155                 160

Pro Glu Pro Thr Ile Tyr Trp Lys Lys Asp Lys Val Arg Ile Asp Asp
                165                 170                 175

Lys Glu Glu Arg Ile Ser Ile Arg Gly Gly Lys Leu Met Ile Ser Asn
            180                 185                 190

Thr Arg Lys Ser Asp Ala Gly Met Tyr Thr Cys Val Gly Thr Asn Met
            195                 200                 205

Val Gly Glu Arg Asp Ser Asp Pro Ala Glu Leu Thr Val Phe Glu Arg
            210                 215                 220

Pro Thr Phe Leu Arg Arg Pro Ile Asn Gln Val Val Leu Glu Glu Glu
225                 230                 235                 240

Ala Val Glu Phe Arg Cys Gln Val Gln Gly Asp Pro Gln Pro Thr Val
                245                 250                 255

Arg Trp Lys Lys Asp Asp Ala Asp Leu Pro Arg Gly Arg Tyr Asp Ile
            260                 265                 270

Lys Asp Asp Tyr Thr Leu Arg Ile Lys Lys Thr Met Ser Thr Asp Glu
            275                 280                 285

Gly Thr Tyr Met Cys Ile Ala Glu Asn Arg Val Gly Lys Met Glu Ala
290                 295                 300

Ser Ala Thr Leu Thr Val Arg Ala Pro Pro Gln Phe Val Val Arg Pro
305                 310                 315                 320

Arg Asp Gln Ile Val Ala Gln Gly Arg Thr Val Thr Phe Pro Cys Glu
                325                 330                 335

Thr Lys Gly Asn Pro Gln Pro Ala Val Phe Trp Gln Lys Glu Gly Ser
            340                 345                 350

Gln Asn Leu Leu Phe Pro Asn Gln Pro Gln Gln Pro Asn Ser Arg Cys
            355                 360                 365

Ser Val Ser Pro Thr Gly Asp Leu Thr Ile Thr Asn Ile Gln Arg Ser
370                 375                 380

Asp Ala Gly Tyr Tyr Ile Cys Gln Ala Leu Thr Val Ala Gly Ser Ile
385                 390                 395                 400

Leu Ala Lys Ala Gln Leu Glu Val Thr Asp Val Leu Thr Asp Arg Pro
                405                 410                 415

Pro Pro Ile Ile Leu Gln Gly Pro Ala Asn Gln Thr Leu Ala Val Asp
            420                 425                 430

-continued

```
Gly Thr Ala Leu Leu Lys Cys Lys Ala Thr Gly Asp Pro Leu Pro Val
            435                 440                 445

Ile Ser Trp Leu Lys Glu Gly Phe Thr Phe Pro Gly Arg Asp Pro Arg
450                 455                 460

Ala Thr Ile Gln Glu Gln Gly Thr Leu Gln Ile Lys Asn Leu Arg Ile
465                 470                 475                 480

Ser Asp Thr Gly Thr Tyr Thr Cys Val Ala Thr Ser Ser Ser Gly Glu
                485                 490                 495

Thr Ser Trp Ser Ala Val Leu Asp Val Thr Glu Ser Gly Ala Thr Ile
            500                 505                 510

Ser Lys Asn Tyr Asp Leu Ser Asp Leu Pro Gly Pro Pro Ser Lys Pro
        515                 520                 525

Gln Val Thr Asp Val Thr Lys Asn Ser Val Thr Leu Ser Trp Gln Pro
    530                 535                 540

Gly Thr Pro Gly Thr Leu Pro Ala Ser Ala Tyr Ile Ile Glu Ala Phe
545                 550                 555                 560

Ser Gln Ser Val Ser Asn Ser Trp Gln Thr Val Ala Asn His Val Lys
                565                 570                 575

Thr Thr Leu Tyr Thr Val Arg Gly Leu Arg Pro Asn Thr Ile Tyr Leu
            580                 585                 590

Phe Met Val Arg Ala Ile Asn Pro Gln Gly Leu Ser Asp Pro Ser Pro
        595                 600                 605

Met Ser Asp Pro Val Arg Thr Gln Asp Ile Ser Pro Pro Ala Gln Gly
    610                 615                 620

Val Asp His Arg Gln Val Gln Lys Glu Leu Gly Asp Val Leu Val Arg
625                 630                 635                 640

Leu His Asn Pro Val Val Leu Thr Pro Thr Thr Val Gln Val Thr Trp
                645                 650                 655

Thr Val Asp Arg Gln Pro Gln Phe Ile Gln Gly Tyr Arg Val Met Tyr
            660                 665                 670

Arg Gln Thr Ser Gly Leu Gln Ala Thr Ser Ser Trp Gln Asn Leu Asp
        675                 680                 685

Ala Lys Val Pro Thr Glu Arg Ser Ala Val Leu Val Asn Leu Lys Lys
    690                 695                 700

Gly Val Thr Tyr Glu Ile Lys Val Arg Pro Tyr Phe Asn Glu Phe Gln
705                 710                 715                 720

Gly Met Asp Ser Glu Ser Lys Thr Val Arg Thr Thr Glu Glu Ala Pro
                725                 730                 735

Ser Ala Pro Pro Gln Ser Val Thr Val Leu Thr Val Gly Ser Tyr Asn
            740                 745                 750

Ser Thr Ser Ile Ser Val Ser Trp Asp Pro Pro Pro Pro Asp His Gln
        755                 760                 765

Asn Gly Ile Ile Gln Glu Tyr Lys Ile Trp Cys Leu Gly Asn Glu Thr
    770                 775                 780

Arg Phe His Ile Asn Lys Thr Val Asp Ala Ala Ile Arg Ser Val Ile
785                 790                 795                 800

Ile Gly Gly Leu Phe Pro Gly Ile Gln Tyr Arg Val Glu Val Ala Ala
                805                 810                 815

Ser Thr Ser Ala Gly Val Gly Val Lys Ser Glu Pro Gln Pro Ile Ile
            820                 825                 830

Ile Gly Arg Arg Asn Glu Val Val Ile Thr Glu Asn Asn Asn Ser Ile
        835                 840                 845

Thr Glu Gln Ile Thr Asp Val Val Lys Gln Pro Ala Phe Ile Ala Gly
```

```
                850                 855                 860
Ile Gly Gly Ala Cys Trp Val Ile Leu Met Gly Phe Ser Ile Trp Leu
865                 870                 875                 880

Tyr Trp Arg Arg Lys Lys Arg Lys Gly Leu Ser Asn Tyr Ala Val Thr
                885                 890                 895

Phe Gln Arg Gly Asp Gly Gly Leu Met Ser Asn Gly Ser Arg Pro Gly
                900                 905                 910

Leu Leu Asn Ala Gly Asp Pro Ser Tyr Pro Trp Leu Ala Asp Ser Trp
            915                 920                 925

Pro Ala Thr Ser Leu Pro Val Asn Asn Ser Asn Ser Gly Pro Asn Glu
        930                 935                 940

Ile Gly Asn Phe Gly Arg Gly Asp Val Leu Pro Pro Val Pro Gly Gln
945                 950                 955                 960

Gly Asp Lys Thr Ala Thr Met Leu Ser Asp Gly Ala Ile Tyr Ser Ser
                965                 970                 975

Ile Asp Phe Thr Thr Lys Thr Ser Tyr Asn Ser Ser Ser Gln Ile Thr
                980                 985                 990

Gln Ala Thr Pro Tyr Ala Thr Thr  Gln Ile Leu His Ser  Asn Ser Ile
            995                 1000               1005

His Glu  Leu Ala Val Asp Leu  Pro Asp Pro Gln Trp  Lys Ser Ser
        1010               1015                1020

Ile Gln  Gln Lys Thr Asp Leu  Met Gly Phe Gly Tyr  Ser Leu Pro
        1025               1030                1035

Asp Gln  Asn Lys Gly Asn Asn  Gly Gly Lys Gly Lys  Lys Lys
        1040               1045                1050

Lys Asn  Lys Asn Ser Ser Lys  Pro Gln Lys Asn Asn  Gly Ser Thr
        1055               1060                1065

Trp Ala  Asn Val Pro Leu Pro  Pro Pro Val Gln Pro  Leu Pro
        1070               1075                1080

Gly Thr  Glu Leu Glu His Tyr  Ala Val Glu Gln Gln  Glu Asn Gly
        1085               1090                1095

Tyr Asp  Ser Asp Ser Trp Cys  Pro Pro Leu Pro Val  Gln Thr Tyr
        1100               1105                1110

Leu His  Gln Gly Leu Glu Asp  Glu Leu Glu Glu Asp  Asp Asp Arg
        1115               1120                1125

Val Pro  Thr Pro Pro Val Arg  Gly Val Ala Ser Ser  Pro Ala Ile
        1130               1135                1140

Ser Phe  Gly Gln Gln Ser Thr  Ala Thr Leu Thr Pro  Ser Pro Arg
        1145               1150                1155

Glu Glu  Met Gln Pro Met Leu  Gln Ala His Leu Asp  Glu Leu Thr
        1160               1165                1170

Arg Ala  Tyr Gln Phe Asp Ile  Ala Lys Gln Thr Trp  His Ile Gln
        1175               1180                1185

Ser Asn  Asn Gln Pro Pro Gln  Pro Pro Val Pro Pro  Leu Gly Tyr
        1190               1195                1200

Val Ser  Gly Ala Leu Ile Ser  Asp Leu Glu Thr Asp  Val Ala Asp
        1205               1210                1215

Asp Asp  Ala Asp Asp Glu Glu  Glu Ala Leu Glu Ile  Pro Arg Pro
        1220               1225                1230

Leu Arg  Ala Leu Asp Gln Thr  Pro Gly Ser Ser Met  Asp Asn Leu
        1235               1240                1245

Asp Ser  Ser Val Thr Gly Lys  Ala Phe Thr Ser Ser  Gln Arg Pro
        1250               1255                1260
```

```
Arg Pro Thr Ser Pro Phe Ser Thr Asp Ser Asn Thr Ser Ala Ala
    1265                1270                1275

Leu Ser Gln Ser Gln Arg Pro Arg Pro Thr Lys Lys His Lys Gly
    1280                1285                1290

Gly Arg Met Asp Gln Gln Pro Ala Leu Pro His Arg Arg Glu Gly
    1295                1300                1305

Met Thr Asp Glu Glu Ala Leu Val Pro Tyr Ser Lys Pro Ser Phe
    1310                1315                1320

Pro Ser Pro Gly Gly His Ser Ser Gly Thr Ala Ser Ser Lys
    1325                1330                1335

Gly Ser Thr Gly Pro Arg Lys Thr Glu Val Leu Arg Ala Gly His
    1340                1345                1350

Gln Arg Asn Ala Ser Asp Leu Leu Asp Ile Gly Tyr Met Gly Ser
    1355                1360                1365

Asn Ser Gln Gly Gln Phe Thr Gly Glu Leu
    1370                1375

<210> SEQ ID NO 6
<211> LENGTH: 1386
<212> TYPE: PRT
<213> ORGANISM: Homo sapiens

<400> SEQUENCE: 6

Met Leu Arg Tyr Leu Leu Lys Thr Leu Leu Gln Met Asn Leu Phe Ala
1               5                   10                  15

Asp Ser Leu Ala Gly Asp Ile Ser Asn Ser Ser Glu Leu Leu Leu Gly
                20                  25                  30

Phe Asn Ser Ser Leu Ala Ala Leu Asn His Thr Leu Leu Pro Pro Gly
            35                  40                  45

Asp Pro Ser Leu Asn Gly Ser Arg Val Gly Pro Glu Asp Ala Met Pro
        50                  55                  60

Arg Ile Val Glu Gln Pro Pro Asp Leu Leu Val Ser Arg Gly Glu Pro
65                  70                  75                  80

Ala Thr Leu Pro Cys Arg Ala Glu Gly Arg Pro Arg Pro Asn Ile Glu
                85                  90                  95

Trp Tyr Lys Asn Gly Ala Arg Val Ala Thr Val Arg Glu Asp Pro Arg
            100                 105                 110

Ala His Arg Leu Leu Leu Pro Ser Gly Ala Leu Phe Phe Pro Arg Ile
        115                 120                 125

Val His Gly Arg Arg Ala Arg Pro Asp Glu Gly Val Tyr Thr Cys Val
    130                 135                 140

Ala Arg Asn Tyr Leu Gly Ala Ala Ala Ser Arg Asn Ala Ser Leu Glu
145                 150                 155                 160

Val Ala Val Leu Arg Asp Asp Phe Arg Gln Ser Pro Gly Asn Val Val
                165                 170                 175

Val Ala Val Gly Glu Pro Ala Val Leu Glu Cys Val Pro Pro Arg Gly
            180                 185                 190

His Pro Glu Pro Ser Val Ser Trp Arg Lys Asp Gly Ala Arg Leu Lys
        195                 200                 205

Glu Glu Glu Gly Arg Ile Thr Ile Arg Gly Gly Lys Leu Met Met Ser
    210                 215                 220

His Thr Leu Lys Ser Asp Ala Gly Met Tyr Val Cys Val Ala Ser Asn
225                 230                 235                 240

Met Ala Gly Glu Arg Glu Ser Ala Ala Ala Glu Val Met Val Leu Glu
```

```
                245                 250                 255
Arg Pro Ser Phe Leu Arg Arg Pro Val Asn Gln Val Val Leu Ala Asp
            260                 265                 270

Ala Pro Val Thr Phe Leu Cys Glu Val Lys Gly Asp Pro Pro Arg
            275                 280                 285

Leu Arg Trp Arg Lys Glu Asp Gly Glu Leu Pro Thr Gly Arg Tyr Glu
            290                 295                 300

Ile Arg Ser Asp His Ser Leu Trp Ile Gly His Val Ser Ala Glu Asp
305                 310                 315                 320

Glu Gly Thr Tyr Thr Cys Val Ala Glu Asn Ser Val Gly Arg Ala Glu
                325                 330                 335

Ala Ser Gly Ser Leu Ser Val His Val Pro Pro Gln Leu Val Thr Gln
            340                 345                 350

Pro Gln Asp Gln Met Ala Ala Pro Gly Glu Ser Val Ala Phe Gln Cys
            355                 360                 365

Glu Thr Lys Gly Asn Pro Pro Ala Ile Phe Trp Gln Lys Glu Gly
        370                 375                 380

Ser Gln Val Leu Leu Phe Pro Ser Gln Ser Leu Gln Pro Thr Gly Arg
385                 390                 395                 400

Phe Ser Val Ser Pro Arg Gly Gln Leu Asn Ile Thr Ala Val Gln Arg
                405                 410                 415

Gly Asp Ala Gly Tyr Tyr Val Cys Gln Ala Val Ser Val Ala Gly Ser
            420                 425                 430

Ile Leu Ala Lys Ala Leu Leu Glu Ile Lys Gly Ala Ser Leu Asp Gly
            435                 440                 445

Leu Pro Pro Val Ile Leu Gln Gly Pro Ala Asn Gln Thr Leu Val Leu
        450                 455                 460

Gly Ser Ser Val Trp Leu Pro Cys Arg Val Thr Gly Asn Pro Gln Pro
465                 470                 475                 480

Ser Val Arg Trp Lys Lys Asp Gly Gln Trp Leu Gln Gly Asp Asp Leu
                485                 490                 495

Gln Phe Lys Thr Met Ala Asn Gly Thr Leu Tyr Ile Ala Asn Val Gln
            500                 505                 510

Glu Met Asp Met Gly Phe Tyr Ser Cys Val Ala Lys Ser Ser Thr Gly
            515                 520                 525

Glu Ala Thr Trp Ser Gly Trp Leu Lys Met Arg Glu Asp Trp Gly Val
            530                 535                 540

Ser Pro Asp Pro Pro Thr Glu Pro Ser Ser Pro Gly Ala Pro Ser
545                 550                 555                 560

Gln Pro Val Val Thr Glu Ile Thr Lys Asn Ser Ile Thr Leu Thr Trp
                565                 570                 575

Lys Pro Asn Pro Gln Thr Gly Ala Ala Val Thr Ser Tyr Val Ile Glu
            580                 585                 590

Ala Phe Ser Pro Ala Ala Gly Asn Thr Trp Arg Thr Val Ala Asp Gly
            595                 600                 605

Val Gln Leu Glu Thr His Thr Val Ser Gly Leu Gln Pro Asn Thr Ile
            610                 615                 620

Tyr Leu Phe Leu Val Arg Ala Val Gly Ala Trp Gly Leu Ser Glu Pro
625                 630                 635                 640

Ser Pro Val Ser Glu Pro Val Arg Thr Gln Asp Ser Pro Ser Arg
                645                 650                 655

Pro Val Glu Asp Pro Trp Arg Gly Gln Gln Gly Leu Ala Glu Val Ala
            660                 665                 670
```

-continued

Val Arg Leu Gln Glu Pro Ile Val Leu Gly Pro Arg Thr Leu Gln Val
        675                 680                 685

Ser Trp Thr Val Asp Gly Pro Val Gln Leu Val Gln Gly Phe Arg Val
690                 695                 700

Ser Trp Arg Val Ala Gly Pro Glu Gly Gly Ser Trp Thr Met Leu Asp
705                 710                 715                 720

Leu Gln Ser Pro Ser Gln Gln Ser Thr Val Leu Arg Gly Leu Pro Pro
                725                 730                 735

Gly Thr Gln Ile Gln Ile Lys Val Gln Ala Gln Gly Gln Glu Gly Leu
            740                 745                 750

Gly Ala Glu Ser Leu Ser Val Thr Arg Ser Ile Pro Glu Glu Ala Pro
            755                 760                 765

Ser Gly Pro Pro Gln Gly Val Ala Val Ala Leu Gly Gly Asp Gly Asn
        770                 775                 780

Ser Ser Ile Thr Val Ser Trp Glu Pro Pro Leu Pro Ser Gln Gln Asn
785                 790                 795                 800

Gly Val Ile Thr Glu Tyr Gln Ile Trp Cys Leu Gly Asn Glu Ser Arg
                805                 810                 815

Phe His Leu Asn Arg Ser Ala Ala Gly Trp Ala Arg Ser Ala Met Leu
                820                 825                 830

Arg Gly Leu Val Pro Gly Leu Leu Tyr Arg Thr Leu Val Ala Ala Ala
            835                 840                 845

Thr Ser Ala Gly Val Gly Val Pro Ser Ala Pro Val Leu Val Gln Leu
850                 855                 860

Pro Ser Pro Pro Asp Leu Glu Pro Gly Leu Glu Val Gly Ala Gly Leu
865                 870                 875                 880

Ala Val Arg Leu Ala Arg Val Leu Arg Glu Pro Ala Phe Leu Ala Gly
                885                 890                 895

Ser Gly Ala Ala Cys Gly Ala Leu Leu Leu Gly Leu Cys Ala Ala Leu
            900                 905                 910

Tyr Trp Arg Arg Lys Gln Arg Lys Glu Leu Ser His Tyr Thr Ala Ser
        915                 920                 925

Phe Ala Tyr Thr Pro Ala Val Ser Phe Pro His Ser Glu Gly Leu Ser
930                 935                 940

Gly Ala Ser Ser Arg Pro Pro Met Gly Leu Gly Pro Ala Pro Tyr Ser
945                 950                 955                 960

Trp Leu Ala Asp Ser Trp Pro His Pro Ser Arg Ser Pro Ser Ala Gln
                965                 970                 975

Glu Pro Arg Gly Ser Cys Cys Pro Ser Asn Pro Asp Pro Asp Asp Arg
            980                 985                 990

Tyr Tyr Asn Glu Ala Gly Ile Ser Leu Tyr Leu Ala Gln Thr Ala Arg
        995                 1000                1005

Gly Thr Ala Ala Pro Gly Glu Gly Pro Val Tyr Ser Thr Ile Asp
    1010                1015                1020

Pro Ala Gly Glu Glu Leu Gln Thr Phe His Gly Gly Phe Pro Gln
    1025                1030                1035

His Pro Ser Gly Asp Leu Gly Pro Trp Ser Gln Tyr Ala Pro Pro
    1040                1045                1050

Glu Trp Ser Gln Gly Asp Ser Gly Ala Lys Gly Lys Val Lys
    1055                1060                1065

Leu Leu Gly Lys Pro Val Gln Met Pro Ser Leu Asn Trp Pro Glu
    1070                1075                1080

```
Ala Leu Pro Pro Pro Pro Pro Ser Cys Glu Leu Ser Cys Leu Glu
    1085                1090                1095

Gly Pro Glu Glu Glu Leu Glu Gly Ser Ser Glu Pro Glu Glu Trp
    1100                1105                1110

Cys Pro Pro Met Pro Glu Arg Ser His Leu Thr Glu Pro Ser Ser
    1115                1120                1125

Ser Gly Gly Cys Leu Val Thr Pro Ser Arg Arg Glu Thr Pro Ser
    1130                1135                1140

Pro Thr Pro Ser Tyr Gly Gln Gln Ser Thr Ala Thr Leu Thr Pro
    1145                1150                1155

Ser Pro Pro Asp Pro Pro Gln Pro Pro Thr Asp Met Pro His Leu
    1160                1165                1170

His Gln Met Pro Arg Arg Val Pro Leu Gly Pro Ser Ser Pro Leu
    1175                1180                1185

Ser Val Ser Gln Pro Met Leu Gly Ile Arg Glu Ala Arg Pro Ala
    1190                1195                1200

Gly Leu Gly Ala Gly Pro Ala Ala Ser Pro His Leu Ser Pro Ser
    1205                1210                1215

Pro Ala Pro Ser Thr Ala Ser Ser Ala Pro Gly Arg Thr Trp Gln
    1220                1225                1230

Gly Asn Gly Glu Met Thr Pro Pro Leu Gln Gly Pro Arg Ala Arg
    1235                1240                1245

Phe Arg Lys Lys Pro Lys Ala Leu Pro Tyr Arg Arg Glu Asn Ser
    1250                1255                1260

Pro Gly Asp Leu Pro Pro Pro Leu Pro Pro Glu Glu Glu
    1265                1270                1275

Ala Ser Trp Ala Leu Glu Leu Arg Ala Ala Gly Ser Met Ser Ser
    1280                1285                1290

Leu Glu Arg Glu Arg Ser Gly Glu Arg Lys Ala Val Gln Ala Val
    1295                1300                1305

Pro Leu Ala Ala Gln Arg Val Leu His Pro Asp Glu Glu Ala Trp
    1310                1315                1320

Leu Pro Tyr Ser Arg Pro Ser Phe Leu Ser Arg Gly Gln Gly Thr
    1325                1330                1335

Ser Thr Cys Ser Thr Ala Gly Ser Asn Ser Ser Arg Gly Ser Ser
    1340                1345                1350

Ser Ser Arg Gly Ser Arg Gly Pro Gly Arg Ser Arg Ser Arg Ser
    1355                1360                1365

Gln Ser Arg Ser Gln Ser Gln Arg Pro Gly Gln Lys Arg Arg Glu
    1370                1375                1380

Glu Pro Arg
    1385

<210> SEQ ID NO 7
<211> LENGTH: 1007
<212> TYPE: PRT
<213> ORGANISM: Homo sapiens

<400> SEQUENCE: 7

Met Gly Ser Gly Gly Asp Ser Leu Leu Gly Arg Gly Ser Leu Pro
1               5                   10                  15

Leu Leu Leu Leu Leu Ile Met Gly Gly Met Ala Gln Asp Ser Pro
                20                  25                  30

Gln Ile Leu Val His Pro Gln Asp Gln Leu Phe Gln Gly Pro Gly Pro
                35                  40                  45
```

```
Ala Arg Met Ser Cys Gln Ala Ser Gly Gln Pro Pro Thr Ile Arg
    50                  55                  60

Trp Leu Leu Asn Gly Gln Pro Leu Ser Met Val Pro Pro Asp Pro His
65                  70                  75                  80

His Leu Leu Pro Asp Gly Thr Leu Leu Leu Gln Pro Pro Ala Arg
                85                  90                  95

Gly His Ala His Asp Gly Gln Ala Leu Ser Thr Asp Leu Gly Val Tyr
                100                 105                 110

Thr Cys Glu Ala Ser Asn Arg Leu Gly Thr Ala Val Ser Arg Gly Ala
            115                 120                 125

Arg Leu Ser Val Ala Val Leu Arg Glu Asp Phe Gln Ile Gln Pro Arg
    130                 135                 140

Asp Met Val Ala Val Gly Glu Gln Phe Thr Leu Glu Cys Gly Pro
145                 150                 155                 160

Pro Trp Gly His Pro Glu Pro Thr Val Ser Trp Trp Lys Asp Gly Lys
                165                 170                 175

Pro Leu Ala Leu Gln Pro Gly Arg His Thr Val Ser Gly Gly Ser Leu
                180                 185                 190

Leu Met Ala Arg Ala Glu Lys Ser Asp Glu Gly Thr Tyr Met Cys Val
    195                 200                 205

Ala Thr Asn Ser Ala Gly His Arg Glu Ser Arg Ala Ala Arg Val Ser
    210                 215                 220

Ile Gln Glu Pro Gln Asp Tyr Thr Glu Pro Val Glu Leu Leu Ala Val
225                 230                 235                 240

Arg Ile Gln Leu Glu Asn Val Thr Leu Leu Asn Pro Asp Pro Ala Glu
                245                 250                 255

Gly Pro Lys Pro Arg Pro Ala Val Trp Leu Ser Trp Lys Val Ser Gly
                260                 265                 270

Pro Ala Ala Pro Ala Gln Ser Tyr Thr Ala Leu Phe Arg Thr Gln Thr
                275                 280                 285

Ala Pro Gly Gly Gln Gly Ala Pro Trp Ala Glu Glu Leu Leu Ala Gly
    290                 295                 300

Trp Gln Ser Ala Glu Leu Gly Gly Leu His Trp Gly Gln Asp Tyr Glu
305                 310                 315                 320

Phe Lys Val Arg Pro Ser Ser Gly Arg Ala Arg Gly Pro Asp Ser Asn
                325                 330                 335

Val Leu Leu Leu Arg Leu Pro Glu Lys Val Pro Ser Ala Pro Pro Gln
                340                 345                 350

Glu Val Thr Leu Lys Pro Gly Asn Gly Thr Val Phe Val Ser Trp Val
    355                 360                 365

Pro Pro Pro Ala Glu Asn His Asn Gly Ile Ile Arg Gly Tyr Gln Val
    370                 375                 380

Trp Ser Leu Gly Asn Thr Ser Leu Pro Pro Ala Asn Trp Thr Val Val
385                 390                 395                 400

Gly Glu Gln Thr Gln Leu Glu Ile Ala Thr His Met Pro Gly Ser Tyr
                405                 410                 415

Cys Val Gln Val Ala Ala Val Thr Gly Ala Gly Ala Gly Glu Pro Ser
                420                 425                 430

Arg Pro Val Cys Leu Leu Glu Gln Ala Met Glu Arg Ala Thr Gln
    435                 440                 445

Glu Pro Ser Glu His Gly Pro Trp Thr Leu Glu Gln Leu Arg Ala Thr
    450                 455                 460
```

```
Leu Lys Arg Pro Glu Val Ile Ala Thr Cys Gly Val Ala Leu Trp Leu
465                 470                 475                 480

Leu Leu Leu Gly Thr Ala Val Cys Ile His Arg Arg Arg Arg Ala Arg
            485                 490                 495

Val His Leu Gly Pro Gly Leu Tyr Arg Tyr Thr Ser Glu Asp Ala Ile
            500                 505                 510

Leu Lys His Arg Met Asp His Ser Asp Ser Gln Trp Leu Ala Asp Thr
            515                 520                 525

Trp Arg Ser Thr Ser Gly Ser Arg Asp Leu Ser Ser Ser Ser Ser Leu
            530                 535                 540

Ser Ser Arg Leu Gly Ala Asp Ala Arg Asp Pro Leu Asp Cys Arg Arg
545                 550                 555                 560

Ser Leu Leu Ser Trp Asp Ser Arg Ser Pro Gly Val Pro Leu Leu Pro
            565                 570                 575

Asp Thr Ser Thr Phe Tyr Gly Ser Leu Ile Ala Glu Leu Pro Ser Ser
            580                 585                 590

Thr Pro Ala Arg Pro Ser Pro Gln Val Pro Ala Val Arg Arg Leu Pro
            595                 600                 605

Pro Gln Leu Ala Gln Leu Ser Ser Pro Cys Ser Ser Ser Asp Ser Leu
            610                 615                 620

Cys Ser Arg Arg Gly Leu Ser Ser Pro Arg Leu Ser Leu Ala Pro Ala
625                 630                 635                 640

Glu Ala Trp Lys Ala Lys Lys Lys Gln Glu Leu Gln His Ala Asn Ser
            645                 650                 655

Ser Pro Leu Leu Arg Gly Ser His Ser Leu Glu Leu Arg Ala Cys Glu
            660                 665                 670

Leu Gly Asn Arg Gly Ser Lys Asn Leu Ser Gln Ser Pro Gly Ala Val
            675                 680                 685

Pro Gln Ala Leu Val Ala Trp Arg Ala Leu Gly Pro Lys Leu Leu Ser
            690                 695                 700

Ser Ser Asn Glu Leu Val Thr Arg His Leu Pro Pro Ala Pro Leu Phe
705                 710                 715                 720

Pro His Glu Thr Pro Thr Gln Ser Gln Gln Thr Gln Pro Pro Val
            725                 730                 735

Ala Pro Gln Ala Pro Ser Ser Ile Leu Leu Pro Ala Ala Pro Ile Pro
            740                 745                 750

Ile Leu Ser Pro Cys Ser Pro Ser Pro Gln Ala Ser Ser Leu Ser
            755                 760                 765

Gly Pro Ser Pro Ala Ser Ser Arg Leu Ser Ser Ser Ser Leu Ser Ser
            770                 775                 780

Leu Gly Glu Asp Gln Asp Ser Val Leu Thr Pro Glu Glu Val Ala Leu
785                 790                 795                 800

Cys Leu Glu Leu Ser Glu Gly Glu Glu Thr Pro Arg Asn Ser Val Ser
            805                 810                 815

Pro Met Pro Arg Ala Pro Ser Pro Thr Thr Tyr Gly Tyr Ile Ser
            820                 825                 830

Val Pro Thr Ala Ser Glu Phe Thr Asp Met Gly Arg Thr Gly Gly Gly
            835                 840                 845

Val Gly Pro Lys Gly Gly Val Leu Leu Cys Pro Pro Arg Pro Cys Leu
            850                 855                 860

Thr Pro Thr Pro Ser Glu Gly Ser Leu Ala Asn Gly Trp Gly Ser Ala
865                 870                 875                 880

Ser Glu Asp Asn Ala Ala Ser Ala Arg Ala Ser Leu Val Ser Ser Ser
```

-continued

```
                885                 890                 895
Asp Gly Ser Phe Leu Ala Asp Ala His Phe Ala Arg Ala Leu Ala Val
            900                 905                 910
Ala Val Asp Ser Phe Gly Phe Gly Leu Glu Pro Arg Glu Ala Asp Cys
            915                 920                 925
Val Phe Ile Asp Ala Ser Ser Pro Ser Pro Arg Asp Glu Ile Phe
            930                 935                 940
Leu Thr Pro Asn Leu Ser Leu Pro Leu Trp Glu Trp Arg Pro Asp Trp
945                 950                 955                 960
Leu Glu Asp Met Glu Val Ser His Thr Gln Arg Leu Gly Arg Gly Met
            965                 970                 975
Pro Pro Trp Pro Pro Asp Ser Gln Ile Ser Ser Gln Arg Ser Gln Leu
            980                 985                 990
His Cys Arg Met Pro Lys Ala Gly Ala Ser Pro Val Asp Tyr Ser
            995                1000                1005
```

<210> SEQ ID NO 8
<211> LENGTH: 1114
<212> TYPE: PRT
<213> ORGANISM: Homo sapiens

<400> SEQUENCE: 8

```
Met Ser Gln Thr Gln Asp Tyr Glu Cys Arg Ser His Asn Val Asp Leu
1               5                  10                  15
Pro Glu Ser Arg Ile Pro Gly Ser Asn Thr Arg Leu Glu Trp Val Glu
            20                  25                  30
Ile Ile Glu Pro Arg Thr Arg Glu Arg Met Tyr Ala Asn Leu Val Thr
        35                  40                  45
Gly Glu Cys Val Trp Asp Pro Pro Ala Gly Val Arg Ile Lys Arg Thr
    50                  55                  60
Ser Glu Asn Gln Trp Trp Glu Leu Phe Asp Pro Asn Thr Ser Arg Phe
65                  70                  75                  80
Tyr Tyr Tyr Asn Ala Ser Thr Gln Arg Thr Val Trp His Arg Pro Gln
                85                  90                  95
Gly Cys Asp Ile Ile Pro Leu Ala Lys Leu Gln Thr Leu Lys Gln Asn
            100                 105                 110
Thr Glu Ser Pro Arg Ala Ser Ala Glu Ser Ser Pro Gly Arg Gly Ser
            115                 120                 125
Ser Val Ser Arg Glu Gly Ser Thr Ser Ser Leu Glu Pro Glu Pro
        130                 135                 140
Asp Thr Glu Lys Ala Gln Glu Leu Pro Ala Arg Ala Gly Arg Pro Ala
145                 150                 155                 160
Ala Phe Gly Thr Val Lys Glu Asp Ser Gly Ser Ser Pro Gly
                165                 170                 175
Val Phe Leu Glu Lys Asp Tyr Glu Ile Tyr Arg Asp Tyr Ser Ala Asp
            180                 185                 190
Gly Gln Leu Leu His Tyr Arg Thr Ser Ser Leu Arg Trp Asn Ser Gly
        195                 200                 205
Ala Lys Glu Arg Met Leu Ile Lys Val Ala Asp Arg Glu Pro Ser Phe
    210                 215                 220
Leu Ala Ala Gln Gly Asn Gly Tyr Ala Pro Asp Gly Pro Pro Gly Val
225                 230                 235                 240
Arg Ser Arg Arg Pro Ser Gly Ser Gln His Ser Pro Ser Leu Gln Thr
                245                 250                 255
```

```
Phe Ala Pro Glu Ala Asp Gly Thr Ile Phe Pro Glu Arg Arg Pro
            260                 265                 270

Ser Pro Phe Leu Lys Arg Ala Glu Leu Pro Gly Ser Ser Pro Leu
        275                 280                 285

Leu Ala Gln Pro Arg Lys Pro Ser Gly Asp Ser Gln Pro Ser Pro
    290                 295                 300

Arg Tyr Gly Tyr Glu Pro Pro Leu Tyr Glu Glu Pro Val Glu Tyr
305                 310                 315                 320

Gln Ala Pro Ile Tyr Asp Glu Pro Pro Met Asp Val Gln Phe Glu Ala
                325                 330                 335

Gly Gly Gly Tyr Gln Ala Gly Ser Pro Gln Arg Ser Pro Gly Arg Lys
            340                 345                 350

Pro Arg Pro Phe Leu Gln Pro Asn Lys Gln Gly Pro Pro Ser Pro Cys
            355                 360                 365

Gln Gln Leu Val Leu Thr Lys Gln Lys Cys Pro Glu Arg Phe Leu Ser
    370                 375                 380

Leu Glu Tyr Ser Pro Ala Gly Lys Glu Tyr Val Arg Gln Leu Val Tyr
385                 390                 395                 400

Val Glu Gln Ala Gly Ser Ser Pro Lys Leu Arg Ala Gly Pro Arg His
                405                 410                 415

Lys Tyr Ala Pro Asn Pro Gly Gly Ser Tyr Ser Leu Gln Pro Ser
            420                 425                 430

Pro Cys Leu Leu Arg Asp Gln Arg Leu Gly Val Lys Ser Gly Asp Tyr
            435                 440                 445

Ser Thr Met Glu Gly Pro Glu Leu Arg His Ser Gln Pro Pro Thr Pro
450                 455                 460

Leu Pro Gln Ala Gln Glu Asp Ala Met Ser Trp Ser Ser Gln Asp
465                 470                 475                 480

Thr Leu Ser Ser Thr Gly Tyr Ser Pro Gly Thr Arg Lys Arg Lys Ser
                485                 490                 495

Arg Lys Pro Ser Leu Cys Gln Ala Thr Ser Ala Thr Pro Thr Glu Gly
            500                 505                 510

Pro Gly Asp Leu Leu Val Glu Gln Pro Leu Ala Glu Glu Gln Pro Pro
    515                 520                 525

Cys Gly Thr Ser Leu Ala Pro Val Lys Arg Ala Glu Gly Glu Ala
    530                 535                 540

Gly Ala Arg Gly Ala Ala Glu Pro Phe Leu Ala Gln Ala Arg Leu Ala
545                 550                 555                 560

Trp Glu Ala Gln Gln Ala His Phe His Met Lys Gln Arg Ser Trp
            565                 570                 575

Asp Ser Gln Gln Asp Gly Ser Gly Tyr Glu Ser Asp Gly Ala Leu Pro
            580                 585                 590

Leu Pro Met Pro Gly Pro Val Val Arg Ala Phe Ser Glu Asp Glu Ala
        595                 600                 605

Leu Ala Gln Gln Glu Asn Arg His Trp Arg Arg Gly Thr Phe Glu Lys
    610                 615                 620

Leu Gly Phe Pro Gln Ile Leu Leu Glu Lys Ser Val Ser Val Gln Thr
625                 630                 635                 640

Asn Leu Ala Ser Pro Glu Pro Tyr Leu His Pro Ser Gln Ser Glu Asp
                645                 650                 655

Leu Ala Ala Cys Ala Gln Phe Glu Ser Ser Arg Gln Ser Arg Ser Gly
            660                 665                 670

Val Pro Ser Ser Ser Cys Val Phe Pro Thr Phe Thr Leu Arg Lys Pro
```

675                 680                 685
Ser Ser Glu Thr Asp Ile Glu Asn Trp Ala Ser Lys His Phe Asn Lys
    690                 695                 700

His Thr Gln Gly Leu Phe Arg Arg Lys Val Ser Ile Ala Asn Met Leu
705                 710                 715                 720

Ala Trp Ser Ser Glu Ser Ile Lys Lys Pro Met Ile Val Thr Ser Asp
                725                 730                 735

Arg His Val Lys Lys Glu Ala Cys Glu Leu Phe Lys Leu Ile Gln Met
                740                 745                 750

Tyr Met Gly Asp Arg Arg Ala Lys Ala Asp Pro Leu His Val Ala Leu
                755                 760                 765

Glu Val Ala Thr Lys Gly Trp Ser Val Gln Gly Leu Arg Asp Glu Leu
        770                 775                 780

Tyr Ile Gln Leu Cys Arg Gln Thr Thr Glu Asn Phe Arg Leu Glu Ser
785                 790                 795                 800

Leu Ala Arg Gly Trp Glu Leu Met Ala Ile Cys Leu Ala Phe Phe Pro
                805                 810                 815

Pro Thr Pro Lys Phe His Ser Tyr Leu Glu Gly Tyr Ile Tyr Arg His
                820                 825                 830

Met Asp Pro Val Asn Asp Thr Lys Val Thr Gln His Ile Lys Glu Leu
                835                 840                 845

Leu Glu Arg Asn Thr Lys Lys Lys Ser Lys Leu Arg Lys Lys Pro Lys
    850                 855                 860

Pro Tyr Val Glu Glu Pro Asp Gly Val Ala Ile Ser Thr Tyr Ala Lys
865                 870                 875                 880

Tyr Cys Tyr His Lys Leu Gln Lys Ala Ala Leu Thr Gly Ala Lys Lys
                885                 890                 895

Gly Leu Lys Lys Pro Asn Val Glu Glu Ile Arg His Ala Lys Asn Ala
                900                 905                 910

Val Phe Ser Pro Ser Met Phe Gly Ser Ala Leu Gln Glu Val Met Gly
        915                 920                 925

Met Gln Arg Glu Arg Tyr Pro Glu Arg Gln Leu Pro Trp Val Gln Thr
    930                 935                 940

Arg Leu Ser Glu Glu Val Leu Ala Leu Asn Gly Asp Gln Thr Glu Gly
945                 950                 955                 960

Ile Phe Arg Val Pro Gly Asp Ile Asp Glu Val Asn Ala Leu Lys Leu
                965                 970                 975

Gln Val Asp Gln Trp Lys Val Pro Thr Gly Leu Glu Asp Pro His Val
                980                 985                 990

Pro Ala Ser Leu Leu Lys Leu Trp Tyr Arg Glu Leu Glu Glu Pro Leu
        995                 1000                1005

Ile Pro His Glu Phe Tyr Gln Cys Ile Ala His Tyr Asp Ser
    1010                1015                1020

Pro Glu Ala Ala Val Ala Val Val His Ala Leu Pro Arg Ile Asn
    1025                1030                1035

Arg Met Val Leu Cys Tyr Leu Ile Arg Phe Leu Gln Val Phe Val
    1040                1045                1050

Gln Pro Ala Asn Val Ala Val Thr Lys Met Asp Val Ser Asn Leu
    1055                1060                1065

Ala Met Val Met Ala Pro Asn Cys Leu Arg Cys Gln Ser Asp Asp
    1070                1075                1080

Pro Arg Val Ile Phe Glu Asn Thr Arg Lys Glu Met Ser Phe Leu
    1085                1090                1095

Arg Val Leu Ile Gln His Leu Asp Thr Ser Phe Met Glu Gly Val
    1100                1105                1110

Leu

<210> SEQ ID NO 9
<211> LENGTH: 7931
<212> TYPE: DNA
<213> ORGANISM: Homo sapiens

<400> SEQUENCE: 9

| | | | | | |
|---|---|---|---|---|---|
| gggagaggga | gacgcaggcg | gcgaaacggc | agaggagccg | agcccctcc | gcccaaggcg | 60 |
| ccctccctcc | gtccgcgcac | aggcgccgtc | gcttggagga | gcaaggtgcc | tcccagcccg | 120 |
| caggggcgcc | gcgcgcaagc | ccgcgggctc | ttcggtggct | ctgccccggg | actgcacctg | 180 |
| gaggcggccc | cggacgggga | tggtcagcgg | ctgctgccgt | ctggctcgcg | agcgggacgc | 240 |
| tgtgagggca | ccatggcgct | gactcccggg | tggggtcct | cggcggggcc | ggtccggccg | 300 |
| gagctctggc | tgctgctgtg | ggcagccgcg | tggcgcctgg | gtgcctcggc | gtgccccgcc | 360 |
| ctctgcacct | gcaccggaac | cacggtggac | tgccacggca | cggggctgca | ggccattccc | 420 |
| aagaatatac | ctcggaacac | cgagcgcctg | gaactcaatg | gcaacaacat | cactcggatc | 480 |
| cataagaatg | actttgcggg | gctcaagcag | ctgcgggtgc | tgcagctgat | ggagaaccag | 540 |
| attggagcag | tggaacgtgg | tgcttttgat | gacatgaagg | agctggagcg | gctgcgactg | 600 |
| aaccgaaacc | agctgcacat | gttaccggaa | ctgctgttcc | agaacaacca | ggctttgtca | 660 |
| agactggact | tgagtgagaa | cgccatccag | gccatcccca | ggaaagcttt | tcggggagct | 720 |
| acggaccta | aaaatttaca | gctggacaag | aaccagatca | gctgcattga | ggaaggggcc | 780 |
| ttccgtgctc | tgcgggggct | ggaggtgctg | accctgaaca | acaacaatat | caccaccatc | 840 |
| cccgtgtcca | gcttcaacca | tatgcccaag | ctacggacct | tccgcctgca | ctccaaccac | 900 |
| ctgttttgcg | actgccacct | ggcctggctc | tcgcagtggc | tgaggcagcg | gccaaccatc | 960 |
| gggctcttca | cccagtgctc | gggcccagcc | agcctgcgtg | gcctcaatgt | ggcagaggtc | 1020 |
| cagaagagtg | agttcagctg | ctcaggccag | ggagaagcgg | ggcgcgtgcc | cacctgcacc | 1080 |
| ctgtcctccg | gctcctgccc | ggccatgtgc | acctgcagca | atggcatcgt | ggactgtcgt | 1140 |
| ggaaaaggcc | tcactgccat | cccggccaac | ctgcccgaga | ccatgacgga | gatacgcctg | 1200 |
| gagctgaacg | gcatcaagtc | catccctcct | ggagccttct | caccctacag | aaagctacgg | 1260 |
| aggatagacc | tgagcaacaa | tcagatcgct | gagattgcac | ccgacgcctt | ccagggcctc | 1320 |
| cgctccctga | actcgctggt | cctctatgga | aacaagatca | cagacctccc | ccgtggtgtg | 1380 |
| tttgaggcc | tatacaccct | acagctcctg | ctcctgaatg | ccaacaagat | caactgcatc | 1440 |
| cggcccgatg | ccttccagga | cctgcagaac | ctctcactgc | tctccctgta | tgacaacaag | 1500 |
| atccagagcc | tcgccaaggg | cactttcacc | tccctgcggg | ccatccagac | tctgcacctg | 1560 |
| gcgcagaacc | ctttcatttg | cgactgtaac | ctcaagtggc | tggcagactt | cctgcgcacc | 1620 |
| aatcccatcg | agacgagtgg | tgcccgctgt | gccagtcccc | ggcgcctcgc | caacaagcgc | 1680 |
| atcgggcaga | tcaagagcaa | gaagttccgg | tgctcagcca | agagcagta | cttcattcca | 1740 |
| ggcacggagg | attaccagct | gaacagcgag | tgcaacagcg | acgtggtctg | tccccacaag | 1800 |
| tgccgctgtg | aggccaacgt | ggtggagtgc | tccagcctga | agctcaccaa | gatccctgag | 1860 |
| cgcatccccc | agtccacggc | agaactgcga | ttgaataaca | atgagatttc | catcctggag | 1920 |
| gccactggga | tgtttaaaaa | acttacacat | ctgaagaaaa | tcaatctgag | caacaacaag | 1980 |

```
gtgtcagaaa ttgaagatgg ggccttcgag ggcgcagcct ctgtgagcga gctgcaccta    2040
actgccaacc agctggagtc catccggagc ggcatgttcc ggggtctgga tggcttgagg    2100
accctaatgc tgcggaacaa ccgcatcagc tgcatccaca acgacagctt cacgggcctg    2160
cgcaacgtcc ggctcctctc gctctacgac aaccagatca ccaccgtatc cccaggagcc    2220
ttcgacaccc tccagtccct ctccacactg aatctcctgg ccaacccttt caactgcaac    2280
tgccagctgg cctggctagg aggctggcta cggaagcgca agatcgtgac ggggaacccg    2340
cgatgccaga accctgactt tttgcggcag attcccctgc aggacgtggc cttccctgac    2400
ttcaggtgtg aggaaggcca ggaggagggg ggctgcctgc cccgcccaca gtgcccacag    2460
gagtgcgcct gcctggacac cgtggtccga tgcagcaaca agcacctgcg ggccctgccc    2520
aagggcattc ccaagaatgt cacagaactc tatttggacg ggaaccagtt cacgctggtt    2580
ccgggacagc tgtctacctt caagtacctg cagctcgtgg acctgagcaa caacaagatc    2640
agttccttaa gcaattcctc cttcaccaac atgagccagc tgaccactct gatcctcagc    2700
tacaatgccc tgcagtgcat cccgccttg gccttccagg actccgctc cctgcgcctg    2760
ctgtctctcc acggcaatga catctccacc ctccaagagg gcatctttgc agacgtgacc    2820
tccctgtctc acctggccat ggtgccaac ccctatact gtgactgcca cctccgctgg    2880
ctgtccagct gggtgaagac tggctacaag gaacccggca ttgctcgttg tgctgggccc    2940
caggacatgg agggcaagct gctcctcacc acgcctgcca agagtttga atgccaaggt    3000
cctccaacgc tggctgtcca ggccaagtgt gatctctgct tgtccagtcc gtgccagaac    3060
cagggcacct gccacaacga ccccttgag gtgtacaggt gcgcctgccc cagcggctat    3120
aagggtcgag actgtgaggt gtccctggac agctgttcca gtggcccctg tgaaaatggg    3180
ggcacctgcc atgcacagga gggcgaggat gccccgttca cgtgctcctg tcccaccggc    3240
tttgaaggac caacctgtgg ggtgaacaca gatgactgtg tggatcatgc ctgtgccaat    3300
gggggcgtct gtgtggatgg tgtgggcaac tacacctgcc agtgcccct gcagtatgag    3360
ggaaaggcct gtgagcagct ggtggacttg tgctctccgg atctgaaccc atgtcaacac    3420
gaggcccagt gtgtgggcac cccggatggg cccaggtgtg agtgcatgcc aggttatgca    3480
ggtgacaact gcagtgagaa ccaggatgac tgcagggacc accgctgcca gaatggggcc    3540
cagtgtatgg atgaagtcaa cagctactcc tgcctctgtg ctgagggcta cagtggacag    3600
ctctgtgaga tccctcccca tctgcctgcc cccaagagcc cctgtgaggg gactgagtgc    3660
cagaatgggg ccaactgtgt ggaccagggc aacaggcctg tgtgccagtg cctcccaggc    3720
ttcggtggcc ctgagtgtga aagttgctc agtgtcaact tgtggatcg ggacacttac    3780
ctgcagttca ctgacctgca aaactggcca cgggccaaca tcacgttgca ggtctccacg    3840
gcagaggaca tgggatcct tctgtacaac ggggacaacg accacattgc agttgagctg    3900
taccagggcc atgtgcgtgt cagctacgac ccaggcagct accccagctc tgccatctac    3960
agtgctgaga cgatcaacga tggcaattc cacaccgttg agctggttgc ctttgaccag    4020
atggtgaatc tctccattga tggcgggagc cccatgacca tggacaactt tggcaaacat    4080
tacacgctca acagcgaggc ccactctat gtggagggga tgcccgtgga tgtcaactca    4140
gctgccttcc gcctgtggca gatcctcaac ggcaccggct tccacggttg catccgaaac    4200
ctgtacatca caacgagct gcaggacttc accaagacgc agatgaagcc aggcgtggtg    4260
ccaggctgcg aaccctgccg caagctctac tgcctgcatg gcatctgcca gcccaatgcc    4320
```

```
accccagggc ccatgtgcca ctgcgaggct ggctgggtgg gcctgcactg tgaccagccc    4380
gctgacggcc cctgccatgg ccacaagtgt gtccatgggc aatgcgtgcc cctcgacgct    4440
ctttcctaca gctgccagtg ccaggatggg tactcggggg cactgtgcaa ccaggccggg    4500
gccctggcag agccctgcag aggcctgcag tgcctgcatg ccactgccag gcctcaggc     4560
accaagggg cacactgtgt gtgtgacccc ggcttttcgg gcgagctgtg tgagcaagag     4620
tccgagtgcc gggggaccc tgtccgggac tttcaccagg tccagagggg ctatgccatc     4680
tgccagacca cgcgccccct gtcatgggtg gagtgccggg gctcgtgccc aggccagggc    4740
tgctgccagg gccttcggct gaagcggagg aagttcacct ttgagtgcag cgatgggacc    4800
tcttttgccg aggaggtgga aaagcccacc aagtgtggct gtgccctctg cgcatagcgc    4860
tgggcgtgga caggccggtg agggcgggca aggggcccca gccgctgcag cagcggagac    4920
agtcgccagc agctgggctg gggtgcaggt catcacagga cggctcctgg gcagctgggc    4980
cctcctgggt ggggtggtgc cagagcagcc ttttaaaagc aaattgcgcc atagctgggg    5040
gcagcggggg tgggcgaggc ctgagctgcg ggctgccctc tccggaagtg ccttgcacaa    5100
ataggcgctt aataaatatt tgttgagtga atgtgtgcgt gaggtcaggc caagaagtgc    5160
agaacgatga caccctcct tacctgctat ctgaatctgg agaagaaaaa tgacagcctt     5220
ccaaaccaac ccttccctt ggcctgtggc ccaggctggc ttggaactgg gtctgtggcc     5280
ccagaagcct cttacccctc tgcgggcaac catgaagtac tgtcagcctc cccgggaagc    5340
cagcctggtt cattctgctg ctacagaatc tgctggtggt aggccaggct ctggagcggg    5400
ggtgccgcct cctgctggcc agggagggtc ggacccttgc ccctgggct gactggcagc     5460
tctgcagcca cggcttggga acgaggctgt gggtggaggt ggttcttagg accaggcctc    5520
tgaatcctaa agttctagca tgactactgt agctgcgagg gcttatgtgg aggaaacagt    5580
cacaggggct gctcagggtg gcagaccca ctaaagaggg cagagggttc tttgctctag     5640
ataaacaaac atcatctgcc tccagacact ggccacagta ggagtattgg tcctgggctt    5700
ccccagccac cagtcagcca caagctgtcg gtgacctatt ggtagaggga ctgggtgtga    5760
gggtctgggc cagggtgctt gacctgggag cagctggttc agagtccttc acaccgcagg    5820
ccagtaggga gcagtggaag ggacagtgct ccaggcattg ggaagtccct gctggctcta    5880
tcactcgggg caaacttctc cccacctggg ccttgggttc ttcagctata aatggccag     5940
aggtgggggg cgggatgact aaaggaacag tgcagactcc cccactgtgg tcttgggagg    6000
ccagaggagt tagaagacct atctatctat ctatctatct acattgatca catcaaaagt    6060
atttatgtgc ctaacccggg gctggggatt gtggacgttc tggcctaatg gacagatgtg    6120
aactcatccc agagcatcgc aggaatgacc aggatgcccg ggaagagttg agctgagtgg    6180
gggctccagc cacagacagc ggcccaggcc agggagttgc tggcaacgaa ggagccagtg    6240
gtggaagaag aagaggccct gaatatacga ttgcctgccc acgttgtctt ctcttccata    6300
cacagtgaaa atgtagaaag atggtttgtg aggccaaact gtgaatgggc taaagggagg    6360
caaagttgca ctctccttcc ccagagggct caccaagagg gcacaccccc gggggttctg    6420
gtgggcaacg ggggtgagca tgtccctgcc ctggctccct ccatctgtga ccaggaggca    6480
tggctgggtg tatgttcagg tgaggctcag agtggcattg tgtccctgtc ccctgcccag    6540
ggcagtgagg ggagccttg atgctgatta aaggctaga actggggtag aggtgcctgg     6600
catgtctcat gccatgggga ctcaatctag caactgtgag tcctggggtc cctgtgatgg    6660
gaagagggca gtgccctgcc caatgtggca ggtgtcctca tggcaggatc tgcccctcac    6720
```

```
caggggctg ggatctactt gcttggagct ctgagcaagg ccacaatgcc cgcccccacc    6780
cccaagtaga ctgcagcctg ggcctcatgg ggcttctccc aggcccacat ggcatccctc    6840
tctgagtttc caggccaccg tgggaccctg cagagcatct gcaccgggct ggatagggca    6900
gaaaagctca agggcagcta gcttgcctct tccctggaag aaaggtgctc tgggactcac    6960
caaccctgag aaagatagct ttcctggcca ccaccattcc ccaccaccct ggagaagcca    7020
attcccaggc ttgaagggca ctggctggca ggaggcctct tcattctgca ggaggtggaa    7080
aggacacctg tagacaggtg atgctcaccc ctcacctggc gccatggggc tgggaggtga    7140
gcggctggca tgtttgttcc tagggagcac catgtgagct taaggctccc ctgaccggcc    7200
ccaccacatg gcccagcctc ctagcacagc agcgctgacc tcagtgcagt ctgaggattg    7260
gaatccacca tgagatgatg tgagagctgt gtgccccagg atcaactttt tctccaactt    7320
ggccatcagc cagcgagttg ctaaggacct gagtcagcac tcacgttgcc tattcacact    7380
ccgcttgaaa gtccggaagg tggctactgc aaaatcaccc ctctgagaag tcctctctcc    7440
acatcttgtc ccccttgtg aagaccccta gttcgctctg cattttaggc atgaagagat    7500
acagcagggt gcgtccggag ggagctgtgg ccttgcaaca ccactggcaa cagggccggg    7560
gctcccggtg aaggtgtcag gaagtggaaa aggctggact ttgtctcctc tttgcctgct    7620
ggtagcctaa ccgcaaaagt atctctttat acagaatact tacagattct aatatatatt    7680
tgtatttcat tttgttacag tattttata tgttaaagtc aacatccagc gtcttgtttt    7740
gcctttcaga tgctatgtgg tcgtggcacg ttttgttggg ggtttctgta gtcgtcttgt    7800
ttggatcaac tcctagaggc tggtttagaa caggcccatg agggagctgc acctgccctg    7860
gaagtattgt tttagactat gtcgatattg tctgttgtct tccatgtgaa catgacattg    7920
agtcactctg c                                                         7931
```

<210> SEQ ID NO 10
<211> LENGTH: 4670
<212> TYPE: DNA
<213> ORGANISM: Homo sapiens

<400> SEQUENCE: 10

```
cagacactgc gcggttccct cggagcagca agctaaagaa agcccccagt gccggcgagg      60
aaggaggcgg cggggaaaga tgcgcggcgt tggctggcag atgctgtccc tgtcgctggg     120
gttagtgctg gcgatcctga acaaggtggc accgcaggcg tgcccggcgc agtgctcttg     180
ctcgggcagc acagtggact gtcacggct ggcgctgcgc agcgtgccca ggaatatccc     240
ccgcaacacc gagagactgg atttaaatgg aaataacatc acaagaatta cgaagacaga     300
ttttgctggt cttagacatc taagagttct tcagcttatg gagaataaga ttagcaccat     360
tgaaagagga gcattccagg atcttaaaga actagagaga ctgcgtttaa acagaaatca     420
ccttcagctg tttcctgagt tgctgttct tgggactgcg aagctataca ggcttgatct     480
cagtgaaaac caaattcagg caatcccaag gaaagctttc cgtggggcag ttgacataaa     540
aaatttgcaa ctggattaca accagatcag ctgtattgaa gatggggcat tcagggctct     600
ccgggacctg aagtgctca ctctcaacaa taacaacatt actagacttt ctgtggcaag     660
tttcaaccat atgcctaaac ttaggacttt tcgactgcat tcaaacaacc tgtattgtga     720
ctgccacctg gcctggctct ccgactggct tcgccaaagg cctcggggttg gtctgtacac     780 tcagtgtatg ggccctccc acctgagagg ccataatgta gccgaggttc aaaaacgaga     840
```

```
atttgtctgc agtggtcacc agtcatttat ggctccttct tgtagtgttt tgcactgccc      900
tgccgcctgt acctgtagca acaatatcgt agactgtcgt gggaaaggtc tcactgagat      960
ccccacaaat cttccagaga ccatcacaga aatacgtttg aacagaaca caatcaaagt      1020 catccctcct ggagctttct caccatataa aaagcttaga cgaattgacc tgagcaataa      1080
tcagatctct gaacttgcac cagatgcttt ccaaggacta cgctctctga attcacttgt      1140
cctctatgga aataaaatca cagaactccc caaaagttta tttgaaggac tgttttcctt      1200
acagctccta ttattgaatg ccaacaagat aaactgcctt cgggtagatg cttttcagga      1260
tctccacaac ttgaaccttc tctccctata tgacaacaag cttcagacca tcgccaaggg      1320 gacctttttca cctcttcggg ccattcaaac tatgcatttg gcccagaacc cctttatttg      1380
tgactgccat ctcaagtggc tagcggatta tctccatacc aacccgattg agaccagtgg      1440
tgcccgttgc accagccccc gccgcctggc aaacaaaaga attggacaga tcaaaagcaa      1500
gaaattccgt tgttcaggta cagaagatta tcgatcaaaa ttaagtggag actgctttgc      1560
ggatctggct tgccctgaaa agtgtcgctg tgaaggaacc acagtagatt gctctaatca      1620
aaagctcaac aaaatcccgg agcacattcc ccagtacact gcagagttgc gtctcaataa      1680
taatgaattt accgtgttgg aagccacagg aatctttaag aaacttcctc aattacgtaa      1740
aataaacttt agcaacaata agatcacaga tattgaggag ggagcatttg aaggagcatc      1800
tggtgtaaat gaaatacttc ttacgagtaa tcgtttggaa aatgtgcagc ataagatgtt      1860
caagggattg gaaagcctca aaactttgat gttgagaagc aatcgaataa cctgtgtggg      1920
gaatgacagt ttcataggac tcagttctgt gcgtttgctt tctttgtatg ataatcaaat      1980
tactacagtt gcaccagggg catttgatac tctccattct ttatctactc taaacctctt      2040
ggccaatcct tttaactgta actgctacct ggcttggttg ggagagtggc tgagaaagaa      2100
gagaattgtc acgggaaatc ctagatgtca aaaaccatac ttcctgaaag aaataccat       2160 ccaggatgtg gccattcagg acttcacttg tgatgacgga aatgatgaca atagttgctc      2220
cccactttct cgctgtccta ctgaatgtac ttgcttggat acagtcgtcc gatgtagcaa      2280
caagggtttg aaggtcttgc cgaaaggtat tccaagagat gtcacagagt tgtatctgga      2340
tggaaaccaa tttacactgg ttcccaagga actctccaac tacaaacatt taacacttat      2400
agacttaagt aacaacagaa taagcacgct ttctaatcag agcttcagca acatgaccca      2460
gctcctcacc ttaattctta gttacaaccg tctgagatgt attcctcctc gcacctttga      2520
tggattaaag tctcttcgat tactttctct acatggaaat gacatttctg ttgtgcctga      2580
aggtgctttc aatgatcttt ctgcattatc acatctagca attggagcca accctcttta      2640
ctgtgattgt aacatgcagt ggttatccga ctgggtgaag tcggaatata aggagcctgg      2700
aattgctcgt tgtgctggtc ctggagaaat ggcagataaa cttttactca caactccctc      2760
caaaaatttt acctgtcaag gtcctgtgga tgtcaatatt ctagctaagt gtaaccctg       2820 cctatcaaat ccgtgtaaaa atgatggcac atgtaatagt gatccagttg acttttaccg      2880
atgcacctgt ccatatggtt tcaaggggca ggactgtgat gtcccaattc atgcctgcat      2940
cagtaaccca tgtaaacatg gaggaacttg ccacttaaag gaaggagaag aagatggatt      3000
ctggtgtatt tgtgctgatg gatttgaagg agaaaattgt gaagtcaacg ttgatgattg      3060
tgaagataat gactgtgaaa ataattctac atgtgtcgat ggcattaata actacacatg      3120
cctttgccca cctgagtata caggtgagtt gtgtgaggag aagctggact tctgtgccca      3180
ggacctgaac ccctgccagc acgattcaaa gtgcatccta actccaaagg gattcaaatg      3240
```

```
tgactgcaca ccagggtacg taggtgaaca ctgcgacatc gattttgacg actgccaaga    3300
caacaagtgt aaaaacggag cccactgcac agatgcagtg aacggctata cgtgcatatg    3360
ccccgaaggt tacagtggct tgttctgtga gttttctcca cccatggtcc tccctcgtac    3420
cagcccctgt gataattttg attgtcagaa tggagctcag tgtatcgtca gaataaatga    3480
gccaatatgt cagtgtttgc ctggctatca gggagaaaag tgtgaaaaat tggttagtgt    3540 gaatttata aacaaagagt cttatcttca gattccttca gccaaggttc ggcctcagac    3600
gaacataaca cttcagattg ccacagatga agacagcgga atcctcctgt ataagggtga    3660
caaagaccat atcgcggtag aactctatcg ggggcgtgtt cgtgccagct atgacaccgg    3720
ctctcatcca gcttctgcca tttacagtgt ggagacaatc aatgatggaa acttccacat    3780
tgtggaacta cttgccttgg atcagagtct ctctttgtcc gtggatggtg gaaccccaa    3840 aatcatcact aacttgtcaa agcagtccac tctgaatttt gactctccac tctatgtagg    3900
aggcatgcca gggaagagta acgtggcatc tctgcgccag gcccctgggc agaacggaac    3960
cagcttccac ggctgcatcc ggaaccttta catcaacagt gagctgcagg acttccagaa    4020
ggtgccgatg caaacaggca ttttgcctgg ctgtgagcca tgccacaaga aggtgtgtgc    4080
ccatggcaca tgccagccca gcagccaggc aggcttcacc tgcgagtgcc aggaaggatg    4140 gatgggccc ctctgtgacc aacgaccaa tgacccttgc cttggaaata aatgcgtaca    4200
tggcacctgc ttgcccatca atgcgttctc ctacagctgt aagtgcttgg agggccatgg    4260
aggtgtcctc tgtgatgaag aggaggatct gtttaaccca tgccaggcga tcaagtgcaa    4320
gcatgggaag tgcaggcttt caggtctggg gcagccctac tgtgaatgca gcagtggata    4380 cacggggac agctgtgatc gagaaatctc ttgtcgaggg gaaaggataa gagattatta    4440
ccaaaagcag cagggctatg ctgcttgcca aacaaccaag aaggtgtccc gattagagtg    4500
cagaggtggg tgtgcaggag ggcagtgctg tggaccgctg aggagcaagc ggcggaaata    4560 ctcttcgaa tgcactgacg gctcctcctt tgtggacgag gttgagaaag tggtgaagtg    4620
cggctgtacg aggtgtgtgt cctaaacaca ctcccggcag ctctgtcttt            4670
```

<210> SEQ ID NO 11
<211> LENGTH: 4818
<212> TYPE: DNA
<213> ORGANISM: Homo sapiens

<400> SEQUENCE: 11

```
cgcgctcccc gcgcgcctcc tcgggctcca cgcgtcttgc cccgcagagg cagcctcctc      60
caggagcggg gccctgcaca ccatggcccc cgggtgggca ggggtcggcg ccgccgtgcg     120
cgcccgcctg gcgctggcct tggcgctggc gagcgtcctg agtgggcctc cagccgtcgc     180
ctgccccacc aagtgtacct gctccgctgc cagcgtggac tgccacgggc tgggcctccg     240
cgcggttcct cggggcatcc cccgcaacgc tgagcgcctt gacctggaca gaataatat      300 caccaggatc accaagatgg acttcgctgg gctcaagaac ctccgagtct tgcatctgga     360
agacaaccag gtcagcgtca tcgagagagg cgccttccag gacctgaagc agctagagcg     420
actgcgcctg aacaagaata gctgcaagt ccttccagaa ttgcttttcc agagcacgcc     480
gaagctcacc agactagatt tgagtgaaaa ccagatccag gggatcccga ggaaggcgtt     540
ccgcggcatc accgatgtga agaacctgca actggacaac aaccacatca gctgcattga     600
agatggagcc ttccgagcgc tgcgcgattt ggagatcctt acctcaaca acaacaacat      660
```

```
cagtcgcatc ctggtcacca gcttcaacca catgccgaag atccgaactc tgcgcctcca    720
ctccaaccac ctctactgcg actgccacct ggcctggctc tcggattggc tgcgacagcg    780
acggacagtt ggccagttca cactctgcat ggctcctgtg catttgaggg gcttcaacgt    840
ggcggatgtg cagaagaagg agtacgtgtg cccagccccc cactcggagc cccatcctg     900
caatgccaac tccatctcct gcccttcgcc ctgcacgtgc agcaataaca tcgtggactg    960
tcgaggaaag ggcttgatgg agattcctgc caacttgccg gagggcatcg tcgaaatacg    1020
cctagaacag aactccatca agccatccc tgcaggagcc ttcacccagt acaagaaact     1080
gaagcgaata gacatcagca agaatcagat atcggatatt gctccagatg ccttccaggg   1140
cctgaaatca ctcacatcgc tggtcctgta tgggaacaag atcaccgaga ttgccaaggg   1200
actgtttgat gggctggtgt ccctacagct gctcctcctc aatgccaaca agatcaactg   1260
cctgcgggtg aacacgtttc aggacctgca gaacctcaac ttgctctccc tgtatgacaa   1320
caagctgcag accatcagca aggggctctt cgcccctctg cagtccatcc agacactcca   1380
cttagcccaa aacccatttg tgtgcgactg ccacttgaag tggctggccg actacctcca   1440
ggacaaccc atcgagacaa gcggggcccg ctgcagcagc ccgcgccgac tcgccaacaa    1500
gcgcatcagc cagatcaaga gcaagaagtt ccgctgctca ggctccgagg attaccgcag   1560
caggttcagc agcgagtgct tcatggacct cgtgtgcccc gagaagtgtc gctgtgaggg   1620
cacgattgtg gactgctcca accagaagct ggtccgcatc ccaagccacc tccctgaata   1680
tgtcaccgac ctgcgactga atgacaatga ggtatctgtt ctggaggcca ctggcatctt   1740
caagaagttg cccaacctgc ggaaaataaa tctgagtaac aataagatca aggaggtgcg   1800
agagggagct ttcgatggag cagccagcgt gcaggagctg atgctgacag gaaccagct    1860
ggagaccgtg cacgggcgcg tgttccgtgg cctcagtggc ctcaaaacct tgatgctgag   1920
gagtaacttg atcagctgtg tgagtaatga cacctttgcc ggcctgagtt cggtgagact   1980
gctgtccctc tatgacaatc ggatcaccac catcaccct ggggccttca ccacgcttgt    2040
ctccctgtcc accataaacc tcctgtccaa cccttcaac tgcaactgcc acctggcctg    2100
gctcggcaag tggttgagga agaggcggat cgtcagtggg aaccctaggt gccagaagcc   2160
attttttcctc aaggagattc ccatccagga tgtggccatc caggacttca cctgtgatgg   2220
caacgaggag agtagctgcc agctgagccc gcgctgcccg gagcagtgca cctgtatgga   2280
gacagtggtg cgatgcagca caaggggct ccgcgccctc cccagaggca tgcccaagga    2340
tgtgaccgag ctgtacctgg aaggaaacca cctaacagcc gtgcccagag agctgtccgc   2400
cctccgacac ctgacgctta ttgacctgag caacaacagc atcagcatgc tgaccaatta   2460
caccttcagt aacatgtctc acctctccac tctgatcctg agctacaacc ggctgaggtg   2520
catccccgtc cacgccttca cgggctgcg gtccctgcga gtgctaaccc tccatggcaa    2580
tgacattttcc agcgttcctg aaggctcctt caacgacctc acatctcttt cccatctggc   2640
gctgggaacc aacccactcc actgtgactg cagtcttcgg tggctgtcgg agtgggtgaa   2700
ggcggggtac aaggagcctg gcatcgcccg ctgcagtagc cctgagccca tggctgacag    2760
gctcctgctc accaccccaa cccaccgctt ccagtgcaaa gggccagtgg acatcaacat   2820
tgtggccaaa tgcaatgcct gcctctccag cccgtgcaag aataacggga catgcaccca   2880
ggaccctgtg gagctgtacc gctgtgcctg ccctacagc tacaagggca aggactgcac    2940
tgtgcccatc aacacctgca tccagaaccc ctgtcagcat ggaggcacct gccacctgag   3000
tgacagccac aaggatgggt tcagctgctc ctgccctctg ggctttgagg ggcagcggtg   3060
```

-continued

```
tgagatcaac ccagatgact gtgaggacaa cgactgcgaa acaatgcca cctgcgtgga    3120 cgggatcaac aactacgtgt gtatctgtcc gcctaactac acaggtgagc tatgcgacga    3180
ggtgattgac cactgtgtgc ctgagctgaa cctctgtcag catgaggcca agtgcatccc    3240
cctggacaaa ggattcagct gcgagtgtgt ccctggctac agcgggaagc tctgtgagac    3300
agacaatgat gactgtgtgg cccacaagtg ccgccacggg gcccagtgcg tggacacaat    3360
caatggctac acatgcacct gcccccaggg cttcagtgga cccttctgtg aacccccc     3420 acccatggtc ctactgcaga ccagcccatg cgaccagtac gagtgccaga cggggccca    3480 gtgcatcgtg gtgcagcagg agcccacctg ccgctgccca ccaggcttcg ccggcccag    3540 atgcgagaag ctcatcactg tcaacttcgt gggcaaagac tcctacgtgg aactggcctc    3600
cgccaaggtc cgaccccagg ccaacatctc cctgcaggtg ccactgacaa ggacaacgg    3660 catccttctc tacaaaggag acaatgaccc cctggcactg gagctgtacc agggccacgt    3720
gcggctggtc tatgacagcc tgagttcccc tccaaccaca gtgtacagtg tggagacagt    3780
gaatgatggg cagtttcaca gtgtggagct ggtgacgcta aaccagaccc tgaacctagt    3840
agtggacaaa ggaactccaa agagcctggg gaagctccag aagcagccag cagtgggcat    3900
caacagcccc ctctaccttg gaggcatccc cacctccacc ggcctctccg ccttgcgcca    3960
gggcacggac cggcctctag gcggcttcca cggatgcatc catgaggtgc gcatcaacaa    4020
cgagctgcag gacttcaagg ccctcccacc acagtccctg ggggtgtcac caggctgcaa    4080
gtcctgcacc gtgtgcaagc acggcctgtg ccgctccgtg gagaaggaca gcgtggtgtg    4140
cgagtgccgc ccaggctgga ccggcccact ctgcgaccag gaggcccggg acccctgcct    4200
cggccacaga tgccaccatg gaaaatgtgt ggcaactggg acctcataca tgtgcaagtg    4260
tgccgagggc tatggagggg acttgtgtga caacaagaat gactctgcca atgcctgctc    4320
agccttcaag tgtcaccatg gcagtgcca catctcagac caaggggagc cctactgcct    4380
gtgccagccc ggctttagcg gcgagcactg ccaacaagag aatccgtgcc tgggacaagt    4440
agtccgagag gtgatccgcc gccagaaagg ttatgcatca tgtgccacag cctccaaggt    4500
gcccatcatg gaatgtcgtg ggggctgtgg gccccagtgc tgccagccca cccgcagcaa    4560
gcggcggaaa tacgtcttcc agtgcacgga cggctcctcg tttgtagaag aggtggagag    4620
acacttagag tgcggctgcc tcgcgtgttc ctaagcccct gcccgcctgc ctgccacctc    4680
tcggactcca gcttgatgga gttgggacag ccatgtggga cccctggtg attcagcatg    4740 aaggaaatga agctggagag gaaggtaaag aagaagagaa tattaagtat attgtaaaat    4800
aaacaaaaaa tagaactt                                                 4818
```

<210> SEQ ID NO 12
<211> LENGTH: 5341
<212> TYPE: DNA
<213> ORGANISM: Homo sapiens

<400> SEQUENCE: 12

```
tctgcctcgg ctctttgttg ttcgctttgg atggttcttg aaagtgtctg agcctcctcg     60
gaaatcctgg ggccggagaa gacaaacctt ggaattcttc ctctgcaaaa gtctctgaga    120
tactgacaag cgtccggaaa ggtcgacgag taattgccct gaaaactctt ggctaattga    180
cccacgttgc ttatattaag cctttgtgtg tggtgtgtgg cttcatacat ttggggaccc    240
tatttccact ccctcctctt ggcatgagac tgtatacagg atccacccga ggacaatgat    300
```

```
tgcggagccc gctcacttttt acctgtttgg attaatatgt ctctgttcag gctcccgtct    360
tcgtcaggaa gattttccac ctcgcattgt tgaacaccct tcagacctga ttgtctcaaa    420
aggagaacct gcaactttga actgcaaagc tgaaggccgc cccacaccca ctattgaatg    480
gtacaaaggg ggagagagag tggagacaga caaagatgac cctcgctcac accgaatgtt    540
gctgccgagt ggatctttat ttttcttacg tatagtacat ggacggaaaa gtagacctga    600
tgaaggagtc tatgtctgtg tagcaaggaa ttaccttgga gaggctgtga ccacaatgc    660
atcgctggaa gtagccatac ttcgggatga cttcagacaa aacccttcgg atgtcatggt    720
tgcagtagga gagcctgcag taatggaatg ccaacctcca cgaggccatc ctgagcccac    780
catttcatgg aagaaagatg gctctccact ggatgataaa gatgaaagaa taactatacg    840
aggaggaaag ctcatgatca cttcacccg taaaagtgac gctggcaaat atgtttgtgt    900
tggtaccaat atggttgggg aacgtgagag tgaagtagcc gagctgactg tcttagagag    960
accatcattt gtgaagagac ccagtaactt ggcagtaact gtggatgaca gtgcagaatt   1020
taaatgtgag gcccgaggtg accctgtacc tacagtacga tggaggaaag atgatggaga   1080
gctgcccaaa tccagatatg aaatccgaga tgatcatacc ttgaaaatta ggaaggtgac   1140
agctggtgac atgggttcat acacttgtgt tgcagaaaat atggtgggca aagctgaagc   1200
atctgctact ctgactgttc aagttgggtc tgaacctcca catttttgttg tgaaccccg   1260
tgaccaggtt gttgctttgg gacggactgt aacttttcag tgtgaagcaa ccggaaatcc   1320
tcaaccagct attttctgga ggagagaagg gagtcagaat ctacttttct catatcaacc   1380
accacagtca tccagccgat tttcagtctc ccagactggc gacctcacaa ttactaatgt   1440
ccagcgatct gatgttggtt attacatctg ccagacttta atgttgctg gaagcatcat   1500
cacaaaggca tatttggaag ttacagatgt gattgcagat cggcctcccc cagttattcg   1560
acaaggtcct gtgaatcaga ctgtagccgt ggatggcact ttcgtcctca gctgtgtggc   1620
cacaggcagt ccagtgccca ccattctgtg gagaaaggat ggagtcctcg tttcaaccca   1680
agactctcga atcaaacagt tggagaatgg agtactgcag atccgatatg ctaagctggg   1740
tgatactggt cggtacacct gcattgcatc aaccccccagt ggtgaagcaa catggagtgc   1800
ttacattgaa gttcaagaat ttggagttcc agttcagcct ccaagaccta ctgacccaaa   1860
tttaatccct agtgccccat caaaacctga agtgacagat gtcagcagaa atacagtcac   1920
attatcatgg caaccaaatt tgaattcagg agcaactcca acatcttata ttatagaagc   1980
cttcagccat gcatctggta gcagctggca gaccgtagca gagaatgtga aaacagaaac   2040
atctgccatt aaaggactca aacctaatgc aatttaccct tccttgtgta gggcagctaa   2100
tgcatatgga attagtgatc caagcccaaat atcagatcca gtgaaaacac aagatgtcct   2160
accaacaagt caggggggtgg accacaagca ggtccagaga gagctgggaa atgctgttct   2220
gcacctccac aaccccaccg tccttttcttc ctcttccatc gaagtgcact ggacagtaga   2280
tcaacagtct cagtatatac aaggatataa aattctctat cggccatctg gagccaacca   2340
cggagaatca gactggttag tttttgaagt gaggacgcca gccaaaaaca gtgtggtaat   2400
ccctgatctc agaaagggag tcaactatga aattaaggct cgccctttt ttaatgaatt   2460
tcaaggagca gatagtgaaa tcaagtttgc caaaaccctg aagaagcac ccagtgcccc    2520
accccaaggt gtaactgtat ccaagaatga tggaaacgga actgcaattc tagttagttg   2580
gcagccacct ccagaagaca ctcaaaatgg aatggtccaa gagtataagg tttggtgtct    2640
gggcaatgaa actcgatacc acatcaacaa aacagtggat ggttccacct tttccgtggt   2700
```

```
cattcccttt cttgttcctg gaatccgata cagtgtggaa gtggcagcca gcactgggc    2760 tgggtctggg gtaaagagtg agcctcagtt catccagctg gatgcccatg gaaaccctgt   2820
gtcacctgag gaccaagtca gcctcgctca gcagatttca gatgtggtga agcagccggc   2880
cttcatagca ggtattggag cagcctgttg gatcatcctc atggtcttca gcatctggct   2940
ttatcgacac cgcaagaaga gaaacggact tactagtaca tacgcgggta tcagaaaagt   3000
aacttaccag agaggaggcg aagctgtcag cagtggaggg aggcctggac ttctcaacat   3060
cagtgaacct gccgcgcagc catggctggc agacacgtgg cctaatactg caacaacca    3120 caatgactgc tccatcagct gctgcacggc aggcaatgga acagcgaca gcaacctcac    3180 tacctacagt cgcccagctg attgtatagc aaattataac aaccaactgg ataacaaaca   3240
aacaaatctg atgctccctg agtcaactgt ttatggtgat gtggacctta gtaacaaaat   3300
caatgagatg aaaaccttca atagcccaaa tctgaaggat gggcgttttg tcaatccatc   3360
agggcagcct actccttacg ccaccactca gctcatccag tcaaacctca gcaacaacat   3420
gaacaatggc agcggggact ctggcgagaa gcactggaaa ccactgggac agcagaaaca   3480
agaagtggca ccagttcagt acaacatcgt ggagcaaaac aagctgaaca agattatcg    3540 agcaaatgac acagttcctc caactatccc atacaaccaa tcatacgacc agaacacagg   3600
aggatcctac aacagctcag accggggcag tagtacatct gggagtcagg ggcacaagaa   3660
aggggcaaga acacccaagg taccaaaaca gggtggcatg aactgggcag acctgcttcc   3720
tcctccccca gcacatcctc ctccacacag caatagcgaa gagtacaaca tttctgtaga   3780
tgaaagctat gaccaagaaa tgccatgtcc cgtgccacca gcaaggatgt atttgcaaca   3840
agatgaatta aagaggagg aagatgaacg aggcccccact cccccctgttc ggggagcagc    3900 ttcttctcca gctgccgtgt cctatagcca tcagtccact gccactctga ctccctcccc   3960
acaggaagaa ctccagccca tgttacagga ttgtccagag gagactggcc acatgcagca   4020
ccagcccgac aggagacggc agcctgtgag tcctcctcca ccaccacggc cgatctcccc   4080
tccacatacc tatggctaca tttcaggacc cctggtctca gatatggata cggatgcgcc   4140
agaagaggaa gaagacgaag ccgacatgga ggtagccaag atgcaaacca gaaggctttt   4200
gttacgtggg cttgagcaga cacctgcctc cagtgttggg gacctggaga gctctgtcac   4260
ggggtccatg atcaacggct gggctcagc ctcagaggag gacaacattt ccagcggacg    4320
ctccagtgtt agttcttcgg acggctcctt tttcactgat gctgactttg cccaggcagt   4380
cgcagcagcg gcagagtatg ctggtctgaa agtagcacga cggcaaatgc aggatgctgc   4440
tggccgtcga cattttcatg cgtctcagtg ccctaggccc acaagtcccg tgtctacaga   4500
cagcaacatg agtgccgccg taatgcagaa accagacca gccaagaaac tgaaacacca    4560
gccaggacat ctgcgcagag aaacctacac agatgatctt ccaccacctc ctgtgccgcc   4620
acctgctata aagtcaccta ctgcccaatc aagacacag ctggaagtac gacctgtagt    4680
ggtgccaaaa ctcccttcta tggatgcaag aacagacaga tcatcagaca gaaaaggaag   4740
cagttacaag gggagagaag tgttggatgg aagacaggtt gttgacatgc gaacaaatcc   4800
aggtgatccc agagaagcac aggaacagca aaatgacggg aaaggacgtg gaacaaggc    4860 agcaaaacga gaccttccac cagcaaagac tcatctcatc caagaggata ttctacctta   4920
ttgtagacct acttttccaa catcaaataa tcccagagat cccagttcct caagctcaat   4980
gtcatcaaga ggatcaggaa gcagacaag agaacaagca aatgtaggtc gaagaaatat    5040
```

| | |
|---|---:|
| tgcagaaatg caggtacttg aggatatga agaggagaa gataataatg aagaattaga | 5100 |
| ggaaactgaa agctgaagac aaccaagagg cttatgagat ctaatgtgaa aatcatcact | 5160 |
| caagatgcct cctgtcagat gacacatgac gccagataaa atgttcagtg caatcagagt | 5220 |
| gtacaaattg tcgtttttat tcctcttatt gggatatcat tttaaaaact ttattgggtt | 5280 |
| tttattgttg ttgtttgatc cctaacccta caaagagcct tcctattccc ctcgctgttg | 5340 |
| g | 5341 |

```
<210> SEQ ID NO 13
<211> LENGTH: 5598
<212> TYPE: DNA
<213> ORGANISM: Homo sapiens

<400> SEQUENCE: 13
```

| | |
|---|---:|
| gtcaaaatga gtctgctgat gtttacacaa ctactgctct gtggattttt atatgttcgg | 60 |
| gttgatggat cgcgtcttcg ccaggaggac tttcccccgc ggattgtgga gcatccttcc | 120 |
| gatgtcatcg tctctaaggg cgagcccacg actctgaact gcaaggcgga gggccggcca | 180 |
| acgcccacca ttgagtggta caaagatggg gagcgagtgg agactgacaa ggacgatccc | 240 |
| cggtcccaca ggatgcttct gcccagcgga tccttattct tcttgcgcat cgtgcacggg | 300 |
| cgcaggagta aacctgatga aggaagctac gtttgtgttg cgaggaacta tcttggtgaa | 360 |
| gcagtgagtc gaaatgcgtc tctggaagtg gcattgttac gagatgactt ccgacaaaac | 420 |
| cccacagatg ttgtagtggc agctggagag cctgcaatcc tggagtgcca gcctccccgg | 480 |
| ggacacccag aacccaccat ctactggaaa aagacaaag ttcgaattga tgacaaggaa | 540 |
| gaaagaataa gtatccgtgg tggaaaactg atgatctcca ataccaggaa aagtgatgca | 600 |
| gggatgtata cttgtgttgg taccaatatg gtgggagaaa gggacagtga cccagcagag | 660 |
| ctgactgtct ttgaacgacc cacatttctc aggaggccaa ttaaccaggt ggtactggag | 720 |
| gaagaagctg tagaatttcg ttgtcaagtc caaggagatc ctcaaccaac tgtgaggtgg | 780 |
| aaaaaggatg atgcagactt gccaagagga aggtatgaca tcaaagacga ttacacacta | 840 |
| agaattaaaa agaccatgag tacagatgaa ggcacctata tgtgtattgc tgagaatcgg | 900 |
| gttggaaaaa tggaagcctc tgctacactc accgtccgag ctcccccaca gtttgtggtt | 960 |
| cggccaagag atcagattgt tgctcaaggt cgaacagtga catttccctg tgaaactaaa | 1020 |
| ggaaacccac agccagctgt ttttttggcag aaagaaggca gccagaacct acttttccca | 1080 |
| aaccaacccc agcagcccaa cagtagatgc tcagtgtcac caactggaga cctcacaatc | 1140 |
| accaacattc aacgttccga cgcgggttac tacatctgcc aggctttaac tgtggcagga | 1200 |
| agcattttag caaaagctca actggaggtt actgatgttt tgacagatag acctccacct | 1260 |
| ataattctac aaggcccagc caaccaaacg ctggcagtgg atggtacagc gttactgaaa | 1320 |
| tgtaaagcca ctggtgatcc tcttcctgta attagctggt taaggagggg atttactttt | 1380 |
| ccgggtagag atccaagagc aacaattcaa gagcaaggca cactgcagat taagaattta | 1440 |
| cggatttctg atactggcac ttatacttgt gtggctacaa gttcaagtgg agagacttcc | 1500 |
| tggagtgcag tgctggatgt gacagagtct ggagcaacaa tcagtaaaaa ctatgattta | 1560 |
| agtgacctgc cagggccacc atccaaaccg caggtcactg atgttactaa gaacagtgtc | 1620 |
| accttgtcct ggcagccagg tacccctgga acccttccag caagtgcata tatcattgag | 1680 |
| gctttcagcc aatcagtgag caacagctgg cagaccgtgg caaaccatgt aaagaccacc | 1740 |
| ctctatactg taagaggact gcggcccaat acaatctact tattcatggt cagagcgatc | 1800 |

```
aacccccaag gtctcagtga cccaagtccc atgtcagatc ctgtgcgcac acaagatatc   1860
agcccaccag cacaaggagt ggaccacagg caagtgcaga aagagctagg agatgtcctt   1920
gtccgtcttc ataatccagt tgtgctgact cccaccacgg ttcaggtcac atggacggtt   1980
gatcgccaac cccagtttat ccaaggctac cgagtgatgt atcgtcagac ttcaggtctg   2040
caggcgacat cttcgtggca gaatttagat gccaaagtcc cgactgaacg aagtgctgtc   2100
ttagtcaacc tgaaaaaggg ggtgacttat gaaattaaag tacggccata ttttaatgag   2160
ttccaaggaa tggatagtga atctaaaacg gttcgtacta ctgaagaagc cccaagtgcc   2220
ccaccacagt ctgtcactgt actgacagtt ggaagctaca atagcacaag tattagtgtt   2280
tcctgggatc ctcctcctcc agatcaccag aatggaatta ccaagaataa caagatctgg   2340
tgtctaggaa atgaaacgcg attccatatc aacaaaactg tggatgcagc cattcggtcc   2400
gtaataattg gtggattatt cccaggtatt caataccggg tagaggttgc agctagtacc   2460
agtgcagggg ttggagtaaa gagtgagcca cagccaataa taatcgggag acgcaatgaa   2520
gttgtcatta ctgaaaacaa taacagcata actgagcaaa tcactgatgt ggtgaagcaa   2580
ccagccttta tagctggtat tggtggtgcc tgctgggtaa ttctgatggg ttttagcata   2640
tggttgtatt ggcgaagaaa gaagaggaag ggactcagta attatgctgt tacgtttcaa   2700
agaggagatg gaggactaat gagcaatgga agccgtccag gtcttctcaa tgctggtgat   2760
cccagctatc catggcttgc tgattcttgg ccagccacga gcttgccagt aaataatagc   2820
aacagtggcc caaatgagat tggaaatttt ggccgtggag atgtgctgcc accagttcca   2880
ggccaagggg ataaaacagc aacgatgctc tcagatggag ccatttatag tagcattgac   2940
ttcactacca aaaccagtta caacagttcc agccaaataa cacaggctac cccatatgcc   3000
acgacacaga tcttgcattc caacagcata catgaattgg ctgtcgatct gcctgatcca   3060
caatggaaaa gctcaattca gcaaaaaaca gatctgatgg gatttggtta ttctctacct   3120
gatcagaaca aaggtaacaa tggtgggaaa ggtggaaaaa agaagaaaaa taaaaactct   3180
tctaaaccac agaaaaacaa tggatccact tgggccaatg tccctctacc tccccccccca   3240 gtccagcccc ttcctggcac ggagctggaa cactatgcag tggaacaaca agaaaatggc   3300
tatgacagtg atagctggtg cccaccattg ccagtacaaa cttacttaca ccaaggtctg   3360
gaagatgaac tggaagaaga tgatgatagg gtcccaacac ctcctgttcg aggcgtggct   3420
tcttctcctg ctatctcctt tggacagcag tccactgcaa ctcttactcc atccccacgg   3480 gaaagagatgc aacccatgct gcaggctcac ctggatgagt tgacaagagc ctatcagttt   3540
gatatagcaa acaaacatg gcacattcaa agcaataatc aacctccaca gcctccagtt   3600
ccaccgttag ttatgtgtc tggagccttg atttctgatt tggaaacgga tgttgcagat   3660
gatgatgccg acgacgaaga ggaagcttta gaaatcccca ggcccctgag agcactggac   3720
cagactcctg gatccagcat ggacaatcta gacagctctg tgcaggaaa agcctttacc   3780 tcctctcaaa gacctcgacc taccagccca ttttctactg acagtaacac cagtgcagcc   3840
ctgagtcaaa gtcagaggcc tcggcccact aaaaaacaca agggagggcg gatggaccaa   3900
caaccagcat tgcctcatcg aagggaagga atgacagatg aggaggcctt ggtgccctat   3960
agcaagccca gtttcccatc tccaggtggc cacagctcat caggaacagc ttcttctaag   4020
ggatccactg gacctaggaa aaccgaggtg ttgagagcag gccaccagcg caatgccagc   4080
gaccttcttg acataggata tatgggctcc aacagtcaag gacagtttac aggtgaatta   4140
```

```
tagtaaatga gaggagacat acaaagctgc tctgaaggac catcaggtcc ggactcatgg    4200
aagtgatgac tctaaacagt gcaatgaaca atttatttat gtactattaa aagaactgta    4260
aatgcaatgt aaagacacac agccacacat atcccacaga tattttcatt gtgttcttct    4320
cttaagtaca ccacccacct taactctttc ttgtcaggag tatataaaaa agaaagaaaa    4380
caaaactcgc cctacaggaa gaaaaggatt ctcctctgta tataatttct tttgtgcatt    4440
gctatgcaag ctcactcttt ttagctctgc tcatattatt gtctgttctt attggtctgt    4500
tgtactatat gtgaattaat aggctgtggt gccatatatt aacttttaat tgtgtaactt    4560
ttatgtttaa attttgcact gcaattttat ttggtgataa gcacaaatct ctactcctca    4620
tgacatgaag aaaaagactg aatgtgaagg gagtttctgt actgtaagct agattggata    4680
atgatggctg taacaaatca tgttagatgg ttttcagttg gggtgtagaa ataggaagat    4740
gcaaaggaac aatggtgttg gcaaagtctt ctttgaatat cagggactga gtcaataaaa    4800
aaaatagtag aaaggtggct tttactattg acaaaagccg gggtcaaaaa aagtagttta    4860
agtcttaaga ctgaatatgc attaaagtat gcaggtagca aagatgtaat aaatttgctt    4920
aaaaaaagaa attaaagttt tatttagaat caattttacc tgtcattgta attgacccat    4980
ctgagaatta caataagcaa gaggaaatta aggtgttttg caagagctgt atttatatta    5040
cagttttta aaaacatttt ctgaattatc gtaattaagc tctccaactc gttaagtcag    5100
aatataatat gaagttcccc aaggaaacga acaaatgaa ctctagaata tctagcaaat    5160
agttaaagaa gcaatttatt attagggcat actcgggctg tttccaaata taaactctat    5220
tgcaatatct tatttcatct ttctaataca tgtacagtgc acactagagg atagagctgc    5280
atcacttaaa ttcatgactt aaaaaataat acagtttata tacaacttgt ttttatttg    5340
attaagaagt gaagttatg ccacccaatg tatagccaaa ttgtacgtgc ttaaaaaaca    5400
gtgccgagag tatgttcagt tcgcagtaag tagatttatt ggaataaata ttctatggta    5460
cattctcaga aattggcttc caactaaaat acgtttgacc cattttgaat aaggaaattg    5520
aaaagaaaaa tttaaaagga gaaaaaatg catgttttata aacttttaa ataaaaccag    5580
accttgtaag tggacatt                                                  5598

<210> SEQ ID NO 14
<211> LENGTH: 4554
<212> TYPE: DNA
<213> ORGANISM: Homo sapiens

<400> SEQUENCE: 14
gagggcacga agaggcaccg accgtaccca ggcgcaccgg caggagagcg gcaccgtggc     60
tgccgcagcg cgcagaggct gtggaggggc ttacggctcc cagcccacgg gtctcagacc    120
caggggctgg gccccagcc cccagtcccg atcccagctg ggtcgagcca tgctgcgcta    180
cctgctgaaa acgctgctgc agatgaactt gttcgcggac tctctggccg gggacatctc    240
caactccagc gagctgctct tgggcttcaa ctcctcgctg gcggcgctca accacaccct    300
gctgcctccc ggcgatccct ctctcaacgg gtcaagggta ggaccggagg acgctatgcc    360
ccgcatcgtg gagcagccgc cagatctgct ggtctcccga ggcgagcccg ccacgttgcc    420
ctgccgcgct gaaggccgac cccgacccaa cattgagtgg tacaagaacg ggcgcgtgt    480
ggccactgtg cgggaggatc cgcgtgcgca ccgcctgctg ctgccagcg cgcccctctt    540
cttcccgcgc atcgtgcacg ggcgccgcgc gcggccggac gaaggtgtct acacttgcgt    600
ggctcgcaac tacctggggg cagcagcgag cagaaacgcc tcgctggaag tggcagtcct    660
```

```
ccgtgatgat ttccggcagt ctcctggaaa cgtggtggtg gcagtggggg agccagcagt    720
actggaatgc gtgccccccc gcggccaccc ggagccttcc gtgtcctgga ggaaggacgg    780
tgcaagactc aaggaagagg aaggaaggat cacgatccgt ggagggaagc tgatgatgtc    840
acatacactc aagagcgatg caggcatgta tgtgtgcgta gcctccaaca tggcgggaga    900
acgggagagt gcggcagctg aagtcatggt actggagcgt ccctcattcc tgcgcagacc    960
agtgaatcag gtggtcctgg ctgatgcccc tgtgactttc ctatgtgagg tgaagggga    1020 tcccccacct cgtctacgct ggcgcaagga ggatgggaa ctgcccacag gcaggtatga    1080
gatccggagt gaccacagcc tttggattgg gcatgtgagt gccgaagatg agggaacgta    1140
cacctgtgtg gcggagaaca gtgtgggccg cgctgaagca tctggctccc tcagtgttca    1200
cgtcccaccc cagttggtga cccagccca ggaccagatg gcagctcctg gagagagcgt    1260
ggctttccag tgcgagacca aggaaaccc cccacctgcc atcttctggc agaaggaggg    1320
gagtcaggtc ctgcttttcc ccagtcagtc acttcagccg acggggcgct tctcagtgtc    1380
tccaagaggc caacttaaca tcaccgcggt gcagcgtggg gatgctgggt actacgtgtg    1440
ccaggctgtc agtgtggctg gcagcatcct ggccaaggcc ctgctggaga taaaaggagc    1500
ctctttggat gggctgcctc ctgtcatcct ccagggacca gccaatcaga cgctggtgct    1560
tggctcctcc gtgtggctgc cctgcagagt gactgggaac cctcaaccca gtgtccgatg    1620
gaagaaggat gggcagtggc tgcaggggga tgacctccag ttcaagacaa tggccaacgg    1680
taccctgtac atcgccaatg tgcaggagat ggacatgggc ttctacagct gcgtggccaa    1740
gagttccaca ggggaagcca catggagcgg ctggcttaag atgcgggaag actggggagt    1800
atcaccagac ccccctacag aacccagttc ccctccgggg gctccctctc agccagtggt    1860
cactgagatc accaagaaca gcattaccct gacctggaag cccaacccac aaactggggc    1920
tgcagtcacg tcttatgtga tagaggcctt cagcccagca gctggcaaca catggcgtac    1980
tgtggcagat ggcgtgcagc tggagacaca cacagtcagc ggtctgcagc ccaataccat    2040
ctacctgttt ctggttcgag cagtgggagc ctggggcctc agtgagccca gccccgtctc    2100
tgagcctgtc cgtacacagg atagcagccc ctctaggcca gtggaggacc catggagagg    2160
ccagcaggga ctgcggaag tggctgtgcg cctgcaggag cccatagtcc tgggaccccg    2220
gaccctgcag gtgtcctgga ctgtggatgg cccagtccag ctggtgcaag gtttccgggt    2280
gtcttggagg gtagcaggcc ctgagggagg aagctggaca atgttggacc tacagtcccc    2340
aagccagcaa agtactgtgc taagaggact ccctccaggg acccaaatcc agatcaaggt    2400
gcaagcccaa ggccaggagg ggctgggggc tgaaagcctc tctgtgacca ggagcattcc    2460
tgaggaggcc cccagtggcc ccccacaggg agtggcggtg ccttgggg gtgatggcaa    2520 cagcagtatc actgtgtcct gggaacctcc actcccctcc cagcaaaatg ggtcatcac    2580 ggaataccag atctggtgcc tgggcaatga gagccgcttt cacctcaatc gatctgcagc    2640
aggctgggca cgctccgcaa tgctccgagg actggtgccc ggtctcctct atcgaaccct    2700
ggtcgcggcg gccaccagcg caggcgtggg cgtgcccagt gccccagtgc tggtgcagct    2760
gccgtccccg ccggacctgg agcccgggct ggaggtgggc gcgggctgg cggtgcggct    2820 ggcgagggtg ctgcgggagc ccgccttcct cgcgggcagc ggcgcagcct gcggggcgct    2880
gcttctcggg ctctgcgccg ccctctactg gcgccggaaa cagcgcaaag agctcagcca    2940
ctacacggcc tcttttgcct acacaccggc agtgtccttc ccgcactcag agggcctctc    3000
```

```
tggagccagt tccaggccac ccatgggcct tggccccgcc ccctactcat ggctggcaga    3060
ttcgtggccc cacccatctc gaagcccctc ggcccaggaa cccaggggaa gctgctgccc    3120
tagcaatcct gacccggacg acagatatta caacgaagcg ggaatctccc tgtatctagc    3180
tcagacggcc aggggcacgg ccgcccctgg cgagggtcct gtctatagca ccattgaccc    3240
agcgggggag gagctgcaga ccttccatgg gggcttcccc caacatccct caggagatct    3300
gggtccctgg agccagtacg ctcctccaga gtggagccag ggggacagtg gagccaaggg    3360
aggcaaagtg aagcttctgg ggaaacctgt gcagatgccc tctctgaact ggccagaagc    3420
cctgccccca cctcctcctt cttgtgaact gagctgccta aagggccgg aggaggagct    3480 ggagggcagc tcagagccag aggagtggtg cccgccaatg cctgagagaa gtcacctgac    3540
ggagcccagc tccagtggag ggtgcctggt caccccatcc cgaagggaaa cccctctcc    3600 cacaccttcc tatggacagc agtccacagc cactcttaca ccctcacctc ctgaccctcc    3660
ccagccccca actgacatgc ccatctccca tcagatgccc aggagggtgc cccttgggcc    3720
gagttcccct ctcagtgtat cccagcccat gctgggcatc cgtgaagcga ggcctgctgg    3780 cttggtgct ggccctgcag cctcacccca cctcagcccc agtcctgccc ctagcacagc    3840
cagcagtgcc ccaggcagaa cctggcaggg gaatggggag atgactcccc cacttcaagg    3900
accccgtgct cgattccgga agaaacccaa ggctcttccc tacaggaggg agaacagtcc    3960
tggggacttg cccccaccac ccttgccacc gccagaggaa gaggcgagct gggccctaga    4020
gctgagggca gcaggcagca tgtcctccct ggagcgggag cgcagtgggg agaggaaagc    4080
ggtccaggcc gtgcccctgg cagcccagcg ggtgctccac ccagatgaag aggcctggct    4140
cccatacagc agaccaagct tcctgtcccg gggccagggc accagcacat gttccacggc    4200
cggcagcaac tcttccaggg gctccagcag ctctaggggc tcccggggcc ctggccggag    4260
ccggagtcgg agtcagagcc ggagccagag ccaaaggcca ggacagaaac gccgagagga    4320
accaagatga cccttgttgg ggcattgaga atatcatgag tgccacgggg aaggggagta    4380
gggatgtctt ttccccccca gcagtgatga gtggggctag ctgaagccca ttggtttcca    4440
cgatttcaat tggctgagaa ggcagagagc tagctcctcc ctttctttct ttttccacct    4500
gagacttgtt tataaaaaac aaaacaataa aaagagtctg atcagagccc aggg         4554
```

<210> SEQ ID NO 15
<211> LENGTH: 3836
<212> TYPE: DNA
<213> ORGANISM: Homo sapiens

<400> SEQUENCE: 15

```
aaagccgctt ccctcctggg gcagagtctc ggtcacaaac aaccaccacc ggcccacccc      60
gcccctcctt ccctcttcac tgtgagctca gagcagcagg acaaagtgct cgggacaagg     120
acatagggct gagagtagcc atgggctctg gaggagacag cctcctgggg ggcaggggtt     180
ccctgcctct gctgctcctg ctcatcatgg gaggcatggc tcaggactcc ccgccccaga     240
tcctagtcca cccccaggac cagctgttcc agggccctgg ccctgccagg atgagctgcc     300
aagcctcagg ccagccacct cccaccatcc gctggttgct gaatgggcag ccctgagca     360 tggtgccccc agacccacac cacctcctgc ctgatgggac ccttctgctg ctacagcccc     420
ctgcccgggg acatgccac gatggccagg ccctgtccac agacctgggt gtctacacat     480
gtgaggccag caaccggctt ggcacggcag tcagcagagg cgctcggctg tctgtggctg     540
tcctccggga ggatttccag atccagcctc gggacatggt ggctgtggtg ggtgagcagt     600
```

```
ttactctgga atgtgggccg ccctggggcc acccagagcc cacagtctca tggtggaaag      660
atgggaaacc cctggccctc cagcccggaa ggcacacagt gtccgggggg tccctgctga      720
tggcaagagc agagaagagt gacgaaggga cctacatgtg tgtggccacc aacagcgcag      780
gacatagggg gagccgcgca gcccgggttt ccatccagga gccccaggac tacacggagc      840
ctgtggagct tctggctgtg cgaattcagc tggaaaatgt gacactgctg aacccggatc      900
ctgcagaggg ccccaagcct agaccggcgg tgtggctcag ctggaaggtc agtgccctg       960 ctgcgcctgc ccaatcttac acggccttgt tcaggaccca gactgccccg ggaggccagg     1020
gagctccgtg ggcagaggag ctgctggccg gctggcagag cgcagagctt ggaggcctcc     1080
actggggcca agactacgag ttcaaagtga gaccatcctc tggccgggct cgaggccctg     1140
acagcaacgt gctgctcctg aggctgccgg aaaaagtgcc cagtgcccca cctcaggaag     1200
tgactctaaa gcctggcaat ggcactgtct tgtgagctg gtcccacca cctgctgaaa       1260 accacaatgg catcatccgt ggctaccagg tctggagcct gggcaacaca tcactgccac     1320
cagccaactg gactgtagtt ggtgagcaga cccagctgga aatcgccacc catatgccag     1380
gctcctactg cgtgcaagtg gctgcagtca ctggtgctgg agctggggag cccagtagac     1440
ctgtctgcct cctttagag caggccatgg agcgagccac ccaagaaccc agtgagcatg      1500
gtccctggac cctggagcag ctgagggcta ccttgaagcg gcctgaggtc attgccacct     1560
gcggtgttgc actctggctg ctgcttctgg gcaccgccgt gtgtatccac cgccggcgcc     1620
gagctagggt gcacctgggc ccaggtctgt acagatatac cagtgaggat gccatcctaa     1680
aacacaggat ggatcacagt gactcccagt ggttggcaga cacttggcgt tccacctctg     1740
gctctcggga cctgagcagc agcagcagcc tcagcagtcg gctgggggcg gatgccgggg    1800
acccactaga ctgtcgtcgc tccttgctct cctgggactc ccgaagcccc ggcgtgcccc     1860
tgcttccaga caccagcact ttttatggct ccctcatcgc tgagctgccc tccagtaccc     1920
cagccaggcc aagtccccag gtcccagctg tcaggcgcct cccaccccag ctggcccagc     1980
tctccagccc ctgttccagc tcagacagcc tctgcagccg cagggggactc tcttctcccc     2040 gcttgtctct ggcccctgca gaggcttgga aggccaaaaa gaagcaggag ctgcagcatg     2100
ccaacagttc cccactgctc cggggcagcc actccttgga gctccgggcc tgtgagttag     2160
gaaatagagg ttccaagaac ctttcccaaa gcccaggagc tgtgccccaa gctctggttg     2220
cctggcgggc cctgggaccg aaactcctca gctcctcaaa tgagctggtt actcgtcatc     2280
tccctccagc acccctcttt cctcatgaaa ctccccccaac tcagagtcaa cagacccagc     2340
ctccggtggc accacaggct ccctcctcca tcctgctgcc agcagccccc atccccatcc     2400
ttagcccctg cagtccccct agccccagg cctcttccct ctctggcccc agcccagctt      2460
ccagtcgcct gtccagctcc tcactgtcat cctgggggga ggatcaagac agcgtgctga    2520
cccctgagga ggtagccctg tgcttggaac tcagtgaggg tgaggagact cccaggaaca    2580
gcgtctctcc catgccaagg gctccttcac cccccaccac ctatgggtac atcagcgtcc     2640
caacagcctc agagttcacg gacatgggca ggactggagg aggggtgggg cccaagggg     2700 gagtcttgct gtgcccacct cggccctgcc tcacccccac ccagccagg ggctccttag      2760 ccaatggttg gggctcagcc tctgaggaca atgccgccag cgccagagcc agccttgtca    2820
gctcctccga tggctccttc ctcgctgatg ctcactttgc ccgggccctg gcagtggctg     2880
tggatagctt tggtttcggt ctagagccca gggaggcaga ctgcgtcttc atagatgcct     2940
```

| | |
|---|---:|
| catcacctcc ctccccacgg gatgagatct tcctgacccc caacctctcc ctgcccctgt | 3000 |
| gggagtggag gccagactgg ttggaagaca tggaggtcag ccacacccag cggctgggaa | 3060 |
| gggggatgcc tccctggccc cctgactctc agatctcttc ccagagaagt cagctccact | 3120 |
| gtcgtatgcc caaggctggt gcttctcctg tagattactc ctgaaccgtg tccctgagac | 3180 |
| ttcccagacg ggaatcagaa ccacttctcc tgtccaccca caagacctgg gctgtggtgt | 3240 |
| gtgggtcttg gcctgtgttt ctctgcagct ggggtccacc ttcccaagcc tccagagagt | 3300 |
| tctccctcca cgattgtgaa acaaatgaa aacaaaatta gcaaagct gacctggagc | 3360 |
| cctcagggag caaacatca tctccacctg actcctagcc actgctttct cctctgtgcc | 3420 |
| atccactccc accaccaggt tgttttggcc tgaggagcag ccctgcctgc tgctcttccc | 3480 |
| ccaccatttg gatcacagga agtggaggag ccagaggtgc ctttgtggag acagcagtg | 3540 |
| gctgctggga gagggctgtg gaggaaggag cttctcggag ccccctctca gccttacctg | 3600 |
| ggcccctcct ctagagaaga gctcaactct ctcccaacct caccatggaa agaaaataat | 3660 |
| tatgaatgcc actgaggcac tgaggcccta cctcatgcca aacaagggt tcaaggctgg | 3720 |
| gtctagcgag gatgctgaag gaagggaggt atgagaccgt aggtcaaaag caccatcctc | 3780 |
| gtactgttgt cactatgagc ttaagaaatt tgataccata aatggtaaa gacttg | 3836 |

<210> SEQ ID NO 16
<211> LENGTH: 5147
<212> TYPE: DNA
<213> ORGANISM: Homo sapiens

<400> SEQUENCE: 16

| | |
|---|---:|
| gggaaaaaaa aaaaaaactg tccaccaaga attctatacc taaatatctt ttaagtgaag | 60 |
| gtgacataaa gatgtttcca acacacaac agctgaacta gttcattacc agcagacctt | 120 |
| cactgaaaga aatgttacag atgctttagg ctgaaggaaa acaaaaccat gtggaagtct | 180 |
| ggatctatac agaaaattga agagtactgg aaatggtaac tacatggatt caacacaact | 240 |
| gcaatcaaaa tcccagcagg ctattttgta gaaatcgaga agctgatcct gaaattcata | 300 |
| tagaaatgca aaggacctgg aataattaaa acaacttcaa caatgaaaag cagagtttgg | 360 |
| ggactcgcag tgcctgattg cagacccggt gcatttggac tcactgtggc gtggggtccc | 420 |
| agatgggagg aagcttcctg agaggtgacg cctgagttga gtctaagagg acaaggagtg | 480 |
| cggcaccttc ccgtctgatg ctggcgttgt gcgtatggtg ccctgacgtc tgtccacgtg | 540 |
| ggcgcggaag caaacagcga tgtcccagac gcaggactac gagtgcagga gccataatgt | 600 |
| cgacctgccg gagtcgagga ttccagggtc gaacactcgg ttggagtggg tggagatcat | 660 |
| cgaaccgcgc accgcgagc gcatgtacgc caacctggtc accggtgagt gcgtgtggga | 720 |
| cccgccggcc ggcgtccgca tcaagcgcac cagcgagaac cagtggtggg agctgttcga | 780 |
| ccccaacacg tcccgcttct actactacaa tgccagcacg cagcgcacgg tgtggcaccg | 840 |
| gccgcagggc tgcgacatca tcccgctggc caagctgcag acgctgaagc agaacacgga | 900 |
| gtccccgcgc gcctcggcgg agagcagccc cgggcgcggc agcagcgtca gccgtgaggg | 960 |
| cagcaccagc tcctccctgg agcccgagcc cgacactgag aaagcgcagg agttgccagc | 1020 |
| gagggccggg cggccgcgg cgtttgggac agtgaaggag gacagcggca gctcttcacc | 1080 |
| accaggagtg ttccttgaga aggactatga gatttaccgg gattacagtg cggacggcca | 1140 |
| gcttcttcac tacaggacct cctcgctgcg gtggaactcg ggcgcaaag agcgcatgct | 1200 |
| catcaaggtc gctgatcggg agcccagctt cctcgccgcc cagggcaatg gctacgcccc | 1260 |

| | |
|---|---|
| agacggccca cctggggtcc gctcccgcag accctccggc agccagcact cacccagcct | 1320 |
| gcagaccttc gccccggagg ctgacggcac catcttcttc ccagagagga ggccgtcacc | 1380 |
| cttcctgaag agggccgagc tcccaggcag cagctccccg ctgctggccc agccccgaaa | 1440 |
| gccctccggg gactcgcagc cctcctcccc gcgctatggc tatgaacccc cgctctacga | 1500 |
| ggagccccca gtggagtacc aggcccccat ctacgatgag ccccccatgg acgtgcaatt | 1560 |
| cgaggctggc gggggctacc aggccggctc tccccagcgg tcgccgggcc gtaagccccg | 1620 |
| gccgttcctc cagcccaaca gcagggcccc ccctcgccc tgccagcagc tggtgctcac | 1680 |
| caagcagaag tgtcccgagc gcttcctgag cctggagtac agtcccgccg gcaaggagta | 1740 |
| cgtgcggcag ctggtctacg tggagcaggc gggctccagc cccaagctgc gcgccggccc | 1800 |
| gcggcacaag tacgcgccca cccggcgg tggttcgtac tccttgcagc ccagcccctg | 1860 |
| cctgctgagg gaccagcgcc tgggcgtcaa gtccggagac tacagcacca tggagggacc | 1920 |
| tgagctgcgg cacagccagc cgcccacgcc gctgccacag gccaggagg atgccatgtc | 1980 |
| ctggtccagc cagcaggaca ccctgtcctc cacaggctac tccccgggca cgcgcaagcg | 2040 |
| gaagagcaga aagccctctt tgtgccaagc caccagcgcc accccactg agggccccgg | 2100 |
| ggacctgctt gtggagcagc cctggccga ggaacagccc ccgtgcggga ccagcctcgc | 2160 |
| ccccgtgaag cgagcggaag gtgaggccga aggggcgcgg ggcgcggccg agcccttcct | 2220 |
| ggcgcaggct cggctggcct gggaggcgca gcaggcccac ttccacatga agcagaggag | 2280 |
| cagctgggac tcccagcagg acggctctgg ctacgagagc gacggcgccc tgccactgcc | 2340 |
| catgcccggg ccggtggtgc gggccttcag cgaggacgag cgctggccc agcaggagaa | 2400 |
| caggcactgg aggaggggca ccttcgagaa gctaggcttc ccccagatcc tgctggagaa | 2460 |
| gagcgtctcc gtgcagacca acctggcctc accagagccc tacctccacc cctcacagtc | 2520 |
| tgaggacctc gctgcctgtg cccagttcga gagcagccgg cagagccgca gcggcgttcc | 2580 |
| cagctccagc tgcgtcttcc ccactttcac gctgcgcaag ccctcctcgg agacggacat | 2640 |
| cgagaactgg gcctccaagc acttcaacaa gcacacgcag ggcctcttcc ggcggaaggt | 2700 |
| gtccatcgcc aacatgctgg cctggagcag cgagtccatc aagaagccca tgatcgtgac | 2760 |
| aagcgaccgg cacgtgaaga aggaggcctg cgagctcttc aagctgatcc agatgtacat | 2820 |
| gggtgaccgg cgggccaagg ccgacccact gcacgtggcc ctggaggtgg ccaccaaggg | 2880 |
| ctggagcgtg cagggcctgc gggacgagct ctacatccag ctgtgccggc agaccaccga | 2940 |
| gaacttccgc ctggagagcc tggccgcgcg ctgggagctc atggccatct gcctggcctt | 3000 |
| tttcccgccc accccaagt tccactccta cctggaaggc tacatctacc ggcacatgga | 3060 |
| ccccgtcaat gacactaaag tgacacagca cataaaagag ctcctggaaa gaaacactaa | 3120 |
| gaagaagtcc aaattgagaa agaaacccaa gccttatgtt gaagagccgg atggggtggc | 3180 |
| gataagcacg tatgccaagt actgttacca caagctacag aaggcagccc tgaccggggc | 3240 |
| caagaagggg ctgaagaagc ccaacgtgga ggagatccgg catgccaaga cgccgtgtt | 3300 |
| cagcccgtcc atgttcggca gcgcactgca ggaggtcatg ggcatgcaga gagcgcta | 3360 |
| ccccgagcgc cagctgccct gggtgcagac acggctctct gaggaggtgc tggcgctcaa | 3420 |
| cggtgaccag acagagggca tcttcagggt ccctggggac attgacgagg tgaatgccct | 3480 |
| gaagctgcag gtgaccagt ggaaggtgcc cacaggcctg aagaccccc acgtccctgc | 3540 |
| gtccctgctg aagctgtggt accgggagct ggaggagccc ctgatcccgc acgagttcta | 3600 |

| | |
|---|---|
| cgagcagtgc atcgcgcact acgacagccc cgaggcggcg gtggccgtgg tgcacgcgct | 3660 |
| gccccgcatc aaccgcatgg tgctgtgcta cctcatccgc ttcctgcagg tcttcgtgca | 3720 |
| gccggccaac gtcgcggtca ccaagatgga tgtcagcaac ctggccatgg tgatggcgcc | 3780 |
| caactgcttg cgctgccagt ccgacgaccc gcgcgtcatc ttcgagaaca cccgcaagga | 3840 |
| gatgtccttc ctgcgggtgc tcatccagca cctggacacc agcttcatgg agggtgtgct | 3900 |
| gtagcggggg cgcccgggga caggagggat gtcctgccgc cccagccag gccgaactcc | 3960 |
| gcactcgctc tcccggcaga ggggccagaa tcgcccggcc cagccctgga gccccctcca | 4020 |
| ctcccccagg cccctggccc cggcgctccc cacgtcttct gcctggtctg agggtgcagc | 4080 |
| cagggcacag cagcggcggg gagggcgcct ctggcccccc acctcacggc cagttcccgc | 4140 |
| gggcaccgcc tcgccctccg ctggccgcgg gtcagctccg agaaagtgcc ttctgtgtcc | 4200 |
| tggagccgag cgacgctgcc tccttggggc cgggctgcct ccctgtggct cctgcgcgcc | 4260 |
| ctggcctggg ccttgcccag ccgccccggt ctctccttcc cttttctctg tcctcgtcct | 4320 |
| ggcctgcagc tcttcccagc cccgagagag cttcccgacc tgtccccgcc tcctctccct | 4380 |
| ccctcggccc gtggtcccca gctggtgact gctcaggagt ttgggggctc caggacagtg | 4440 |
| ggcccggggc ctggcaggct ctcggtgggt ggggtgggg ccccaaacc aaagtcctct | 4500 |
| ggggtaggga gcagggctgg gcaggcattc tggggcagg gtgggggagg ggcgagagta | 4560 |
| tttttttctt cgtgtaactg taaatccaga atctatcctg catcgcagcc caccgtgtat | 4620 |
| agagatataa atagagggaa agatataaga actaaatttg ctaatgacat agttttaacc | 4680 |
| taaatgctat ttatctctga gccgtccccg tcctccgtgc agagcaagtt gaggtcattc | 4740 |
| cttcttttct tctccgatct ttttcttgg cttctgacca aaaccaagc tctacccat | 4800 |
| ccccatccca gacctgcagg agacgagcga gcgggaaggc gccggccg ggactgtccg | 4860 |
| ttctcggggc cagagctgct gggggaccga gtttgtacat tttccatttt ggaattttga | 4920 |
| gttccaattg ttgtaaaact taatttctcc ccagttttta tatatatatt ttttagagtt | 4980 |
| ccgtttttat ttattaaaaa caaaagcccc agccctgccg aggcctgggc ggcgtcctca | 5040 |
| gtcgggtggt cccggggcct ttgcggtccc gccggctga cgctcgcc ccgacgcatg | 5100 |
| gacccgagag gcgacgacac gagtgaataa agtgcacatg gaccctg | 5147 |

<210> SEQ ID NO 17
<211> LENGTH: 400
<212> TYPE: DNA
<213> ORGANISM: Artificial Sequence
<220> FEATURE:
<223> OTHER INFORMATION: LRR2 domain recombinant

<400> SEQUENCE: 17

| | |
|---|---|
| gatcgtcgaa atacgcctag aacagaactc catcaaagcc atccctgcag gagccttcac | 60 |
| ccagtacaag aaactgaagc gaatagacat cagcaagaat cagatatcgg atattgctcc | 120 |
| agatgccttc cagggcctga atcactcac atcgctggtc ctgtatggga acaagatcac | 180 |
| cgagattgcc aagggactgt tgatgggct ggtgtcccta cagctgctcc tcctcaatgc | 240 |
| caacaagatc aactgcctgc gggtgaacac gtttcaggac ctgcagaacc tcaacttgct | 300 |
| ctccctgtat gacaacaagc tgcagaccat cagcaagggg ctcttcgccc ctctgcagtc | 360 |
| catccagaca ctccacttag cccaaaaccc acccggggtc | 400 |

<210> SEQ ID NO 18
<211> LENGTH: 19

```
<212> TYPE: DNA
<213> ORGANISM: Artificial Sequence
<220> FEATURE:
<223> OTHER INFORMATION: PRIMER

<400> SEQUENCE: 18
agggaagcct acgcagatg                                                   19

<210> SEQ ID NO 19
<211> LENGTH: 20
<212> TYPE: DNA
<213> ORGANISM: Artificial Sequence
<220> FEATURE:
<223> OTHER INFORMATION: PRIMER

<400> SEQUENCE: 19
tggacagtgg gcgattttat                                                  20

<210> SEQ ID NO 20
<211> LENGTH: 18
<212> TYPE: DNA
<213> ORGANISM: Artificial Sequence
<220> FEATURE:
<223> OTHER INFORMATION: PRIMER

<400> SEQUENCE: 20
agccccacac aaacaagg                                                    18

<210> SEQ ID NO 21
<211> LENGTH: 19
<212> TYPE: DNA
<213> ORGANISM: Artificial Sequence
<220> FEATURE:
<223> OTHER INFORMATION: PRIMER

<400> SEQUENCE: 21
aagctgggct tgctgtagg                                                   19

<210> SEQ ID NO 22
<211> LENGTH: 18
<212> TYPE: DNA
<213> ORGANISM: Artificial Sequence
<220> FEATURE:
<223> OTHER INFORMATION: PRIMER

<400> SEQUENCE: 22
gcagcgctca accctagt                                                    18

<210> SEQ ID NO 23
<211> LENGTH: 20
<212> TYPE: DNA
<213> ORGANISM: Artificial Sequence
<220> FEATURE:
<223> OTHER INFORMATION: PRIMER

<400> SEQUENCE: 23
cttctggccc aactcttgac                                                  20

<210> SEQ ID NO 24
<211> LENGTH: 20
<212> TYPE: DNA
<213> ORGANISM: Artificial Sequence
<220> FEATURE:
<223> OTHER INFORMATION: PRIMER

<400> SEQUENCE: 24
```
cgcatgtctc tgacccctac                                              20

<210> SEQ ID NO 25
<211> LENGTH: 20
<212> TYPE: DNA
<213> ORGANISM: Artificial Sequence
<220> FEATURE:
<223> OTHER INFORMATION: PRIMER

<400> SEQUENCE: 25
gagctgttag cttggtgcaa                                              20

<210> SEQ ID NO 26
<211> LENGTH: 20
<212> TYPE: DNA
<213> ORGANISM: Artificial Sequence
<220> FEATURE:
<223> OTHER INFORMATION: PRIMER

<400> SEQUENCE: 26
actttgtcaa gctcatttcc                                              20

<210> SEQ ID NO 27
<211> LENGTH: 20
<212> TYPE: DNA
<213> ORGANISM: Artificial Sequence
<220> FEATURE:
<223> OTHER INFORMATION: PRIMER

<400> SEQUENCE: 27
tgcagcgaac tttattgatg                                              20

<210> SEQ ID NO 28
<211> LENGTH: 21
<212> TYPE: DNA
<213> ORGANISM: Artificial Sequence
<220> FEATURE:
<223> OTHER INFORMATION: PRIMER

<400> SEQUENCE: 28
cacggccatc ctatatggta a                                            21

<210> SEQ ID NO 29
<211> LENGTH: 20
<212> TYPE: DNA
<213> ORGANISM: Artificial Sequence
<220> FEATURE:
<223> OTHER INFORMATION: PRIMER

<400> SEQUENCE: 29
gagacatttt cccgttcacc                                              20

<210> SEQ ID NO 30
<211> LENGTH: 20
<212> TYPE: DNA
<213> ORGANISM: Artificial Sequence
<220> FEATURE:
<223> OTHER INFORMATION: PRIMER

<400> SEQUENCE: 30
gctaccttgg agcctcagtc                                              20

<210> SEQ ID NO 31
<211> LENGTH: 21
<212> TYPE: DNA
<213> ORGANISM: Artificial Sequence

<220> FEATURE:
<223> OTHER INFORMATION: PRIMER

<400> SEQUENCE: 31
ctcgtcacaa gcagggttaa g                                              21

<210> SEQ ID NO 32
<211> LENGTH: 22
<212> TYPE: DNA
<213> ORGANISM: Artificial Sequence
<220> FEATURE:
<223> OTHER INFORMATION: PRIMER

<400> SEQUENCE: 32
gcattatgac ccagaaactg gt                                             22

<210> SEQ ID NO 33
<211> LENGTH: 20
<212> TYPE: DNA
<213> ORGANISM: Artificial Sequence
<220> FEATURE:
<223> OTHER INFORMATION: PRIMER

<400> SEQUENCE: 33
taggtgccag gagcacattt                                                20

<210> SEQ ID NO 34
<211> LENGTH: 20
<212> TYPE: DNA
<213> ORGANISM: Artificial Sequence
<220> FEATURE:
<223> OTHER INFORMATION: PRIMER

<400> SEQUENCE: 34
agcgcagatg gatcctaaca                                                20

<210> SEQ ID NO 35
<211> LENGTH: 20
<212> TYPE: DNA
<213> ORGANISM: Artificial Sequence
<220> FEATURE:
<223> OTHER INFORMATION: PRIMER

<400> SEQUENCE: 35
gagtcctgca aatctgcgtt                                                20

<210> SEQ ID NO 36
<211> LENGTH: 22
<212> TYPE: DNA
<213> ORGANISM: Artificial Sequence
<220> FEATURE:
<223> OTHER INFORMATION: PRIMER

<400> SEQUENCE: 36
cgaccattgt tagccacata cg                                             22

<210> SEQ ID NO 37
<211> LENGTH: 23
<212> TYPE: DNA
<213> ORGANISM: Artificial Sequence
<220> FEATURE:
<223> OTHER INFORMATION: PRIMER

<400> SEQUENCE: 37
tcgtcctgaa gatactgcag gtt                                            23

```
<210> SEQ ID NO 38
<211> LENGTH: 23
<212> TYPE: DNA
<213> ORGANISM: Artificial Sequence
<220> FEATURE:
<223> OTHER INFORMATION: PRIMER

<400> SEQUENCE: 38
atatgtgggc caggatgaaa gtt                                           23

<210> SEQ ID NO 39
<211> LENGTH: 21
<212> TYPE: DNA
<213> ORGANISM: Artificial Sequence
<220> FEATURE:
<223> OTHER INFORMATION: PRIMER

<400> SEQUENCE: 39
tcgttcccca caggaatctc t                                             21

<210> SEQ ID NO 40
<211> LENGTH: 24
<212> TYPE: DNA
<213> ORGANISM: Artificial Sequence
<220> FEATURE:
<223> OTHER INFORMATION: PRIMER

<400> SEQUENCE: 40
tgtctggaga ttcgacttga agtc                                          24

<210> SEQ ID NO 41
<211> LENGTH: 19
<212> TYPE: DNA
<213> ORGANISM: Artificial Sequence
<220> FEATURE:
<223> OTHER INFORMATION: PRIMER

<400> SEQUENCE: 41
tgagttccag ggcacacca                                                19

<210> SEQ ID NO 42
<211> LENGTH: 24
<212> TYPE: DNA
<213> ORGANISM: Artificial Sequence
<220> FEATURE:
<223> OTHER INFORMATION: PRIMER

<400> SEQUENCE: 42
agttgccctc ttatgaagga gaag                                          24

<210> SEQ ID NO 43
<211> LENGTH: 20
<212> TYPE: DNA
<213> ORGANISM: Artificial Sequence
<220> FEATURE:
<223> OTHER INFORMATION: PRIMER

<400> SEQUENCE: 43
ggagtgtcgt cccagcacat                                               20

<210> SEQ ID NO 44
<211> LENGTH: 20
<212> TYPE: DNA
<213> ORGANISM: Artificial Sequence
<220> FEATURE:
<223> OTHER INFORMATION: PRIMER
```

```
<400> SEQUENCE: 44
ctccactcac ggcaaattca                                              20

<210> SEQ ID NO 45
<211> LENGTH: 20
<212> TYPE: DNA
<213> ORGANISM: Artificial Sequence
<220> FEATURE:
<223> OTHER INFORMATION: PRIMER

<400> SEQUENCE: 45
gcctcacccc atttgatgtt                                              20

<210> SEQ ID NO 46
<211> LENGTH: 130
<212> TYPE: PRT
<213> ORGANISM: Homo sapiens

<400> SEQUENCE: 46

Ile Val Glu Ile Arg Leu Glu Gln Asn Ser Ile Lys Ala Ile Pro Ala
 1               5                  10                  15

Gly Ala Phe Thr Gln Tyr Lys Lys Leu Lys Arg Ile Asp Ile Ser Lys
            20                  25                  30

Asn Gln Ile Ser Asp Ile Ala Pro Asp Ala Phe Gln Gly Leu Lys Ser
        35                  40                  45

Leu Thr Ser Leu Val Leu Tyr Gly Asn Lys Ile Thr Glu Ile Ala Lys
    50                  55                  60

Gly Leu Phe Asp Gly Leu Val Ser Leu Gln Leu Leu Leu Leu Asn Ala
65                  70                  75                  80

Asn Lys Ile Asn Cys Leu Arg Val Asn Thr Phe Gln Asp Leu Gln Asn
                85                  90                  95

Leu Asn Leu Leu Ser Leu Tyr Asp Asn Lys Leu Gln Thr Ile Ser Lys
            100                 105                 110

Gly Leu Phe Ala Pro Leu Gln Ser Ile Gln Thr Leu His Leu Ala Gln
        115                 120                 125

Asn Pro
130
```